US012638455B2

(12) United States Patent
Shlipak et al.

(10) Patent No.: US 12,638,455 B2
(45) Date of Patent: May 26, 2026

(54) KIDNEY HEALTH MONITORING IN HYPERTENSION PATIENTS

(71) Applicants: THE REGENTS OF THE UNIVERSITY OF CALIFORNIA, Oakland, CA (US); THE U.S. GOVERNMENT AS REPRESENTED BY THE DEPARTMENT OF VETERANS AFFAIRS, Washington, DC (US)

(72) Inventors: Michael George Shlipak, San Francisco, CA (US); Michelle Estrella, San Francisco, CA (US); Joachim H. Ix, La Jolla, CA (US); Rebecca Scherzer, San Francisco, CA (US)

(73) Assignees: THE REGENTS OF THE UNIVERSITY OF CALIFORNIA, Oakland, CA (US); THE U.S. GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 1056 days.

(21) Appl. No.: 17/282,854

(22) PCT Filed: Oct. 1, 2019

(86) PCT No.: PCT/US2019/054129
§ 371 (c)(1),
(2) Date: Apr. 5, 2021

(87) PCT Pub. No.: WO2020/072533
PCT Pub. Date: Apr. 9, 2020

(65) Prior Publication Data
US 2023/0184783 A1     Jun. 15, 2023

Related U.S. Application Data

(60) Provisional application No. 62/742,064, filed on Oct. 5, 2018.

(51) Int. Cl.
*G01N 33/68*          (2006.01)

(52) U.S. Cl.
CPC ..... *G01N 33/6863* (2013.01); *G01N 2333/54* (2013.01); *G01N 2333/70578* (2013.01); *G01N 2333/924* (2013.01); *G01N 2800/347* (2013.01)

(58) Field of Classification Search
None
See application file for complete search history.

(56) References Cited

U.S. PATENT DOCUMENTS 9,238,837 B2      1/2016  Schmidt-Ott et al.
2011/0065608 A1   3/2011  LaBrie et al.

FOREIGN PATENT DOCUMENTS

WO    WO-2010/057184 A2    5/2010
WO    WO2011/133794    * 10/2011  ............. G01N 33/68

OTHER PUBLICATIONS

Beddhu et al., Ann Intern Med. 2017; 167: 375-383. doi:10.7326/M16-2966 (Year: 2017).*
Kiernan et al., Am J Kidney Dis. 83(2):151-161 (Year: 2023).*
Scherzer et al., Nephrol Dial Transplant (2016) 31: 1478-1485 (Year: 2016).*
ACCORD Study Group et al., Effects of Intensive Blood-Pressure Control in Type 2 Diabetes Mellitus, New England Journal of Medicine, 362(17):1575-85 (2010).
Ambrosius et al., The design and rationale of a multicenter clinical trial comparing two strategies for control of systolic blood pressure: The Systolic Blood Pressure Intervention Trial (SPRINT), Clinical Trials, 11(5):532-46 (2014).
Appel et al., Intensive Blood-Pressure Control in Hypertensive Chronic Kidney Disease, New England Journal of Medicine, 363(10):918-29 (2010).
Argyropoulos et al., Rediscovering Beta-2 Microglobulin as a Biomarker across the Spectrum of Kidney Diseases, Frontiers in Medicine, 4:73 (2017).
Bacchetti, Peer review of statistics in medical research: the other problem, BMJ, 324(7348):1271-3 (2002).
Beddhu et al., Effects of intensive systolic blood pressure control on kidney and cardiovascular outcomes in persons without kidney disease: A secondary analysis of a randomized trial, Ann. Intern. Med., 167(6):375-83 (Sep. 2017).
Birn et al., Renal albumin absorption in physiology and pathology, Kidney International, 69(3):440-9 (2006).
(Continued)

*Primary Examiner* — Christina M Borgeest
(74) *Attorney, Agent, or Firm* — MARSHALL, GERSTEIN & BORUN LLP

(57)          ABSTRACT
The present disclosure provides methods of determining whether a subject treated for hypertension should continue hypertension treatment. In exemplary embodiments, the method comprises measuring the level of at least two of the following in a urine sample obtained from the subject: (i) Alpha-1 microglobulin (aim); (ii) kidney injury molecule (KIM-1); and (iii) Chitinase-3-like protein (YKL-40); wherein the subject should continue the hypertension treatment, when the levels are decreased or unchanged, relative to a control level, and wherein the subject should discontinue or decrease the hypertension treatment, when the levels are increased, relative to a control level. Related methods, kits, assay systems, systems comprising machine readable instructions, computer-readable storage media, and methods implemented by a processor in a computer are furthermore provided herein.

5 Claims, 3 Drawing Sheets
Specification includes a Sequence Listing.

(56)                    References Cited

OTHER PUBLICATIONS

Blank et al., Review of Qualification Data for Biomarkers of Nephrotoxicity Submitted by the Predictive Safety Testing Consortium, Center for Drug Evaluation and Research, U.S. Food and Drug Administration (2009).

Bonventre et al., Next-generation biomarkers for detecting kidney toxicity, Nat Biotech., 28(5):436-40 (2010).

Bullen et al., The SPRINT trial suggests that markers of tubule cell function in the urine associate with risk of subsequent acute kidney injury while injury markers elevate after the injury, Kidney Int., 96(2):470-9 (Aug. 2019).

Cross et al., Analytical Validation of the ReEBOV Antigen Rapid Test for Point-of-Care Diagnosis of Ebola Virus Infection, J. Infect. Dis., 214(Suppl 3):S210-217 (2016).

Deaton et al., Use of laser nephelometry in the measurement of serum proteins, Clin. Chem., 22(9):1465-71 (Sep. 1976).

El-Achkar et al., Uromodulin in Kidney Injury: An Instigator, Bystander, or Protector?, American Journal of Kidney Diseases, 59(3):452-61 (2012).

Endre et al., Early detection of acute kidney injury: Emerging new biomarkers (Review Article), Nephrology, 13(2):91-8 (2008).

Erlandsen et al., Evaluation of the Dade Behring N Latex Cystatin C assay on the Dade Behring Nephelometer II System, Scand. J. Clin. Lab Invest., 59(1):1-8 (Feb. 1999).

European Patent Application No. 19869964.7, Extended European Search Report, dated Aug. 8, 2022.

Fisher et al., Comparison of associations of urine protein-creatinine ratio versus albumin-creatinine ratio with complications of CKD: a cross-sectional analysis, Am. J. Kidney Dis., 62(6):1102-8 (2013).

Garimella et al., Markers of kidney tubule function and risk of cardiovascular disease events and mortality in the SPRINT trial, Eur. Heart J., 40(42):3486-93 (Nov. 2019).

Grant et al., A paper-based immunoassay to determine HPV vaccination status at the point-of-care, Vaccine, 34(46):5656-63 (2016).

Huen et al., Molecular phenotyping of clinical AKI with novel urinary biomarkers, American Journal of Physiology—Renal Physiology, 309(5):F406-F13 (2015).

International Application No. PCT/US2019/054129, International Search Report and Written Opinion, mailed Jan. 10, 2020.

Jotwani et al., Urinary Biomarkers of Tubular Damage Are Associated with Mortality but Not Cardiovascular Risk among Systolic Blood Pressure Intervention Trial Participants with Chronic Kidney Disease, Am. J. Nephrol., 49:346-55 (2019).

Kazancioglu, Risk factors for chronic kidney disease: an update, Kidney International Supplements, 3(4):368-71 (2013).

Kimura et al., Identification of biomarkers for development of end-stage kidney disease in chronic kidney disease by metabolomic profiling, Scientific Reports, 6:26138 (2016).

Klahr et al., The Effects of Dietary Protein Restriction and Blood-Pressure Control on the Progression of Chronic Renal Disease, New England Journal of Medicine, 330(13):877-84 (1994).

Koraishy et al., Can we predict recovery from severe acute kidney injury with biomarkers?, Semin. Dial., 27(3):236-9 (May-Jun. 2014).

Ku et al., Association between strict blood pressure control during chronic kidney disease and lower mortality after onset of end-stage renal disease, Kidney International, 87(5):1055-60 (May 2015).

Kuster et al., A sensitive and specific quantitation method for determination of serum cardiac myosin binding protein-C by electrochemiluminescence immunoassay, J. Vis. Exp., 8(78):50786 (Aug. 2013).

Landsman et al., Efficient analysis of case-control studies with sample weights, Statistics in Medicine, 32(2):347-60 (2013).

Lee et al., Distinct Dimensions of Kidney Health and Risk of Cardiovascular Disease, Heart Failure, and Mortality, Hypertension, 74(4):872-9 (Oct. 2019).

Lewington et al., Age-specific relevance of usual blood pressure to vascular mortality: a meta-analysis of individual data for one million adults in 61 prospective studies, The Lancet, 360(9349):1903-13 (Dec. 2002).

Malhotra et al., Effects of Intensive Blood Pressure Lowering on Kidney Tubule Injury in CKD: A Longitudinal Subgroup Analysis in SPRINT, Am. J. Kidney Dis., 73(1):21-30 (Jan. 2019).

Muiru et al., Kidney disease risk factors associate with urine biomarkers concentrations in HIV-positive persons; a cross-sectional study, BMC Nephrol., 20(1):4 (Jan. 2019).

Nadkarni et al., Association of Urinary Biomarkers of Inflammation, Injury, and Fibrosis with Renal Function Decline: The ACCORD Trial, Clinical Journal of the American Society of Nephrology, 11(8):1343-52 (2016).

Nadkarni et al., Effect of Intensive Blood Pressure Lowering on Kidney Tubule Injury: Findings From the ACCORD Trial Study Participants, Am. J. Kidney Dis., 73(1):31-38 (Jan. 2019).

Oh et al., Comparison of conventional ELISA with electrochemiluminescence technology for detection of amyloid-beta in plasma, J. Alzheimers Dis., 21(3):769-73 (2010).

Parikh et al., New biomarkers of acute kidney injury, Critical Care Medicine, 36(4):S159-S65 (2008).

Parikh et al., Urinary IL-18 is an early predictive biomarker of acute kidney injury after cardiac surgery, Kidney International, 70(1):199-203 (2006).

Penders et al., Alpha 1-microglobulin: clinical laboratory aspects and applications, Clinica Chimica Acta, 346(2):107-18 (2004).

Peralta et al. Associations of Urinary Levels of Kidney Injury Molecule-1 (KIM-1) and Neutrophil Gelatinase-Associated Lipocalin (NGAL) With Kidney Function Decline in the Multi-Ethnic Study of Atherosclerosis (MESA). American Journal of Kidney Diseases, 60(6):904-11 (2012).

Peralta et al., Effect of Intensive Versus Usual Blood Pressure Control on Kidney Function Among Individuals With Prior Lacunar Stroke: A Post Hoc Analysis of the Secondary Prevention of Small Subcortical Strokes (SPS3) Randomized Trial, Circulation, 133(6):584-91 (2016).

Porterfield et al., A simple and general method for determining the protein and nucleic acid content of viruses by UV absorbance, Virology, 407(2):281-8 (Nov. 2010).

Scherzer et al., Use of urine biomarker-derived clusters to predict the risk of chronic kidney disease and all-cause mortality in HIV-infected women, Nephrol. DIal. Transplant., 31(9):1478-85 (Sep. 2016).

Schmidt et al., Chitinase-Like Protein Brp-39/YKL-40 Modulates the Renal Response to Ischemic Injury and Predicts Delayed Allograft Function, Journal of the American Society of Nephrology, 24(2):309-19 (2013).

Shastri et al., Cystatin C and Albuminuria as Risk Factors for Development of CKD Stage 3: The Multi-Ethnic Study of Atherosclerosis (MESA), American journal of kidney diseases, 57(6):832-40 (2011).

Siawaya et al., An evaluation of commercial fluorescent bead-based luminex cytokine assays, PLoS One, 3(7):e2535 (Jul. 2008).

Siew et al., Biological Markers of Acute Kidney Injury, Journal of the American Society of Nephrology, 22(5):810-20 (2011).

Sipahi et al., Effects of Normal, Pre-Hypertensive, and Hypertensive Blood Pressure Levels on Progression of Coronary Atherosclerosis, Journal of the American College of Cardiology, 48(4):833-8 (2006).

SPRINT Research Group, A Randomized Trial of Intensive versus Standard Blood-Pressure Control, New England Journal of Medicine, 373(22):2103-16 (2015).

SPS3 Study Group et al., Blood-pressure targets in patients with recent lacunar stroke: the SPS3 randomised trial, The Lancet, 382(9891):507-15 (Aug. 2013).

Urquidi et al., CCL18 in a multiplex urine-based assay for the detection of bladder cancer, PLoS One, 7(5):e37797 (2012).

Vaidya et al., Biomarkers of Acute Kidney Injury, Annual review of pharmacology and toxicology, 48:463-93 (2008).

Vasan et al., Impact of High-Normal Blood Pressure on the Risk of Cardiovascular Disease, New Engl. J. Med., 345(18):1291-7 (2001).

Whelton et al., 2017 ACC/AHA/AAPA/ABC/ACPM/AGS/APhA/ASH/ASPC/NMA/PCNA Guideline for the Prevention, Detection, Evaluation, and Management of High Blood Pressure in Adults. A Report of the American College of Cardiology/American Heart

(56) References Cited

OTHER PUBLICATIONS

Association Task Force on Clinical Practice Guidelines, Journal of the American College of Cardiology, 71(19):e127-e248 (2017).

Wright et al., Effect of blood pressure lowering and antihypertensive drug class on progression of hypertensive kidney disease: Results from the AASK trial, JAMA, 288(19):2421-31 (2002).

Zhang et al., Kidney Damage Biomarkers and Incident Chronic Kidney Disease During Blood Pressure Reduction: A Case-Control Study, Ann. Intern. Med., 169(6):610-618 (Nov. 2018).

Fuchs et al., Biomarkers for drug-induced renal damage and nephrotoxicity—an overview for applied toxicology, The AAPS Journal, 1394):615-31 (Oct. 2011).

Ptinopoulou et al., The effect of antihypertensive drugs on chronic kidney disease: a comprehensive review, Hypertension Research, 36(2):91-101 (Feb. 2013).

Zhang et al., The impact of blood pressure on kidney function in the elderly: A cross-sectional study, Ann. Intern. Med., 169(9):1-17 (Oct. 23, 2018).

* cited by examiner

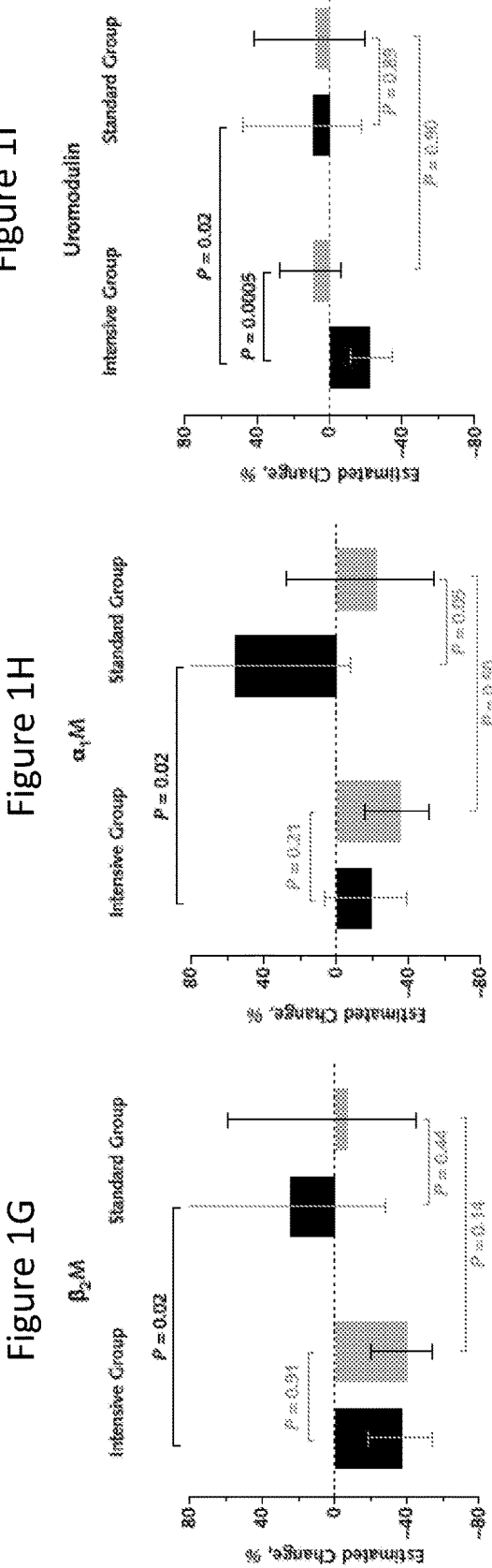

The intensive group had 128 case participants, and the standard group had 34. In each intervention group, 1 control participant was matched to each case participant on age (within 5 years), sex, race, and baseline eGFR (within 5 mL/min/1.73 m²). The 1-year changes were estimated from separate linear mixed models for each biomarker, with adjustment for $\log_2$-transformed urine creatinine and systolic blood pressure. Error bars denote the 95% CIs. The $\chi$-axes are truncated at ± 80%. The 95% CI upper bounds for several biomarkers among case participants in the standard group were truncated. The 95% CI upper bounds of 1-year changes in KIM-1, MCP-1, $\beta_2$M, and $\alpha_1$M extend to 97%, 89%, 114%, and 153%, respectively. Brackets with P values represent comparisons of 1-year changes between respective groups at bracket tails. P values less than 0.05 were considered statistically significant and are in boldface. The numerical values of the 1-year change and 95% CIs are presented in Appendix Table 6. The dotted lines represent baseline. ACR = albumin-creatinine ratio; $\alpha_1$M = $\alpha_1$-microglobulin; $\beta_2$M = $\beta_2$-microglobulin; CKD = chronic kidney disease; eGFR = estimated glomerular filtration rate; IL-18 = interleukin-18; KIM-1 = kidney injury molecule-1; MCP-1 = monocyte chemoattractant protein-1; NGAL = neutrophil gelatinase-associated lipocalin; SPRINT = Systolic Blood Pressure Intervention Trial; YKL-40 = anti-chitinase-3-like protein 1.

KIDNEY HEALTH MONITORING IN HYPERTENSION PATIENTS

CROSS-REFERENCE TO RELATED APPLICATIONS

This is a U.S. National Phase of International Application No. PCT/US2019/054129, filed Oct. 1, 2019, which claims priority to U.S. Provisional Application No. 62/742,064, filed Oct. 5, 2018.

GRANT FUNDING DISCLOSURE

This invention was made with government support under grants no. R01 DK098234 and K24 DK110427 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 189,111 byte ASCII (Text) file named "53296A_Seqlisting.txt"; created on Oct. 1, 2019.

BACKGROUND

It has been well established that lower blood pressures are strongly associated with substantial cardiovascular and mortality benefit.[1-3] The Systolic Blood Pressure Intervention Trial (SPRINT) was a pivotal randomized controlled trial which demonstrated that intensive systolic blood pressure (SBP) management to <120 mmHg reduced rates of major cardiovascular events and all-cause mortality, compared to standard management to <140 mmHg.[4] Despite these benefits, one notable harm was a more than 3-fold increased incidence of chronic kidney disease (CKD) in the intensive vs. standard arm. Nonetheless, recent guidelines by the American College of Cardiology and American Heart Association have lowered blood pressure targets for hypertension diagnosis and management.[5] These policy changes may dramatically increase the incidence of CKD at the population level and could pose a significant public health concern. On the other hand, in the setting of intensive blood pressure lowering, kidney function decline may reflect benign manifestations of hemodynamic accommodation. Thus, there remains uncertainty regarding whether incident CKD that develops during intensive blood pressure lowering is accompanied by intrinsic kidney injury or instead reflects hemodynamic changes.

Thus, there is a need for methods which distinguish between intrinsic kidney injury or hemodynamic changes in patients treated with intensive blood pressure lowering medications.

SUMMARY

Presented here for the first time are data demonstrating that, in patients without CKD, higher concentrations of baseline albumin-creatinine ratio (ACR), kidney injury molecule-1 (KIM-1), and monocyte chemoattractant protein-1 (MCP-1) are each significantly associated with higher odds of incident CKD (adjusted OR per doubling (95% CI): 1.50 (1.14, 1.98), 1.51 (1.05, 2.17), and 1.70 (1.13, 2.56), respectively). After 1 year of treatment of patients without baseline CKD, incident CKD cases in the intensive arm had significantly larger declines in ACR, interleukin-18 (IL-18), chitinase-3-like protein 1 (YKL-40), and uromodulin (UMOD), compared with matched controls. The other biomarkers remained the same. When compared with CKD cases in the standard arm, cases in the intensive arm had significantly larger declines in ACR, YKL-40, 32-microglobulin ($\beta$2M), $\alpha$1-microglobulin ($\alpha$1m), and UMOD. Incident CKD in the setting of intensive SBP lowering was not accompanied by elevations of biomarkers of kidney damage and thus may reflect hemodynamic accommodation rather than intrinsic injury.

The present disclosure therefore provides methods of determining whether a subject treated for hypertension should continue hypertension treatment. In exemplary embodiments, the method comprises measuring the level of at least two of the following in a urine sample obtained from the subject: (i) Alpha-1 microglobulin ($\alpha$1m); (ii) kidney injury molecule (KIM-1); and (iii) Chitinase-3-like protein (YKL-40); wherein the subject should continue the hypertension treatment, when the levels are decreased or unchanged, relative to a control level, and wherein the subject should discontinue or decrease treatment with the hypertension medication, when the levels are increased, relative to a control level. In exemplary aspects, the control level is a baseline level of the subject prior to starting a particular hypertension treatment. Thus, in some aspects, the method comprises measuring the level of at least two of the following in a urine sample obtained from the subject: (i) $\alpha$1m; (ii) KIM-1; and (iii) YKL-40; wherein the urine sample is obtained from the subject prior to starting a hypertension treatment. Accordingly, the present disclosure also provides a method of evaluating a subject having elevated or high blood pressure (e.g., a blood pressure of 120 mmHg or higher), said method comprising measuring the level of at least two of the following in a urine sample obtained from the subject: (i) $\alpha$1m; (ii) KIM-1; and (iii) YKL-40, optionally, wherein the subject is not on any hypertension treatment or has never been on any hypertension treatment before. Optionally, the subject having elevated or high blood pressure is one who needs a hypertension treatment. In exemplary aspects, the method further comprises the step of administering to the subject a hypertension treatment, and, optionally further comprises re-measuring the level of at least two of the following in a urine sample obtained from the subject after administering the hypertension treatment: (i) $\alpha$1m; (ii) KIM-1; and (iii) YKL-40. In exemplary aspects, the subject should continue the hypertension treatment, when the levels are decreased or unchanged, relative to a control level (e.g., a baseline level measured before the hypertension treatment started), and the subject should discontinue or decrease the hypertension treatment, when the levels are increased, relative to a control level (e.g., a baseline level measured before the hypertension treatment started). Without being bound to a particular theory, the levels of at least two (if not all three) of (i) $\alpha$1m; (ii) KIM-1; and (iii) YKL-40 are indicative of kidney tubule health of the subject, such that, in exemplary aspects, the method achieves an assessment of kidney tubule health of the subject. For instance, depending on the levels of (i) $\alpha$1m; (ii) KIM-1; and (iii) YKL-40 as measured in the urine sample obtained from the subject, the kidney tubule health of the subject is assessed and determined as healthy enough to continue the hypertension treatment (e.g., when the levels of (i) $\alpha$1m; (ii) KIM-1; and/or (iii) YKL-40 are decreased or unchanged, relative to a control level), or the kidney tubule health of the subject is determined as insufficiently healthy such that the subject should discontinue or decrease the hypertension treatment (e.g., when the levels of (i) $\alpha$1m; (ii) KIM-1; and/or (iii) YKL-40 are increased, relative to a control level).

Methods of assessing kidney tubule health of a subject during hypertension treatment are thus additionally provided herein. In exemplary embodiments, the method comprises measuring the level of at least two of the following in a urine sample obtained from the subject: (i) $\alpha$1m; (ii) KIM-1; and (iii) YKL-40. In exemplary aspects, the subject is assessed for tubulointerstitial health, intra-renal inflammation, or a combination thereof.

Without being bound to a particular theory, kidney tubule health may be an indicator of chronic kidney disease (CKD) or acute kidney injury (AKI). Accordingly, the present disclosure also provides methods of identifying a subject at risk for CKD, or a complication thereof, wherein the subject is on a hypertension treatment (e.g., methods of identifying a subject at risk for CKD, or a complication thereof, during hypertension treatment). In exemplary embodiments, the method comprises measuring the level of at least two of the following in a urine sample obtained from the subject: (i) $\alpha$1m; (ii) KIM-1; and (iii) YKL-40; wherein the subject is at risk for CKD, when the levels are increased, relative to a control level, optionally, wherein the subject also should discontinue or decrease the hypertension treatment.

Further provided are methods of determining a subject's need for treatment for CKD, wherein the subject is on a hypertension treatment (e.g., methods of determining a subject's need for treatment for CKD during hypertension treatment). In exemplary embodiments, the method comprises measuring the level of at least two of the following in a urine sample obtained from the subject: (i) $\alpha$1m; (ii) KIM-1; and (iii) YKL-40; wherein the subject needs treatment for CKD, when the levels are increased, relative to a control level. In some aspects, the subject should also discontinue or decrease the hypertension treatment, when the levels are increased, relative to a control level.

The present disclosure provides methods of diagnosing a subject with a drug-induced kidney injury, wherein the subject is on a hypertension treatment (e.g., methods of diagnosing a subject with a drug-induced kidney injury during hypertension treatment). In exemplary embodiments, the method comprises measuring the level of at least two of the following in a urine sample obtained from the subject: (i) $\alpha$1m; (ii) KIM-1; and (iii) YKL-40; wherein the subject has a drug-induced kidney injury when the levels are increased, relative to a control level. In some aspects, the subject should also discontinue or decrease the hypertension treatment, when the levels are increased, relative to a control level.

Also provided by the present disclosure are methods of treating a subject with hypertension. In exemplary embodiments, the method comprises (a) administering to the subject a hypertension treatment; (b) measuring the level of at least two of the following in a urine sample obtained from the subject: (i) $\alpha$1m; (ii) KIM-1; and (iii) YKL-40; and (c) continuing the hypertension treatment, when the levels are decreased or unchanged, relative to a control level, or discontinuing or decreasing the hypertension treatment, when the levels are increased. In exemplary aspects, the control level is a baseline level of the subject prior to starting a hypertension treatment. Thus, in some aspects, the method comprises measuring the level of at least two of the following in a urine sample obtained from the subject: (i) $\alpha$1m; (ii) KIM-1; and (iii) YKL-40; wherein the urine sample is obtained from the subject prior to the step of administering hypertension treatment to the subject. In exemplary aspects, when the measured levels are increased, the method additionally comprises concurrent treatment of the subject for CKD.

In exemplary embodiments, the subject is a subject being treated for hypertension and the method comprises (A) continuing hypertension treatment, when the levels of at least two of (i) $\alpha$1m, (ii) KIM-1, and (iii) YKL-40, are decreased or unchanged in a urine sample obtained from the subject, relative to a control level, or (B) discontinuing or decreasing hypertension treatment, when the levels of at least two of (i) $\alpha$1m, (ii) KIM-1, and (iii) YKL-40, are increased in a urine sample obtained from the subject, relative to a control level.

In various aspects of the above presently disclosed methods, the subject has high blood pressure, e.g., a blood pressure of 120 mmHg or higher. In some aspects, the subject has high blood pressure, because the subject is not on any hypertension treatment or has never been on any hypertension treatment before or because the subject is one who is on a hypertension treatment which is not effective (or no longer effective) at treating the hypertension in the subject and requires a new, modified hypertension treatment. In various aspects of the above presently disclosed methods, the control level is a baseline level of the subject prior to starting a hypertension treatment (e.g. a new, modified hypertension treatment). In various aspects of the above presently disclosed methods, the methods comprise repeating the measuring step at least about 2 weeks after starting the hypertension treatment (e.g. any new, modified hypertension treatment), and, optionally repeating the measuring step at least about every 3 months.

Related kits, assay systems, systems comprising machine readable instructions, computer-readable storage media, and methods implemented by a processor in a computer are furthermore provided herein.

DETAILED DESCRIPTION

Figure 1:
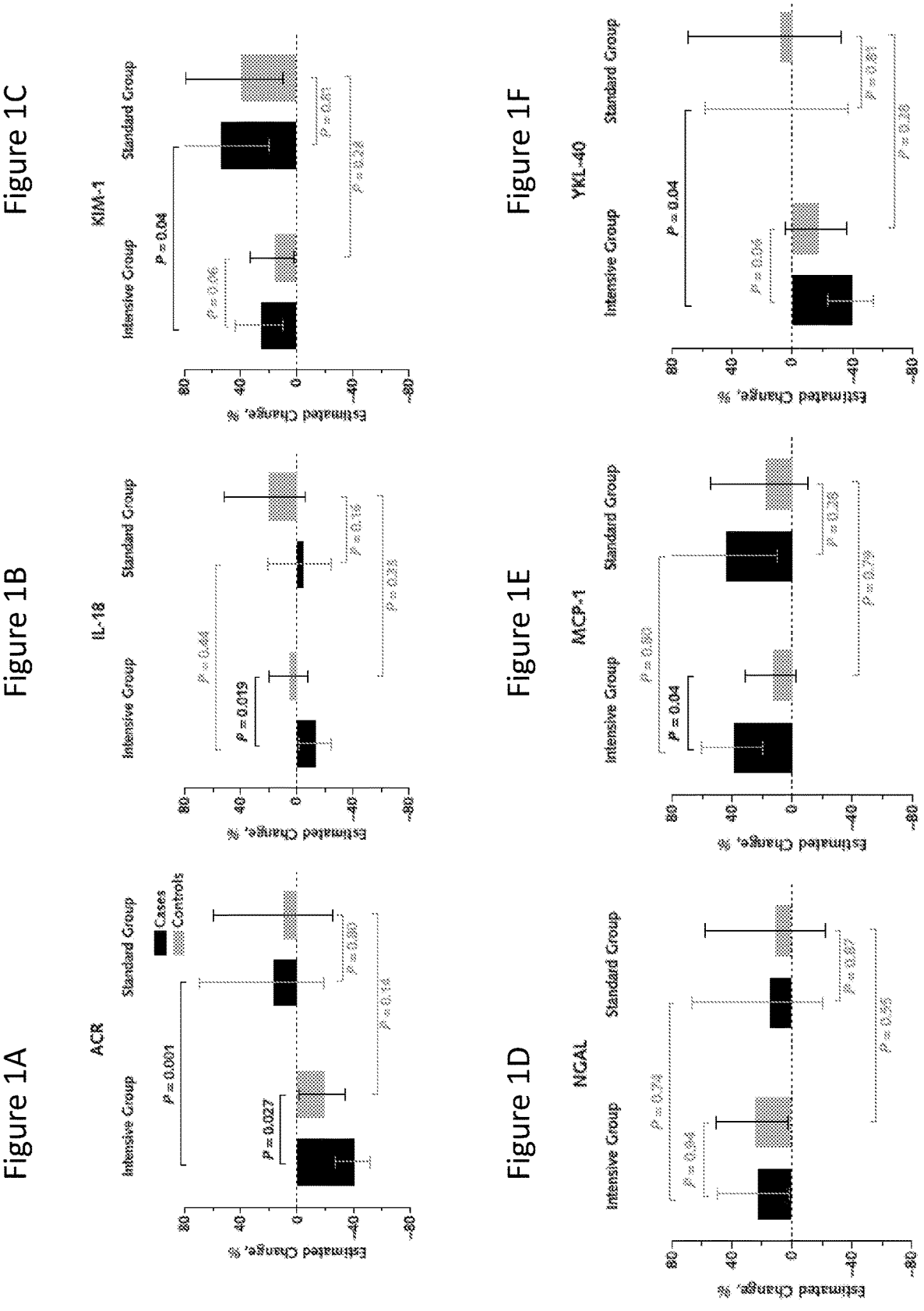
FIGS. 1A-1I demonstrate the 1-year percent changes of nine urinary biomarkers among incident CKD cases and matched controls, stratified by randomization arm, in SPRINT. The black bars denote incident CKD cases, and the gray bars denote matched controls without CKD. There were 128 cases in the intensive arm and 34 in the standard arm; one control was matched per case within each intervention arm on age (within 5 years), sex, race, and baseline eGFR (within 5 ml/min/1.73 m$^2$). The 1-year changes were estimated from separate linear mixed models for each biomarker, adjusting for log 2-transformed urine creatinine and systolic blood pressure. Error bars denote the 95% confidence intervals (CIs). The y-axes are truncated at +/−80%. The 95% CI upper bounds for several biomarkers among cases in the standard arm were truncated: the 95% CI upper bounds of 1-year changes in KIM-1, MCP-1, $\beta$2M, and $\alpha$1M extend to 97%, 89%, 114%, and 163%, respectively. Brackets with p-values represent comparisons of 1-year changes between respective groups at bracket tails. P-values <0.05 were considered statistically significant and have been bolded. The numerical values of the 1-year change and 95% CIs are presented in Appendix Table 7. Full names for each urinary biomarker are as follows: albumin-creatinine ratio (ACR), interleukin-18 (IL-18), kidney injury molecule-1 (KIM-1), neutrophil gelatinase-associated lipocalin (NGAL), monocyte chemoattractant protein-1 (MCP-1), chitinase-3-like protein 1 (YKL-40), beta-2 microglobulin ($\beta$2M), $\alpha$1-microglobulin ($\alpha$1M), and uromodulin (UMOD).

Currently, when clinicians lower SBP to the new AHA guideline levels (between 120 mmHg and 130 mmHg), the patient's serum creatinine in certain instances increases. Based on the rise in serum creatinine, the patient is often diagnosed with CKD, and treatment with hypertension medications is decreased or discontinued. Without being bound to a particular theory, the diagnosis in some aspects is inappropriate, as the patient is not truly suffering from CKD, and, in such situations, treatment with the hypertension medication should not be decreased or discontinued. The invention provided herein provides methods of determining true risk of kidney disease in patients during hypertension treatment.

The present disclosure therefore provides methods of determining whether a subject treated for hypertension should continue hypertension treatment. In exemplary embodiments, the method comprises measuring the level of at least two of the following in a urine sample obtained from the subject: (i) Alpha-1 microglobulin ($\alpha$1m); (ii) kidney injury molecule (KIM-1); and (iii) Chitinase-3-like protein (YKL-40); wherein the subject should continue the hypertension treatment, when the levels are decreased or unchanged, relative to a control level, and wherein the subject should discontinue or decrease treatment with the hypertension medication, when the levels are increased, relative to a control level. In exemplary aspects, the control level is a baseline level of the subject prior to starting a particular hypertension treatment. Thus, in some aspects, the method comprises measuring the level of at least two of the following in a urine sample obtained from the subject: (i) $\alpha$1m; (ii) KIM-1; and (iii) YKL-40; wherein the urine sample is obtained from the subject prior to starting a hypertension treatment. Accordingly, the present disclosure also provides a method of evaluating a subject having elevated or high blood pressure (e.g., a blood pressure of 120 mmHg or higher), said method comprising measuring the level of at least two of the following in a urine sample obtained from the subject: (i) $\alpha$1m; (ii) KIM-1; and (iii) YKL-40, optionally, wherein the subject is not on any hypertension treatment or has never been on any hypertension treatment before. Optionally, the subject having elevated or high blood pressure is one who needs a hypertension treatment. In exemplary aspects, the method further comprises the step of administering to the subject a hypertension treatment, and, optionally further comprises re-measuring the level of at least two of the following in a urine sample obtained from the subject after administering the hypertension treatment: (i) $\alpha$1m; (ii) KIM-1; and (iii) YKL-40. In exemplary aspects, the subject should continue the hypertension treatment, when the levels are decreased or unchanged, relative to a control level (e.g., a baseline level measured before the hypertension treatment started), and the subject should discontinue or decrease the hypertension treatment, when the levels are increased, relative to a control level (e.g., a baseline level measured before the hypertension treatment started). Without being bound to a particular theory, the levels of at least two (if not all three) of (i) $\alpha$1m; (ii) KIM-1; and (iii) YKL-40 are indicative of kidney tubule health of the subject, such that, in exemplary aspects, the method achieves an assessment of kidney tubule health of the subject (e.g., during hypertension treatment). For instance, depending on the levels of (i) $\alpha$1m; (ii) KIM-1; and (iii) YKL-40 as measured in the urine sample obtained from the subject, the kidney tubule health of the subject is assessed and determined as healthy enough to continue the hypertension treatment (e.g., when the levels of (i) $\alpha$1m; (ii) KIM-1; and/or (iii) YKL-40 are decreased or unchanged, relative to a control level), or the kidney tubule health of the subject is determined as insufficiently healthy such that the subject should discontinue or decrease the hypertension treatment (e.g., when the levels of (i) $\alpha$1m; (ii) KIM-1; and/or (iii) YKL-40 are increased, relative to a control level).

Methods of assessing kidney tubule health of a subject during hypertension treatment are thus additionally provided herein. In exemplary embodiments, the method comprises measuring the level of at least two of the following in a urine sample obtained from the subject: (i) $\alpha$1m; (ii) KIM-1; and (iii) YKL-40. In exemplary aspects, the subject is assessed for tubulointerstitial health, intra-renal inflammation, or a combination thereof. By "kidney health" is meant the overall state of function and integrity of the various sub-compartments of comprising the structural and functional units of the kidney or nephrons; these sub-compartments include but are not limited to the glomerulus, kidney tubules, collecting duct, vasculature, and interstitium. "Kidney tubule health" is different from "glomerular health", the former of which refers to the state of function and integrity of the kidney tubules, and the latter term of which refers to the state of function and integrity of the glomerulus which functions as a sieve to retain normal proteins, modulate body fluid retention or excretion, and filter out waste. "Tubulointerstitial health" refers to the state of function and integrity of the kidney tubules, collecting duct and surrounding interstitium, which collectively refine the blood and urine's electrolyte composition, body's fluid status, and produce hormones. "Intra-renal inflammation" refers to the presence of inflammatory cells within and surrounding each of the subcompartments described above within the nephrons.

Without being bound to a particular theory, kidney tubule health may be an indicator of chronic kidney disease or acute kidney injury. Accordingly, the present disclosure also provides methods of identifying a subject at risk for CKD, or a complication thereof. Exemplary complications of CKD are known in the art. See, for example, Levey et al., Am J Kidney Dis 53 (3): 522-535 (2009). In exemplary aspects, the complication of CKD is heart disease, cardiovascular disease, or death. In exemplary embodiments, the subject is on hypertension treatment. In exemplary embodiments, the method comprises measuring the level of at least two of the following in a urine sample obtained from the subject: (i) $\alpha$1m; (ii) KIM-1; and (iii) YKL-40; wherein the subject is at risk for CKD, or a complication thereof, when the levels are increased, relative to a control level. In some aspects, the subject is also determined as needing to discontinue or decrease the hypertension treatment when the levels are increased, relative to a control level. As used herein, "chronic kidney disease" or "CKD" which is also known as "chronic renal disease," refers to a progressive loss of kidney function over a period of months or years. With regard to the CKD of the methods of the present disclosure, the CKD may be any stage, including, for example, Stage 1, Stage 2, Stage 3, Stage 4, or Stage 5 (also known as established CKD, end-stage renal disease (ESRD), chronic kidney failure (CKF), or chronic renal failure (CRF)). The CKD may be caused by hypertension treatment and additionally, any one of a number of factors, including, but not limited to, acute kidney injury, causes of acute kidney injury, Type 1 and Type 2 diabetes mellitus leading to diabetic nephropathy, high blood pressure (hypertension), glomerulonephritis (inflammation and damage of the filtration system of the kidneys), polycystic kidney disease, use (e.g., regular and over long durations of time) of analgesics (e.g., acetaminophen, ibuprofen) leading to analgesic nephropathy, atherosclerosis leading to ischemic nephropathy, obstruction of the flow of urine by stones, an enlarged prostate strictures (narrowings), HIV infection, sickle cell disease, illicit drug (e.g., heroin, cocaine) abuse, amyloidosis, kidney stones, chronic kidney infections, and certain cancers.

Further provided are methods of determining a subject's need for treatment for chronic kidney disease (CKD), wherein the subject is on a hypertension treatment. The present disclosure provides methods of determining a subject's need for treatment for chronic kidney disease (CKD) during hypertension treatment. In exemplary embodiments, the method comprises measuring the level of at least two of the following in a urine sample obtained from the subject: (i) α1m; (ii) KIM-1; and (iii) YKL-40; wherein the subject needs treatment for CKD, when the levels are increased, relative to a control level. In some aspects, the subject is also determined as needing to discontinue or decrease the hypertension treatment when the levels are increased, relative to a control level.

The present disclosure provides methods of diagnosing a subject with a drug-induced kidney injury, wherein the subject is on a hypertension treatment. The present disclosure provides methods of diagnosing a subject with a drug-induced kidney injury during hypertension treatment. In exemplary embodiments, the method comprises measuring the level of at least two of the following in a urine sample obtained from the subject: (i) Alpha-1 microglobulin (α1m); (ii) kidney injury molecule (KIM-1); and (iii) Chitinase-3-like protein (YKL-40); wherein the subject has a drug-induced kidney injury when the levels are increased, relative to a control level. In some aspects, the subject is also determined as needing to discontinue or decrease the hypertension treatment when the levels are increased, relative to a control level. By "kidney injury" is meant any injury to the kidney caused by any one or more of: ischemia, exposure to a toxin, use of an angiotensin-converting enzyme inhibitor (ACEI) or angiotensin-II receptor blocker, a blood transfusion reaction, an injury or trauma to muscle, surgery, shock, hypotension, or any of the causes of acute renal failure (ARF) or CKD. The kidney injury may be an injury to any tissue found within the kidney, including, but not limited to, a tissue of the medulla, cortex, renal pyramid, interlobar artery, renal artery, renal vein, renal hilum, renal pelvis, ureter, minor calyx, renal capsule, inferior renal capsule, superior renal capsule, interlobar vein, nephron, major calyx, renal papilla, glomerulus, Bowman's capsule, and renal column, which tissue is sufficiently damaged to result in a partial or complete loss of function. The injured kidney tissue comprises any one or more of distinct cell types which occur in the kidney, including, but not limited to, glomerular parietal cells, endothelial cells and podocytes; intraglomerular mesangial cells; epithelial cells of Bowman's capsule; kidney proximal tubule brush border cells; loop of Henle thin segment cells and thick ascending limb cells; kidney distal tubule cells; kidney collecting duct cells; and cells within kidney interstitium. In certain embodiments of the invention, the kidney injury comprises injury to a kidney peritubular microvasculature. In certain aspects, the kidney injury comprises injury to a peritubular capillary. In some embodiments, the kidney injury comprises injury to tubule (tubular) epithelial cells and the kidney interstitium. The present disclosure also provides methods of determining whether a subject needs treatment for a drug-induced kidney injury, wherein the subject is on a hypertension treatment. The present disclosure also provides methods of determining whether a subject needs treatment for a drug-induced kidney injury during hypertension treatment. In exemplary embodiments, the method comprises measuring the level of at least two of the following in a urine sample obtained from the subject: (i) Alpha-1 microglobulin (α1m); (ii) kidney injury molecule (KIM-1); and (iii) chitinase-3-like protein (YKL-40); wherein the subject needs treatment for a drug-induced kidney injury when the measured levels are increased, relative to a control level. In exemplary aspects, the subject also should discontinue or decrease treatment with the hypertension medication when the levels are increased, relative to a control level.

In exemplary embodiments, the present disclosure provides a method of monitoring a subject during hypertension treatment. In various aspects, the method comprises measuring the level of at least two of the following in a urine sample obtained from the subject: (i) Alpha-1 microglobulin (α1m); (ii) kidney injury molecule (KIM-1); and (iii) Chitinase-3-like protein (YKL-40). In various instances, the measured levels are indicative the subject's kidney tubule health and thus is indicative of whether it is safe for the subject to continue on the hypertension treatment or whether modifications to the hypertension treatment are needed, and can be indicative of whether the subject is at risk for or needs treatment or increased monitoring for CKD or AKI, or complications thereof. In exemplary instances, the levels of at least two of (i) α1m; (ii) KIM-1; and (iii) YKL-40 are normalized to the level of urine creatinine and then compared to baseline levels of the corresponding marker which reflects the levels of the corresponding marker prior to starting the hypertension treatment. In exemplary aspects, the measuring step takes place about 2 weeks after the subject started the hypertension treatment. In aspects, the method comprises the step of measuring the baseline levels of the markers. In certain instances, the method comprises monitoring the levels of the markers during the course of treatment. In some instances, the monitoring comprises measuring at least two of (i) α1m; (ii) KIM-1; and (iii) YKL-40 about 3 months after the last measuring step. In this regard, the presently disclosed method comprises in some instances, measuring at least two of (i) α1m; (ii) KIM-1; and (iii) YKL-40 (A) prior to the subject starting the hypertension treatment, (B) about 2 weeks after the subject started the hypertension treatment, and (C) every 3 months from (B). In some aspects, (C) occurs provided that the hypertension treatment is deemed as providing blood pressure lowering effects to the subject such that the subject has a systolic blood pressure of less than 120 mmHg. In various aspects of the above, the subject should continue the hypertension treatment, when the levels of (i) α1m; (ii) KIM-1; and/or (iii) YKL-40 are decreased or unchanged, relative to a control level, and wherein the subject should discontinue or decrease treatment with the hypertension medication, when the levels of (i) α1m; (ii) KIM-1; and/or (iii) YKL-40 are increased, relative to a control level.

Measurement of Biomarker Levels

The methods of the present disclosure relate to measuring a level of a biomarker, e.g., a protein, a compound, a small molecule, in a sample obtained from a subject, e.g., a urine sample obtained from a subject. In exemplary aspects of the presently disclosed methods, the method comprises measuring the level of one of the following in a urine sample obtained from the subject: (i) α1m; (ii) KIM-1; or (iii) YKL-40. In exemplary aspects of the presently disclosed methods, the method comprises measuring the level of at least two of the following in a urine sample obtained from the subject: (i) α1m; (ii) KIM-1; and (iii) YKL-40. In exemplary aspects, the method comprises measuring the level of α1m and KIM-1. In alternative aspects, the method comprises measuring α1m and YKL-40. In other aspects, the method comprises measuring KIM-1 and YKL-40. In exemplary aspects, the method comprises measuring the level of α1m and KIM-1 and YKL-40.

In exemplary instances, the method further comprises measuring the level of at least one of the following in a urine sample obtained from the subject: (i) neutrophil gelatinase associated lipocalin (NGAL); (ii) uromodulin (UMOD); (iii) interleukin-18 (IL-18), (iv) beta-2 microglobulin (β2m); and (v) monocyte chemoattractant protein-1 (MCP-1). In some aspects, the method comprises measuring the level of at least 2, 3, or 4 of NGAL, UMOD, IL-18, β2m, and MCP-1. In some instances, the method comprises measuring the level of each of NGAL, UMOD, IL-18, β2m, and MCP-1.

In exemplary aspects, the method further comprises measuring the level of clusterin or trefoil factor-3 (TFF3) in a urine sample obtained from the subject. In some instances, the method comprises measuring the level of both clusterin and TFF3 in a urine sample obtained from the subject.

In exemplary aspects, the method further comprises measuring the level of at least one of the following in a blood sample obtained from the subject: (i) soluble tumor necrosis factor receptor-1 (sTNFR-1), (ii) soluble tumor necrosis factor receptor-2 (sTNFR-2), (iii) KIM-1, (iv) UMOD.

Such biomarkers are known in the art. The amino acid sequences of each are available at the website for the National Center for Biotechnology Information (see Table A), exemplary sequences of which are provided in the sequence listing submitted herewith.

TABLE A

| Gene name (abbreviation, full) | NCBI Gene ID No. | mRNA Accession | SEQ ID NO: | Protein Accession | SEQ ID NO: |
|---|---|---|---|---|---|
| Alpha-1 microglobulin (α1m); | 259 | NM_001633.3 | 1 | NP_001624.1 CAA38587.1 CAA38586.1 P02760.1 | 2 |
| uromodulin (UMOD) | 7369 | NM_001008389.2 XM_011545934.2 XM_011545935.1 XM_011545936.1 XM_011545937.1 XM_011545938.1 XM_011545940.2 XM_024450433.1 NM_003361.3 NM_001278614.1 | 3 | NP_001008390.1 XP_011544236.2 XP_011544237.1 XP_011544238.1 XP_011544239.1 XP_011544240.1 XP_011544242.2 XP_024306201.1 | 4 |
| Chitinase-3-like protein (YKL-40) | 1116 | NM_001276.2 NM_001025197.1 NM_001025199.1 XM_024452754.1 XM_024452753.1 XM_024452752.1 | 5 | NP_001267.2 NP_001020368.1 NP_001020370.1 XP_024308522.1 XP_024308521.1 XP_024308520.1 P36222.2 | 6 |
| neutrophil gelatinase associated lipocalin (NGAL) | 3934 | NM_005564.4 | 7 | NP_005555.2 CAA58127.1 AAB26529.1 P80188.2 ACD02429.1 | 8 |
| kidney injury molecule (KIM-1) | 26762 | NM_001173393.2 NM_001308156.1 NM_012206.3 XM_024446024.1 XM_024446023.1 XM_024446022.1 XM_024446021.1 XM_024446020.1 XM_024446019.1 XM_017009339.2 XM_011534515.2 | 9 | NP_001166864.1 Q96D42.2 NP_001295085.1 NP_036338.2 XP_024301792.1 XP_024301791.1 XP_024301790.1 XP_024301789.1 XP_024301788.1 XP_024301787.1 XP_016864828.1 XP_011532817.1 AAH13325.1 | 10 |
| Interleukin-18 (IL-18) | 3606 | NM_001243211.1 XM_011542805.1 XM_011542806.2 | 11 | NP_001230140.1 XP_011541107.1 XP_011541108.1 CAC01436.1 AAK95950.1 Q14116.1 | 12 |
| Beta-2 microglobulin (β2m) | 567 | NM_004048.3 XM_005254549.3 | 13 | NP_004039.1 XP_005254606.1 AAA51811.1 AAH64910.1 AAH32589.1 AAD14388.1 AAD14387.1 AAB25312.1 | 14 |

TABLE A-continued

| Gene name (abbreviation, full) | NCBI Gene ID No. | mRNA Accession | SEQ ID NO: | Protein Accession | SEQ ID NO: |
|---|---|---|---|---|---|
| Monocyte chemoattractant protein-1 (MCP-1) | 6347 | NM_002982.3 | 15 | CAA23830.1 BAA35182.1 AAD48083.1 NP_002973.1 AAB20651.1 BAA05080.1 CAC14049.1 P13500.1 | 16 |
| Cystatin C | 1471 | NM_000099.3 | 17 | NP_000090.1 | 1820 |
| Trefoil Factor 3 (TFF3) | 7033 | NM_003226.3 | 19 | NP_003217.3 AAL28111.1 BAB13731.1 AAH17859.1 | 20 |
| Clusterin (CLU) | 1191 | NM_001831.3 XM_006716284.3 | 21 | NP_001822.3 XP_006716347.1 | 22 |
| Albumin | 213 | NM_000477.6 | 23 | NP_000468.1 AAA61201.1 | 24 |
| Soluble TNFR-1 | 7132 | NM_001065.3 NM_001346091.1 NM_001346092.1 NM_001066.2 | 25 | NP_001056.1 P19438.1 NP_001333020.1 NP_001333021.1 NP_001057.1 AAH10140.1 AAM77802.1 AAN72434.1 | 26 |
| Soluble TNFR-2 | 7133 | NM_001066.2 | 27 | NP_001057.1 BAA89055.1 BAA89054.1 BAA89053.1 BAA89052.1 P20333.3 | 28 |

*some sequences provided represent the unprocessed, immature or preproprotein versions of the biomarker. Additional sequences are provided in Appendix Table 8.

In exemplary embodiments, the methods comprise measuring additional biomarkers not listed in Table A. In exemplary embodiments, the methods comprise measuring the level of at least one additional biomarker not listed in Table A. In exemplary instances, the methods comprise measuring the level of at least 2, 3, 4, 5 or more additional biomarkers not listed in Table A. In exemplary instances, the methods comprise measuring the level of at least 10, 15, 20 or more additional biomarkers not listed in Table A. In exemplary instances, the methods comprise measuring the expression level of at least 50, 100, 200 or more additional biomarkers not listed in Table A. In exemplary instances, the methods comprise measuring the level of a plurality of different biomarkers, in addition to one or more listed in Table A.

In alternative embodiments, the methods comprise measuring only one or more biomarkers in Table A. For example, the methods may comprise measuring only α1m, KIM-1, YKL-40, and optionally one or more biomarker listed in Table A.

Suitable methods of measuring levels of biomarkers, e.g., protein biomarkers, are known in the art and include (A) immunoassays (e.g., Western blotting, an enzyme-linked immunosorbent assay (ELISA), a radioimmunoassay (RIA), and immunohistochemical assay) or (B) bead-based multiplex assays, e.g., those described in Djoba Siawaya J F, Roberts T, Babb C, Black G, Golakai H J, Stanley K, et al. (2008) An Evaluation of Commercial Fluorescent Bead-Based Luminex Cytokine Assays. PLOS ONE 3(7):e2535. The immunoassay in some aspects measures each biomarker one at a time (e.g., sequentially). In other aspects, the immunoassay measures a combination of biomarkers simultaneously or concurrently. Assay formats include but are not limited to: ELISAs, chromatography, radioimmunoassays, mass spectroscopy, and protein-blotting methods. The immunoassay includes use of a binding agent (e.g., an antibody, antigen-binding fragment thereof, or related antibody-based molecule, or an aptamer) that binds specifically and with high affinity to the biomarker. The binding agent specific to each biomarker can be monoclonal or polyclonal.

In various aspects, the binding agent is conjugated or linked to a detectable label. When the binding agent binds to the biomarker, a biomarker-binding agent complex is formed and the complex in certain aspects is detectable, measureable and/or quantifiable using detectable labels, such as, e.g., fluorophores, chromophores, electrochemical or electrochemiluminescent labels), substrates for enzymatic reactions. In various aspects, the complex is detectable, measureable and/or quantifiable by virtue of a secondary binding agent which is conjugated or linked to a detectable label.

The immunoassays may utilize sandwich, competitive or non-competitive assay formats to generate a signal that is related to presence or quantity of the biomarker of interest. In the case of sandwich immunoassays, such reagents can also include one or more detectably labeled binding agents (e.g., antibodies), the detectably labeled binding agent comprising a binding agent that detects the intended biomarker target(s) bound to a detectable label. The binding agents (e.g., antibodies) may be embedded in solid structures alone or in combination. Solid structures include membrane filters, cellulose-based papers, beads (e.g. polymeric, latex), glass, silicone wafers, microassay systems, nanoassay systems, resins, gels, or multiple-well plates. An assay strip could be prepared by coating the antibody (or antibodies) in an array on a solid structure. This strip in some aspects is dipped into the test sample (e.g., urine sample) and then processed quickly through washes and detection steps to generate a measurable signal, such as a colored spot. Antibodies or other polypeptides may be bound to specific zones of assay devices either by conjugating directly to an assay device surface, or by indirect binding. In an example of the latter case, antibodies or other polypeptides may be immobilized on assay systems or other solid supports, and that solid support immobilized to the device surface.

The signal generated from conjugation of the protein-binding agent-label can be detected using various methods, including optical, acoustical, and electrochemical methods. Examples of detection modes include fluorescence, radio-chemical detection, reflectance, absorbance, amperometry, conductance, impedance, interferometry, ellipsometry, and mobile phone technology, etc. In some of these methods, the solid phase binding agent (e.g., antibody) is coupled to a transducer that is spatially separate from the solid phase binding agent (e.g., antibody) (e.g., a fluorometer that employs an excitation light source and an optical detector). Antibody-based biosensors may also be used to determine the presence or quantify the amount of biomarkers that optionally eliminate the need for a labeled molecule.

Alternative assays can include use of receptors for a particular target, aptamers, etc.

Mass spectrometry and/or light spectroscopy may be used to measure the level of the biomarkers described herein. Methods of measuring levels of proteins using light spectroscopy are known in the art (see, e.g., Porterfield et al., Virology 407 (2): 281-288 (2010)). Suitable methods of measuring protein levels are described herein. See the section entitled EXAMPLES.

In exemplary aspects, the methods of the present disclosure comprise simultaneously measuring the level of α1m, KIM-1, and YKL-40 proteins in the urine of subjects via, e.g., multiplex immunoassays. In exemplary aspects, the methods of the present disclosure comprise simultaneously measuring multiple levels in the urine sample. For example, the method in some aspects, comprises simultaneously measuring the level of KIM-1 and YKL-40 proteins in the urine of subjects via multiplex immunoassays and measuring the level of α1m via a nephelometer assay. Other suitable methods for determining levels of protein biomarkers comprises the Meso Scale Discovery® (MSD) method of multiplexing in multi-well plate combined with electrochemiluminescence for detection as essentially described in Kuster et al., J Vis Exp 78:50786 (2013); doi: 10.3791/50786 and Oh et al., J Alzheimers Dis 21 (3): 769-773 (2010).

In some aspects, the measurement of biomarkers comprises nephelometry, which is a technique that detects proteins in liquid samples. In nephelometry, forwarded scattered light is measured when a laser beam passes through a sample and the light is deflected by the proteins. See, e.g., Deaton et al., Clin Chem 22 (9): 1465-1471 (1976). In exemplary aspects, α1m and/or cystatin C are measured via nephelometry. Such immunoassays and nephelometer assays are known in the art but also described herein in EXAMPLES.

Once the level of α1m, KIM-1, and/or YKL-40 is measured from the urine sample obtained from the subject, the measured level may be compared to a control level, normalized to a housekeeping protein, indexed to measures of urine concentration (e.g. indexed to urine creatinine or urine osmolality), or mathematically transformed. For example, the method comprises measuring the level of creatinine in the urine sample and adjusting each biomarker level to the level of urine creatinine. In exemplary instances, the measured level is adjusted to the measured level of urine creatinine of the urine sample.

Control Levels

In some aspects of the methods described herein, the level that is measured may be the same as a control level, e.g., a reference level or a cut off level or a threshold level, or may be increased or decreased relative to a control level, e.g., reference level or a cut off level or a threshold level. In some aspects, the control level is that of a control subject which may be a matched control of the same species, gender, ethnicity, age group, smoking status, body mass index (BMI), current therapeutic regimen status, medical history, or a combination thereof, but differs from the subject being diagnosed or from whom a sample was obtained in that the control subject does not suffer from the disease in question or is not at risk for the disease. Thus, in exemplary aspects, the control level(s) of the biomarker(s) is/are level(s) of a subject known to not have hypertension. In alternative aspects, the control level(s) of the biomarker(s) is/are level(s) of a subject known to have hypertension. In exemplary aspects, as further described herein, the measured level is compared to both a control level of a subject known to not have hypertension and a control level of a subject known to have hypertension. In exemplary aspects, the control level is the mean of a population's levels for the corresponding biomarker. For example, in exemplary aspects, the measured level of α1m is compared to a control level of α1m which is the mean level of α1m levels of a population of subjects who do not have hypertension. In some aspects, the measured level of α1m is compared to a control level of α1m which is the mean level of α1m levels of a population of subjects who have hypertension but have not been treated for hypertension. In exemplary aspects, the control level is the baseline level for the subject, e.g., the level taken prior to starting hypertension treatment. In exemplary aspects, the control level is the level taken prior to starting a first or new hypertension treatment. In exemplary aspects, the control level is the level taken prior to starting a modified hypertension treatment (e.g., modified with respect to the first, current, or previous hypertension treatment).

In exemplary aspects, the control levels are normalized to a reference measurement to account for the degree of urine concentration. In some aspects, the control level is normalized to the level of creatinine (or osmolality or specific gravity) in the urine sample and adjusting each control level (for each biomarker) to the level of urine creatinine (or urine osmolality or urine specific gravity). In exemplary aspects, the control level of α1m, KIM-1, and/or YKL-40 if measured in a urine sample is normalized to a housekeeping protein or indexed to measures of urine concentration (e.g. indexed to urine creatinine or urine osmolality). For example, the control level is normalized to the level of creatinine in the urine sample and expressed as a level relative to the level of urine creatinine. In other instances, the control level is indexed to urine osmolality.

Relative to a control level, the level that is measured or determined may be increased. As used herein, the term "increased" with respect to level refers to any % increase above a control level. The increased level may be at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is measured or determined may be decreased. As used herein, the term "decreased" with respect to level (e.g., expression level) refers to any % decrease below a reference level. The decreased level may be at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

Relative to a control level, the level that is measured or determined may be essentially the same or unchanged. In some instances, the unchanged level is within about +20% of the control level, +15% of the control level, +10% of the control level, +9% of the control level, +8% of the control level, +7% of the control level, +6% of the control level, +5% of the control level, +4% of the control level, +3% of the control level, +2% of the control level, or +1% of the control level.

Hypertension Treatments

As used herein, the term "treatment" is meant "therapeutic treatment" or "therapy" or "treatment regimen" or "treatment modality". A "hypertension treatment" refers to any "therapeutic treatment" or "therapy" or "treatment regimen" or "treatment modality" purposed for lowering blood pressure. The hypertension treatment in various aspects comprises a hypertension medication. In other aspects, the hypertension treatment comprises a combination of more than one hypertension medication. For purposes herein, a hypertension treatment may be described in terms of the hypertension medication(s) and the doses (and frequency) for each. To continue a hypertension treatment refers to remaining on the same hypertension medication or combination of hypertension medications at the prescribed dose(s) and frequency or frequencies. To discontinue a hypertension treatment means to stop a hypertension medication or combination of hypertension medications at the prescribed dose(s) and frequency or frequencies. Discontinuing a hypertension treatment may be the discontinuation of all hypertension treatments (e.g., hypertension medications) or may be the stopping of one hypertension treatment and the starting of a different or modified hypertension treatment. To decrease a hypertension treatment means to reduce the dose(s) and/or frequency or frequencies of the hypertension medication or combination of hypertension medications, or to remove one or more hypertension medications from the combination of hypertension medications. To increase a hypertension treatment means to increase the dose(s) and/or frequency or frequencies of the hypertension medication or combination of hypertension medications, or to add one or more hypertension medications to the existing hypertension medication(s) of the treatment.

As used herein, the term hypertension medication refers to any one or a combination of the following medications used to lower high blood pressure in a subject: a diuretic, a beta blocker, an ACE inhibitor, an angiotensin II receptor blocker, a calcium channel blocker, an alpha blocker, an alpha-2 receptor agonist, a central agonist, a renin inhibitor, an arterial vasodilator, and the like. In some aspects, the diuretic is any drug that increases urination to reduce sodium and fluid in the body. In various instances, the diuretic is a thiazide diuretic, e.g., hydrochlorothiazide (Dyazide). In some aspects, the diuretic is bumetanide, chlorthalidone, chlorothiazide, ethacrynate, furosemide, hydrochlorothiazide (HCTZ, Esidrix, Hydrodiuril, Microzide), indapamide, methclothiazide, metolazone, torsemide, amiloride, spironolactone, eplerenone, triamterene, or amiloride. In exemplary aspects, the beta blocker is any that act directly on the heart to reduce heart rate, force of pumping, and blood volume. In some aspects, the beta blocker is acebutolol, atenolol, bisoprolol fumarate, carvedilol, esmilol, labetalol, metoprolol, nadolol, nebivolol, penbutolol sulfate, propranolol, or sotalol. In some aspects, the ACE inhibitor is benazepril, captopril, enalapril maleate, fosinopril, lisinopril, moexipril, perindopril, quinapril, ramipril, or trandolapril. In some instances, the angiotensin II receptor blocker is azilsartan, candesartan, eprosartan mesylate, irbesartan, losartan, olmesarten, telmisartan, or valsartan. In some instances, the calcium channel blocker is amlodipine, clevidipine, diltiazem, felodipine, isradipine, nicardipine, nifedipine, nimodipine, nisoldipine, or verapamil. In some regards, the alpha blocker is doxazosin, prazosin, or terazosin. In certain aspects, the alpha-2 receptor agonist is methyldopa. In certain aspects, the central agonist is clonidine or guanfacine. In some instances, the hypertension medication is a renin inhibitor, such as aliskiren. In some instances, the hypertension medication is a peripheral adrenergic inhibitor, such as hyanadrel, guanethidine, or reserpine. In certain instances, the vasodilator is minoxidil or hydralazine.

In some aspects, the hypertension medication is a combination therapy comprising more than one of a diuretic, a beta blocker, an ACE inhibitor, an angiotensin II receptor blocker, a calcium channel blocker, an alpha blocker, an alpha-2 receptor agonist, a central agonist, a renin inhibitor, and/or an arterial vasodilator. Common combinations include, for instance, valsartan and HCTZ, olmesartan and amlodipine, lisinopril and furosemide, lisinopril and HCTZ, metoprolol and HCTZ, atenolol and chlorthalidone, as well as triamterene and HCTZ.

CKD Treatment

A "CKD treatment" or "chronic kidney disease treatment" refers to any "therapeutic treatment" or "therapy" or "treatment regimen" or "treatment modality" purposed for treating chronic kidney disease. The CKD treatment in various aspects comprises medications to control blood glucose or proteinuria. In other aspects, the CKD treatment comprises treatment regimen or strategy specific for the underlying cause, e.g. glucocorticoid steroids for lupus nephritis, placement of a percutaneous nephrostomy tube to alleviate urinary tract obstruction. In other aspects, CKD treatment comprises a combination of more than one CKD medication or treatment regimen.

Samples

The samples of the methods of the present disclosure are samples obtained from a subject. In some embodiments, the sample comprises a bodily fluid, including, but not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In preferred instances, the sample is a urine sample obtained from the subject.

In some aspects, the samples are frozen or cryopreserved samples. In some aspects, the samples are directly obtained from the subject and/or are not frozen or cryopreserved.

In some aspects, the samples are pre-processed in laboratory prior to measuring biomarkers. In some aspects, the samples are refrigerated at about 2 to about 8 degrees C. and centrifuged (e.g., 1000 g at 4 degrees C. for about 10 minutes) to, e.g., separate the urine supernatant from cells and/or cellular debris within the urine.

Subjects

In exemplary aspects, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human.

In exemplary aspects, the subject has hypertension (e.g., Stage 1 hypertension or Stage 2 hypertension) or high blood pressure or elevated blood pressure e.g., a blood pressure of 120 mmHg or higher. In exemplary instances, the subject is in a state of hypertensive crisis. In exemplary aspects, the subject is one who has elevated of high blood pressure (e.g., systolic blood pressure of 120 mmHg or higher) and thus, the subject is one who needs a hypertension treatment. In some aspects, the subject has high blood pressure, because the subject is not on any hypertension treatment or has never been on any hypertension treatment before or because the subject is one who is on a hypertension treatment which is not effective (or no longer effective) at treating the hypertension in the subject and requires a new, modified hypertension treatment. In exemplary instances, the subject is not on any hypertension treatment (not taking any hypertension medications) and/or the subject has never been on any hypertension treatment before (never taken any hypertension medications). In some aspects, the subject is on a hypertension treatment which is not effective (or no longer effective) at treating the hypertension in the subject and requires a new, modified hypertension treatment. In some aspects, the subject is on a hypertension treatment (e.g., taking one or more hypertension medications). In some aspects, the subject is not on a hypertension treatment (e.g., not taking one or more hypertension medications).

In some aspects, the human is an adult aged 18 years or older, optionally, aged 40, 50, or 60 years or older. In some aspects, the human is a female adult. In some instances, the human is a male adult. In certain aspects, the human adult is African American, Caucasian, or Hispanic. In some instances, the human adult is of a race other than African American, Caucasian, and Hispanic, e.g., Asian or Pacific Islander. In some aspects, the human is a child aged 17 years or less. In exemplary aspects, the subject has a metabolic disease, e.g., diabetes, obesity. In some aspects, the subject has a body mass index (BMI) of about 26 or greater, e.g., 26, 27, 28, 29, 30, 31, 32, 33, 34, 35, or more. In exemplary aspects, the subject has one or more baseline characteristics listed in Table 1. For example, the subject has an estimated GFR (eGFR) greater than or about 60.

Additional Steps

With regard to the methods of the invention, the methods may include additional steps. For example, the method may include repeating one or more of the recited step(s) of the method. Accordingly, in exemplary aspects, the method comprises measuring a level of the biomarker in a sample obtained from a subject and re-measuring the level, e.g., at a different time point, e.g., for accuracy, for monitoring risk of CKD, for determining the need for change in hypertension treatment.

In exemplary aspects, the method comprises taking a baseline measurement of one or more biomarkers to establish a reference or control level specific to the subject. In exemplary aspects, the method comprises measuring one or more of $\alpha$1m, KIM-1, and/or YKL-40 prior to starting a hypertension treatment. In exemplary instances, the method comprises diagnosing the subject with hypertension (e.g., measuring blood pressure of the subject) and then measuring one or more (e.g., at least two) of $\alpha$1m, KIM-1, and/or YKL-40 prior to starting a hypertension treatment to establish a reference or control level specific to the subject. In some aspects, the method comprises re-measuring the levels of one or more (e.g., at least two) of $\alpha$1m, KIM-1, and/or YKL-40 after the subject started a hypertension treatment. For example, the method comprises re-measuring the levels of one or more (e.g., at least two) of $\alpha$1m, KIM-1, and/or YKL-40 at least or about 2 weeks after the subject started a hypertension treatment. In exemplary aspects, the method comprises re-measuring the levels of one or more (e.g., at least two) of $\alpha$1m, KIM-1, and/or YKL-40 once a month, 2× per month, 3× per month, 4× per month or more frequently. In exemplary aspects, the levels are re-measured once a year, once a quarter, 2× per year, 3× per year, 4× per year or more frequently. In exemplary aspects, the method comprises re-measuring the levels of one or more (e.g., at least two) of $\alpha$1m, KIM-1, and/or YKL-40 every 2 weeks, every 4 weeks, every 6 weeks, every 9 weeks, or every 12 weeks after the time at which the hypertension treatment started. In exemplary aspects, the method comprises re-measuring the levels of one or more (e.g., at least two) of $\alpha$1m, KIM-1, and/or YKL-40 every 2 weeks, once a month, every 2 months, every 3 months, or every 4 months after the time at which the hypertension treatment started. In some instances, the method comprises measuring the levels of one or more (e.g., at least two) of $\alpha$1m, KIM-1, and/or YKL-40 about 2 weeks after the subject started a new or modified hypertension treatment (e.g., a new dose, a new combination of medications, a new medication), relative to the prior hypertension treatment. In some aspects, the method comprises measuring the levels of one or more (e.g., at least two) of $\alpha$1m, KIM-1, and/or YKL-40 before starting a first hypertension treatment, re-measuring about 2 weeks after starting the first hypertension treatment, and re-measuring about every 3 months, provided that the first hypertension treatment is deemed effective at treating hypertension. If the subject switches from the first hypertension treatment to a second hypertension treatment which differs from the first hypertension treatment, the method in some aspects comprises re-measuring about 2 weeks after starting the second hypertension treatment, and re-measuring about every 3 months, provided that the second hypertension treatment is deemed effective at treating hypertension. In exemplary aspects, the levels are re-measured on a regular basis based on the analysis of the first re-measurement. In exemplary aspects, the levels are re-measured on a regular basis until a pre-determined goal is met. In exemplary aspects, the pre-determined goal is successful treatment or management of hypertension through the hypertension treatment. In exemplary instances, the methods comprise monitoring the subject during the hypertension treatment.

In exemplary aspects, the measured levels are first normalized to a reference measurement to account for the degree of urine concentration. In some aspects, the method comprises measuring the level of creatinine (or osmolality or specific gravity) in the urine sample and adjusting each biomarker level to the level of urine creatinine (or urine osmolality or urine specific gravity).

In exemplary aspects, the method comprises obtaining the sample from the subject, e.g., obtaining a urine sample from the subject. In exemplary embodiments, more than one sample is obtained from the subject. In exemplary embodiments, 2, 3, 4, 5, 6, 7, 8, 9, 10, or more samples are obtained from the subject, each sample obtained at a different point in time. In exemplary aspects, a sample is obtained from the subject once a week, once a month, 2× per month, 3× per month, 4× per month or more frequently. In exemplary aspects, a sample is obtained from the subject once a year, once a quarter, 2× per year, 3× per year, 4× per year or more frequently. In exemplary aspects, a sample is obtained on a regular basis based on the analysis of a first sample. In exemplary aspects, a sample is obtained on a regular basis until a pre-determined goal is met. In exemplary aspects, the pre-determined goal is the determination of whether the subject should continue with the hypertension medication. In exemplary instances, the methods comprise monitoring the subject during treatment.

In exemplary aspects, the method comprises measuring a level for every sample obtained. In exemplary aspects, the level is measured within 1, 4, 6, 8, 12, 16, or 24 hours of obtaining the sample. In exemplary aspects, the urine sample is centrifuged, and the urine supernatant is frozen or cryopreserved, and the level of the sample is determined at a later time.

In exemplary aspects, the methods comprise processing the sample for measurement. For example, the methods may comprise contacting the urine sample with a combination of binding agents, e.g., antibodies, or antigen binding fragments thereof.

In exemplary aspects, the method comprises measuring levels in the sample in more than one way. In exemplary instances, the methods comprise measuring biomarker(s) level(s) using a multiplex immunoassay and a nephelometer assay. In exemplary aspects, the method comprises measuring the levels of additional markers. For example, the method further comprises measuring the level of urine biomarkers which are associated with kidney injury or kidney disease. In exemplary aspects, the method further comprises measuring the level of creatinine in the subject. Creatinine, also known as 2-amino-1-methyl-5H-imidazol-4-one, 2-amino-1-methyl-1H-imidazol-4-one, or 2-amino-1-methylimidazol-4-ol, and identified by CAS number 60-27-5, is a chemical waste molecule generated from creatine. Creatinine is transported through the bloodstream to the kidneys. The kidneys filter creatinine out of the blood into urine for disposal. The kidneys therefore help to maintain the blood levels of creatinine within a normal range. Elevated blood creatinine levels could signify impaired kidney function or kidney disease. See, e.g., www.medicinenet.com/creatinine_blood_test/article.htm#what_is_creatinine). In certain aspects, the methods of the present disclosure comprises measuring serum or blood levels of creatinine. In some aspects, other blood biomarkers are measured, e.g., sTNFR-1, STNFR-2, KIM-1, UMOD. In certain aspects, the method comprises measuring urine creatinine levels (e.g., creatinine levels in the urine of a subject). In additional aspects, the method comprises adjusting each biomarker level (level of α1m, KIM-1, YKL-40, NGAL, UMOD, IL-18, β2m, MCP-1) to the level of urine creatinine, urine osmolality or urine specific gravity. In some aspects, the method further comprises determining the subject's urine albumin:urine creatinine ratio (ACR). Methods of determining ACR are known in the art and include those described in, for example, Fisher et al., Am J Kidney Dis 62(6): doi: 10.1053/ j.ajkd.2013.07.013; and Urquidi et al., PLOS One 7(5): e37797. In exemplary aspects, the method further comprises measuring the level of cystatin C in the subject, optionally, in serum or plasma obtained from the subject. In some aspects, the cystatin C is measured by an immunoassay such as nephelometry or article-enhanced turbidimetry. Suitable methods for measuring cystatin C are described in the art. See, e.g., Erlandsen et al., Scand J Clin Lab Invest 59 (1): 1-8 (1999). In some aspects, the method further comprises determining the subject's estimated glomerular filtration rate (eGFR). This assay estimates how much blood passes through the glomeruli (tiny filters in the kidney) each minute.

In exemplary aspects, the presently disclosed methods are carried out in combination with clinical data (e.g., a physical examination) of a subject. For instance, the methods may further comprise an assessment of the subjects' overall health and medical condition, including, e.g., an assessment of the subject's demographic information [e.g., age, sex, race], sociobehavioral risk factors [e.g. smoking, alcohol use, illicit drug use, etc.]), co-morbid conditions (e.g. diabetes, coronary artery disease, obesity, etc.), other laboratory results [e.g. serum albumin, etc.], concurrent medications, or a combination of any of the foregoing.

In exemplary aspects, the methods comprise administering treatment to a subject. Thus, methods of treatment are provided, as described below.

Methods of Treatment

The present disclosure provides methods of treating a subject with hypertension. As used herein, the term "hypertension" is synonymous with elevated high blood pressure and is defined as systolic blood pressure of 120 mmHg or higher. The guidelines provided by the American Heart Association AHA relating to blood pressure are provided below:

|  | Systolic (mmHg) | Diastolic (mmHg) |
|---|---|---|
| Normal blood pressure | Less than 120 | Less than 80 |
| Elevated | Between 120 and 129 | Less than 80 |
| Stage 1 hypertension | Between 130 and 139 | Between 80 and 89 |
| Stage 2 hypertension | At least 140 | At least 90 |
| Hypertensive crisis | Over 180 | Over 120 |

MacGill, Markus, "Everything you need to know about hypertension" Medical News Today, www.medicalnewstoday.com/articles/150109.php Accordingly, the present disclosure provides methods of treating a subject with high blood pressure, e.g., a systolic blood pressure of 120 mmHg or higher.

In exemplary embodiments, the methods of treating comprise (a) administering to the subject a hypertension treatment; (b) measuring the level of at least two of the following in a urine sample obtained from the subject: (i) α1m; (ii) KIM-1; and (iii) YKL-40; and (c) continuing the hypertension treatment, when the levels are decreased or unchanged, relative to a control level, e.g., baseline level, or discontinuing or decreasing the hypertension treatment, when the levels are increased, relative to a control level.

In exemplary embodiments, the subject is on a hypertension treatment and the method comprises (A) continuing the hypertension treatment, when the levels of at least two of (i) α1m, (ii) KIM-1, and (iii) YKL-40, are decreased or unchanged in a urine sample obtained from the subject, relative to a control level, e.g., baseline level, or (B) discontinuing or decreasing the hypertension treatment, when the levels of at least two of (i) α1m, (ii) KIM-1, and (iii)

YKL-40, are increased in a urine sample obtained from the subject, relative to a control level.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating a subject with a hypertension regimen of the present disclosure can provide any amount or any level of treatment. Furthermore, the treatment provided by the method of the present disclosure can include treatment of one or more conditions or symptoms or signs of the hypertension being treated. Signs of hypertension include several readings of high blood pressure over time. Symptoms of hypertension include but are not limited to headache, blurry vision, shortness of breath, sweating, anxiety, sleeping problems, and blushing.

Also, the treatment provided by the methods of the present disclosure can encompass slowing the progression of the condition or preventing new symptoms associated with the condition. For example, because unmanaged hypertension can lead to a heart attack, stroke and death, the methods can treat the hypertension by virtue of preventing the occurrence of a heart attack, stroke or death. In exemplary aspects, the methods treat by way of delaying the onset or recurrence of a heart attack or stroke by at least 1 day, 2 days, 4 days, 6 days, 8 days, 10 days, 15 days, 30 days, two months, 3 months, 4 months, 6 months, 1 year, 2 years, 3 years, 4 years, or more. In exemplary aspects, the methods treat by way increasing the survival of the subject or by delaying death of the subject. In some aspects, the method of treating encompasses a method of prophylactically treating (i.e., preventing) or delaying the onset of a disease.

In exemplary aspects, the methods of treating comprise taking a baseline measurement of the one or more biomarkers ($\alpha$1m, KIM-1, and/or YKL-40) to establish a reference or control level specific to the subject. In exemplary aspects, the method comprises measuring one or more of $\alpha$1m, KIM-1, and/or YKL-40 prior to starting a hypertension treatment. In exemplary aspects, the measured levels are normalized to a reference protein, e.g., creatinine in the urine. In some aspects, the method comprises measuring the level of creatinine in the urine sample and adjusting each biomarker level to the level of urine creatinine.

In various aspects, the subject has yet to be diagnosed with hypertension and has yet to start a hypertension treatment. In exemplary instances, the method comprises (A) diagnosing the subject with hypertension (e.g., measuring blood pressure of the subject) or determining the subject has a need for a hypertension treatment and (B) measuring one or more (e.g., at least two) of $\alpha$1m, KIM-1, and/or YKL-40 prior to starting a hypertension treatment to establish a reference or control level specific to the subject. In exemplary aspects, the presently disclosed methods of treating hypertension comprise starting the subject on a hypertension treatment and measuring at least two of $\alpha$1m, KIM-1, and YKL-40 of a urine sample obtained from the subject. Optionally, the measuring step occurs about 2 or about 3 weeks after starting the hypertension treatment. Optionally, the measuring step is repeated about 2 or about 3 weeks following the first measuring step (e.g., about 4 to about 6 weeks after starting the hypertension treatment), though, in some aspects, e.g., when the hypertension treatment is deemed effective at treating (e.g., managing) the hypertension, then the repeated measuring step(s) may occur less frequently than every 2 weeks or every 3 weeks, e.g., every month, every 2 months, every 3 months, every 4 months, or ever 6 months. In exemplary aspects, the measuring step occurs every 3 months during the course of hypertension treatment. In various embodiments, the methods of treatment comprising repeated and/or regular measuring of at least two of $\alpha$1m, KIM-1, and YKL-40 of a urine sample obtained from the subject achieve the monitoring of (i) risk for acute kidney injury or CKD or (ii) kidney tubule health, during hypertension treatment.

Kits

The present disclosure also provides kits comprising a binding agent specific for $\alpha$1m and a binding agent specific for KIM-1; or a binding agent specific for $\alpha$1m and YKL-40 or a binding agent specific for KIM-1 and a binding agent specific for YKL-40. In some aspects, the kit comprises a binding agent specific for $\alpha$1m and a binding agent specific for KIM-1 and a binding agent specific for YKL-40. The kit in some aspects further comprises a binding agent for one of NGAL, UMOD, IL-18, $\beta$2m, and MCP-1. In some aspects, the kit comprises a plurality of binding agents, each specific for one of NGAL, UMOD, IL-18, $\beta$2m, and MCP-1. In some aspects, the kit comprises a binding agent specific for $\alpha$1m, a binding agent specific for KIM-1, and a binding agent specific for YKL-40, and at least one or two or more of: a binding agent specific for NGAL, a binding agent specific for UMOD, a binding agent specific for IL-18, a binding agent specific for $\beta$2m, and a binding agent specific for MCP-1. Optionally, the kit comprises a binding agent for clusterin and/or a binding agent for TFF3. Optionally, the kit comprises a binding agent for sTNFR-1 and/or a binding agent for STNFR-2. In various aspects, the kit comprises all of these binding agents. In some aspects, the kit comprises each binding agent in a separate container. In other aspects, the kit comprises a mixture of at least two of said binding agents. With regard to the foregoing, the binding agent in some aspects is an antibody, antigen binding fragment, an aptamer, a protein or peptide substrate, or a nucleic acid probe. In exemplary aspects, the binding agent is an antibody, or antigen-binding fragment thereof. Such binding agents are known in the art. In some aspects, the kit comprises a collection of binding agents, e.g., a collection of antibodies, a collection of nucleic acid probes, each binding agent of which specifically binds to genes or nucleic acids encoding the biomarker or proteins. In some aspects, the collection of nucleic acid probes is formatted in an array on a solid support In various aspects, the solid support is a membrane filter, a cellulose-based paper, a bead (e.g. comprising polymeric, latex), glass, a silicone wafer, a micropartice, a nanoparticle, a resin, a gel, or a multiple-well plate. In some aspects, the kit comprises a multi-well microtiter plate, wherein each well comprises an antibody having a specificity which is unique to the antibodies of the other wells. In some aspects, the kit comprises a collection of substrates which specifically react with a marker. In some aspects, the kit comprises a multi-well microtiter plate, wherein each well comprises a substrate having a specificity which is unique to the substrates of the other wells. In various aspects, the kit comprises an assay system comprising a solid support comprising each of the binding agents at a unique location (e.g., a unique position or zone) on the solid support.

The binding agents in exemplary instances are bound to a detectable label or the kit includes a secondary binding agent that binds to the binding agents specific to the biomarker which secondary binding agent is bound to a detectable label. The kit in various aspects, includes such secondary binding agents, optionally bound to a detectable label. In some aspects, the kit further comprises additional reagents for washing the solid support or detecting the detectable label. Additional components of the kit in some instances include a device for detecting the detectable label through measurement of optical, acoustical, and electrochemical signals.

In some aspects, the kits further comprise instructions for use. In some aspects, the instructions are provided as a paper copy of instructions, an electronic copy of instructions, e.g., a compact disc, a flash drive, or other electronic medium. In some aspects, the instructions are provided by way of providing directions to an internet site at which the instructions may be accessed by the user.

In some aspects, the kits further comprise a unit for a collecting a urine or blood sample, e.g., any of the samples described herein, of the subject. In some aspects, the unit for collecting a sample is a vial, a beaker, a tube, a microtiter plate, a petri dish, and the like.

Assay Systems

The present disclosure provides an assay system useful for measuring the biomarkers described herein. In exemplary embodiments, the assay system allows for the simultaneous measurement of multiple biomarkers. In exemplary aspects, the assay system is a lateral flow assay system. In exemplary aspects, the assay system is an immunochromatographic assay system. Lateral flow assay systems are known in the art. See, e.g., Grant et al., Vaccine 34 (46): 5656-5663 (2016); and Cross et al., J Infect Dis 214 (suppl3): S210-S217 (2016).

In exemplary aspects, the assay system of the present disclosure comprises one or more solid supports (e.g., membranes or papers or filters) comprising one or more binding agents, e.g., antibodies, antigen binding fragments, aptamers, and/or the like, specific for the biomarkers described herein. The presently disclosed assay system comprises a binding agent specific for α1m and a binding agent specific for KIM-1; or a binding agent specific for α1m and YKL-40 or a binding agent specific for KIM-1 and a binding agent specific for YKL-40. In some aspects, the assay system comprises a binding agent specific for α1m and a binding agent specific for KIM-1 and a binding agent specific for YKL-40. The assay system in some aspects further comprises a binding agent for one of NGAL, UMOD, IL-18, β2m, and MCP-1. In some aspects, the assay system comprises a plurality of binding agents, each specific for one of NGAL, UMOD, IL-18, β2m, and MCP-1. In some aspects, the assay system comprises a binding agent specific for α1m, a binding agent specific for KIM-1, and a binding agent specific for YKL-40, and at least one or two or more of: a binding agent specific for NGAL, a binding agent specific for UMOD, a binding agent specific for IL-18, a binding agent specific for β2m, and a binding agent specific for MCP-1. Optionally, the assay system comprises a binding agent for clusterin and/or a binding agent for TFF3. Optionally, the assay system comprises a binding agent for sTNFR-1 and/or a binding agent for sTNFR-2. In various aspects, the assay system comprises all of these binding agents. With regard to the foregoing, the binding agent in some aspects is an antibody, antigen binding fragment, an aptamer, a protein or peptide substrate, or a nucleic acid probe. In exemplary aspects, the binding agent is an antibody, or antigen-binding fragment thereof. In some aspects, the assay system comprises a collection of binding agents, e.g., a collection of antibodies, a collection of nucleic acid probes, each binding agent of which specifically binds to the biomarker or proteins. In some aspects, the collection of binding agents is formatted in an array on a solid support. In various aspects, the solid support is a membrane filter, a cellulose-based paper, a bead (e.g. comprising polymeric, latex), glass, a silicone wafer, a microparticle, a nanoparticle, a resin, a gel, or a multiple-well plate. In some aspects, the assay system comprises a multi-well microtiter plate, wherein each well comprises an antibody having a specificity which is unique to the antibodies of the other wells. In some aspects, the assay system comprises a collection of substrates which specifically react with a marker. In some aspects, the assay system comprises a multi-well microtiter plate, wherein each well comprises a substrate having a specificity which is unique to the substrates of the other wells. In various aspects, the assay system comprises a solid support comprising each of the binding agents at a unique location (e.g., a unique position or zone) on the solid support.

The binding agents in exemplary instances are bound to a detectable label or the assay system comprises a secondary binding agent that binds to the binding agents specific to the biomarker which secondary binding agent is bound to a detectable label. The assay system in various aspects, includes such secondary binding agents, optionally bound to a detectable label. In some aspects, the assay system further comprises additional reagents for washing the solid support or detecting the detectable label. Additional components of the kit in some instances include a device for detecting the detectable label through measurement of optical, acoustical, and electrochemical signals.

In exemplary aspects, the assay system comprises binding agents conjugated to fluorescently-labeled microassay systems embedded on a conjugate pad. In exemplary aspects, the assay system comprises an application pad, a reagent pad, a detector binding agent, a capture antibody, a capture line, a control line, a membrane (e.g., nitrocellulose membrane) and an absorption pad.

Figure 2:
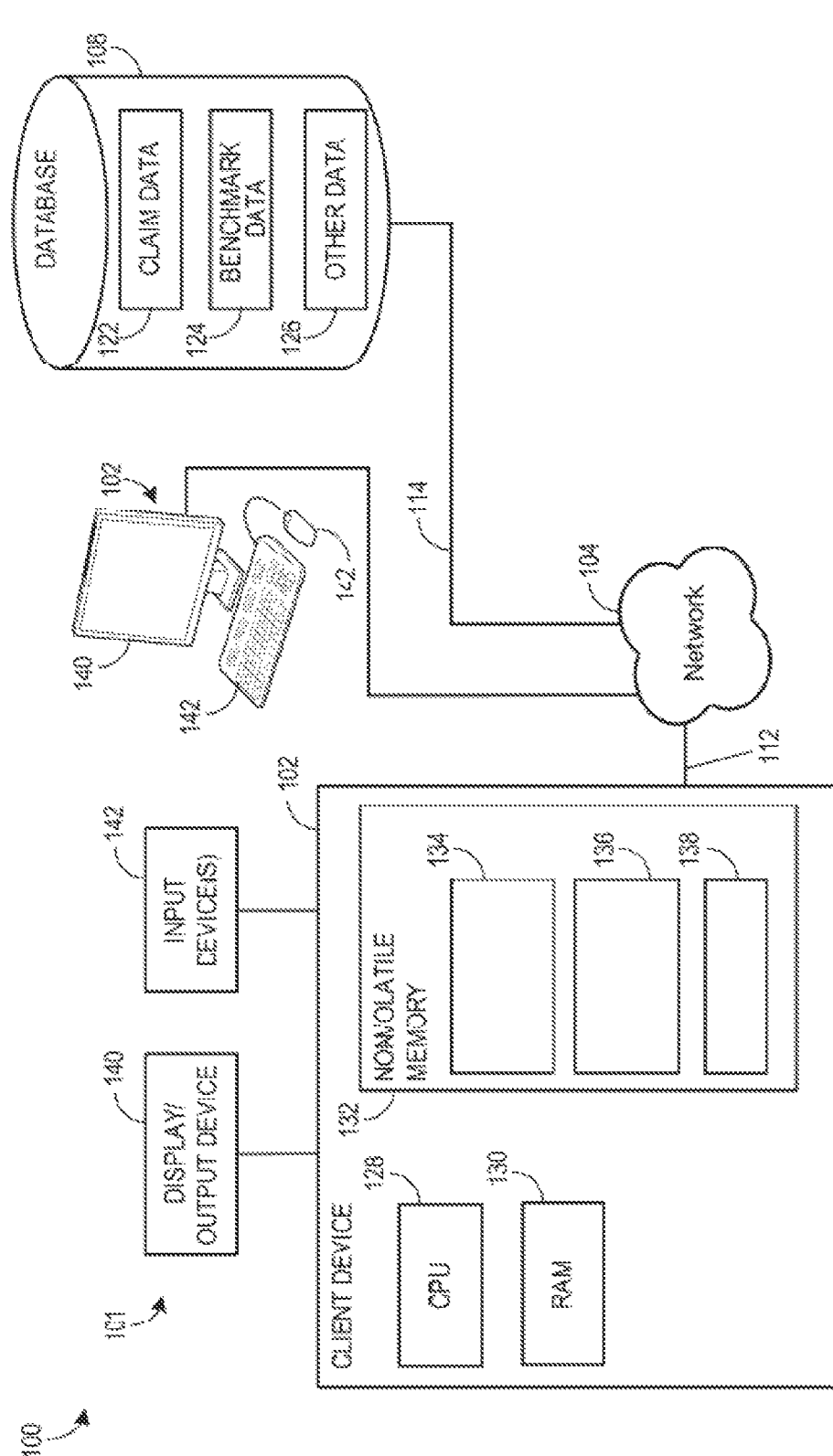
FIG. 2 is a system diagram of a processing system for performing the techniques described herein, in accordance with an example.

Systems, Computer-Readable Storage Media, and Methods Implemented by a Computer Processor FIG. 2 illustrates an exemplary embodiment 101 of a system 100 for assessing a subject's need for treatment for CKD or a kidney injury, risk for CKD or kidney injury, kidney tubule health during hypertension treatment, or need for discontinued or decreased hypertension treatment. Generally, the system 100 may include one or more client devices 102, a network 104, and a database 108. Each client device 102 may be communicatively coupled to the network 104 by one or more wired or wireless network connections 112, which may be, for example, a connection complying with a standard such as one of the IEEE 802.11 standards ("Wi-Fi"), the Ethernet standard, or any other appropriate network connection. Similarly, the database 108 may be communicatively coupled to the network 104 via one or more connections 114. (Of course, the database could alternatively be internal to one or more of the client devices 102.) The database 108 may store data related to the expression profiles for a variety of subjects, including, but not limited to, data of a sample obtained from a subject (e.g., baseline data for the subject), data of a reference or control population, etc.

As will be understood, the network 104 may be a local area network (LAN) or a wide-area network (WAN). That is, network 104 may include only local (e.g., intra-organization) connections or, alternatively, the network 104 may include connections extending beyond the organization and onto one or more public networks (e.g., the Internet). In some embodiments, for example, the client device 102 and the database 108 may be within the network operated by a single company (Company A). In other embodiments, for example, the client device(s) 102 may be on a network operated by Company A, while the database 108 may be on a network operated by a second company (Company B), and the networks of Company A and Company B may be coupled by a third network such as, for example, the Internet.

Referring still to FIG. 2, the client device 102 includes a processor 128 (CPU), a RAM 130, and a non-volatile memory 132. The non-volatile memory 132 may be any appropriate memory device including, by way of example and not limitation, a magnetic disk (e.g., a hard disk drive), a solid state drive (e.g., a flash memory), etc. Additionally, it will be understood that, at least with regard to FIG. 2, the database 108 need not be separate from the client device 102. Instead, in some embodiments, the database 108 is part of the non-volatile memory 132 and the data 122, 124, 126 may be stored as data within the memory 132. For example, the data 122 may be included as data in a spreadsheet file stored in the memory 132, instead of as data in the database 108. In addition to storing the records of the database 108 (in some embodiments), the memory 132 stores program data and other data necessary to analyze data of one or more sample and/or control populations, etc. For example, in an embodiment, the memory 132 stores a first routine 134, a second routine 136, and a third routine 138. The first routine 134 may receive data values related to a measured expression level of a gene, RNA, or protein of a sample obtained from a scaffold implanted in a test subject, and may process the data values received by the routine 134 through an algorithm to obtain a score. The second routine 136 may computer one or more statistical parameters of the data collected by the first routine 134, such as determining a mean value, a standard deviation value, etc. Additionally and/or alternatively, the second routine 136 may plot a score on a graphical or numerical output. Regardless, each of the routines is executable by the processor 128 and comprises a series of compiled or compilable machine-readable instructions stored in the memory 132. Additionally, the memory 132 may store generated reports or records of data output by one of the routines 134 or 136. Alternatively, the reports or records may be output to the database 108. One or more display/output devices 140 (e.g., printer, display, etc.) and one or more input devices 142 (e.g., mouse, keyboard, tablet, touch-sensitive interface, etc.) may also be coupled to the client device 102, as is generally known.

As will be understood, although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

For example, the network 104 may include but is not limited to any combination of a LAN, a MAN, a WAN, a mobile, a wired or wireless network, a private network, or a virtual private network. Moreover, while only two clients 102 are illustrated in FIG. 2 to simplify and clarify the description, it is understood that any number of client computers are supported and can be in communication with one or more servers (not shown).

Additionally, certain embodiments are described herein as including logic or a number of routines. Routines may constitute either software routines (e.g., code embodied on a machine-readable medium or in a transmission signal) or hardware routines. A hardware routine is tangible unit capable of performing certain operations and may be configured or arranged in a certain manner. In example embodiments, one or more computer systems (e.g., a standalone, client or server computer system) or one or more hardware routines of a computer system (e.g., a processor or a group of processors) may be configured by software (e.g., an application or application portion) as a hardware routine that operates to perform certain operations as described herein.

Similarly, the methods or routines described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Upon reading this disclosure, those of skill in the art will appreciate still additional alternative structural and functional designs for a system and a process for identifying terminal road segments through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The present disclosure provides systems comprising: a processor; a memory device coupled to the processor, and machine readable instructions stored on the memory device. In exemplary embodiments, the machine readable instructions that, when executed by the processor, cause the processor to (i) receive a plurality of data values, each data value is a measured level of at least two of the following: (a) α1m, (b) KIM-1, and (c) YKL-40; (ii) compare each data value in (i) to a corresponding control level; and (iii) provide an output relating to each data value relative to the corresponding control level. Optionally the control level is a baseline level taken prior to hypertension treatment.

Also provided herein are computer-readable storage media having stored thereon machine-readable instructions executable by a processor. In exemplary aspects, the machine-readable instructions comprise (i) instructions for receiving a plurality of data values, each data value is a measured level of at least two of the following: (a) α1m, (b) KIM-1, and (c) YKL-40; (ii) instructions for comparing each data value to in (i) to a corresponding control level; and (iii) instructions for providing an output relating to each data value relative to the corresponding control level. Optionally the control level is a baseline level taken prior to hypertension treatment.

Further provided herein are methods implemented by a processor in a computer. In exemplary embodiments, the method comprises the steps of (i) receiving a plurality of data values, each data value is a measured level of at least two of the following: (a) α1m, (b) KIM-1, and (c) YKL-40; (ii) comparing each data value in (i) to a corresponding control level; and (iii) providing an output relating to each data value relative to the corresponding control level. Optionally the control level is a baseline level taken prior to hypertension treatment.

In exemplary aspects of the system, computer-readable storage medium, or method of the present invention, the output relates to (i) whether a subject treated for hypertension should continue, discontinue, or decrease hypertension treatment, (ii) whether a subject is at risk for CKD, (iii) whether a subject needs treatment for CKD, (iv) a subject's kidney tubule health, (v) whether a subject is diagnosed with CKD. Also, in some instances, the system, computer-readable storage medium, or method further comprises (a) instructions for or the step of receiving a plurality of data values, each data value is a measured level of at least two of the following: (i) NGAL; (ii) UMOD; (iii) IL-18; (iv) β2m and (v) MCP-1; and (b) instructions for or the step of comparing each data value in (i) to a corresponding control level.

Exemplary Embodiments

The present disclosure provides the following numbered listing of exemplary embodiments:

1. A method of determining whether a subject treated for hypertension should continue hypertension treatment, said method comprising measuring the level of at least two of the following in a urine sample obtained from the subject:

i. Alpha-1 microglobulin (α1m);
   ii. Uromodulin (UMOD); and
   iii. Chitinase-3-like protein (YKL-40);
wherein the subject should continue with the hypertension treatment, when the levels are decreased or unchanged, relative to a control level, wherein the subject should discontinue or decrease the hypertension treatment, when the levels are increased, relative to a control level.

2. A method of identifying a subject at risk for chronic kidney disease (CKD) or a complication thereof, wherein the subject is on a hypertension treatment, said method comprising measuring the level of at least two of the following in a urine sample obtained from the subject:

i. Alpha-1 microglobulin (α1m);
   ii. Uromodulin (UMOD); and
   iii. Chitinase-3-like protein (YKL-40);
wherein the subject is at risk for CKD, when the levels are increased, relative to a control level.

3. A method of determining a subject's need for treatment for chronic kidney disease (CKD), wherein the subject is on a hypertension treatment, comprising measuring the level of at least two of the following in a urine sample obtained from the subject:

i. Alpha-1 microglobulin (α1m);
   ii. Uromodulin (UMOD); and
   iii. Chitinase-3-like protein (YKL-40);
wherein the subject needs treatment for CKD, when the levels are increased, relative to a control level.

4. A method of assessing kidney tubule health of a subject on a hypertension treatment, comprising measuring the level of at least two of the following in a urine sample obtained from the subject:

i. Alpha-1 microglobulin (α1m);
   ii. Uromodulin (UMOD); and
   iii. Chitinase-3-like protein (YKL-40);
wherein the subject is assessed for tubulointerstitial health, intra-renal inflammation, or a combination thereof based on the levels.

5. A method of diagnosing a subject with a drug-induced kidney injury, wherein the subject is on a hypertension treatment, comprising measuring the level of at least two of the following in a urine sample obtained from the subject:

i. Alpha-1 microglobulin (α1m);
   ii. Uromodulin (UMOD); and
   iii. Chitinase-3-like protein (YKL-40);
wherein the subject has a drug-induced kidney injury when the levels are increased, relative to a control level.

6. A method of treating a subject with hypertension, comprising:

a. administering to the subject a hypertension treatment;
   b. measuring the level of at least two of the following in a urine sample obtained from the subject:
     i. Alpha-1 microglobulin (α1m);
     ii. Uromodulin (UMOD); and
     iii. Chitinase-3-like protein (YKL-40); and
   c. continuing the hypertension treatment, when the levels are decreased or unchanged, relative to a control level, or discontinuing or decreasing the hypertension treatment, when the levels are increased relative to a control level.

7. A method of treating a subject with hypertension, wherein the subject is on a hypertension treatment, comprising (A) continuing the hypertension treatment, when the levels of at least two of (i) α1m, (ii) UMOD, and (iii) YKL-40, are decreased or unchanged in a urine sample obtained from the subject, relative to a control level, or (B) discontinuing or decreasing the hypertension treatment, when the levels of at least two of (i) α1m, (ii) UMOD, and (iii) YKL-40, are increased in a urine sample obtained from the subject, relative to a control level.

8. A method of monitoring a subject during hypertension treatment, comprising measuring the level of at least two of the following in a urine sample obtained from the subject:
   i. Alpha-1 microglobulin (α1m);
   ii. Uromodulin (UMOD); and
   iii. Chitinase-3-like protein (YKL-40);
wherein the measured levels are indicative of (a) the subject's kidney tubule health, (b) whether it is safe for the subject to continue on the hypertension treatment or whether modifications to the hypertension treatment are needed, (c) whether the subject is at risk for or needs treatment or increased monitoring for CKD or AKI, or complications thereof, wherein when the levels of at least two of (i) α1m, (ii) UMOD, and (iii) YKL-40, are increased in a urine sample obtained from the subject, relative to a control level, the subject should discontinue or decrease the hypertension treatment, is at an increased risk or needs treatment or increased monitoring for CKD, AKI, or a complication thereof.

9. The method of any one of the preceding embodiments, comprising measuring the level of α1m and UMOD.

10. The method of any one of the preceding embodiments, comprising measuring the level of α1m and YKL-40.

11. The method of any one of the preceding embodiments, comprising measuring the level of YKL-40 and UMOD.

12. The method of any one of the preceding embodiments, comprising measuring the level of all three of: α1m, UMOD, and YKL-40.

13. The method of any one of the preceding embodiments, further comprising determining the subject's urine albumin:urine creatinine ratio (ACR).

14. The method of any one of the preceding embodiments, further comprising measuring the level of at least one of the following in a urine sample obtained from the subject:
   i. neutrophil gelatinase associated lipocalin (NGAL);
   ii. kidney injury molecule (KIM-1);
   iii. Interleukin-18 (IL-18)
   iv. Beta-2 microglobulin (β2m); and
   v. Monocyte chemoattractant protein-1 (MCP-1).

15. The method of embodiment 14, comprising measuring the level of at least 2, 3, or 4 of NGAL, KIM-1, IL-18, β2m, and MCP-1 or at least 5, 6, or all of NGAL, KIM-1, IL-18, β2m, and MCP-1.

16. The method of any one of the preceding embodiments, further comprising (i) measuring the subject's blood level of one or more of Soluble TNFR-1, Soluble TNFR-2, and KIM-1, (ii) measuring the subject's urine level of TFF3 and/or clusterin, (iii) measuring the levels of hippuric acid, isovalerylglycine, pheylacetylglutamine, triglycine, cinnamoylglycine, suberric acid from a urine or blood sample obtained from the subject, (iv) measuring the subject's urine level ammonia, or (v) a combination thereof.

17. The method of any one of the previous embodiments, further comprising measuring the level of blood creatinine, and optionally calculating the subject's estimated glomerular filtration rate (eGFR).

18. The method of any one of the previous embodiments, comprising simultaneously measuring levels of two or more of α1m, UMOD, YKL-40, and optionally one or more of NGAL, KIM-1, IL-18, β2m, MCP-1, and creatinine in the urine sample.

19. The method of any one of the previous embodiments, further comprising obtaining the urine sample from the subject, and, optionally, centrifuging the urine.

20. The method of any one of the previous embodiments, comprising contacting the urine sample with a combination of binding agents.

21. The method of embodiment 20, wherein the binding agents are antibodies, antigen binding fragments thereof, or aptamers.

22. The method of any one of the previous embodiments, comprising measuring the level of creatinine in the urine sample and adjusting each level to the level of urine creatinine, urine osmolality or urine specific gravity.

23. The method of any one of the previous embodiments, wherein the hypertension treatment comprises a diuretic, a beta blocker, an ACE inhibitor, an angiotensin II receptor blocker, a calcium channel blocker, an alpha blocker, an alpha-2 receptor agonist, a central agonist, a renin inhibitor, an arterial vasodilator, or a combination thereof.

24. A kit or assay system comprising (A) a first binding agent which specifically binds to (i) Alpha-1 microglobulin (α1m), (ii) Uromodulin (UMOD); or (iii) Chitinase-3-like protein (YKL-40) and (B) a second binding agent, which binds to (i) α1m, (ii) UMOD; or (iii) YKL-40, wherein the first binding agent and second binding agent bind to different biomarker, optionally, wherein the kit further comprises (C) a third binding agent which binds to (i) α1m, (ii) UMOD; or (iii) YKL-40 and wherein the third binding agent binds to a biomarker different from the first binding agent and second binding agent.

25. The kit or assay system of embodiment 24, comprising a fourth binding agent which binds:
   i. neutrophil gelatinase associated lipocalin (NGAL);
   ii. kidney injury molecule (KIM-1);
   iii. Interleukin-18 (IL-18)
   iv. Beta-2 microglobulin (β2m); or
   v. Monocyte chemoattractant protein-1 (MCP-1),
optionally, further comprising a fifth binding agent which binds to NGAL, KIM-1, IL-18, β2m, or MCP-1, wherein the fourth binding agent and fifth binding agent bind to different biomarkers;
optionally, further comprising a sixth binding agent which binds to NGAL, KIM-1, IL-18, β2m, or MCP-1, wherein the sixth binding agent binds to a biomarker different from the fourth binding agent and fifth binding agent;
   optionally, further comprising a seventh binding agent which binds to NGAL, KIM-1, IL-18, β2m, or MCP-1, wherein the seventh binding agent binds to a biomarker different from the fourth binding agent, fifth binding agent, and sixth binding agent; and
   optionally, further comprising an eighth binding agent which binds to NGAL, KIM-1, IL-18, β2m, or MCP-1, wherein the eighth binding agent binds to a biomarker different from the fourth binding agent, fifth binding agent, sixth binding agent, and seventh binding agent.

26. The kit or assay system of embodiment 24 or 25, wherein the binding agents are antibodies, antigen-binding fragments thereof, or aptamers.

27. The kit or assay system of any one of embodiments 24 to 26, wherein the binding agents are bound to a solid support, optionally, wherein the binding agents are bound to a solid support at a unique location.

28. A system comprising machine readable instructions that, when executed by the processor, cause the processor to:
   (i) receive a plurality of data values, each data value is a measured level of at least two of the following:
      a) Alpha-1 microglobulin (α1m);
      b) Uromodulin (UMOD); and
      c) Chitinase-3-like protein (YKL-40);
   (ii) compare each data value in (i) to a corresponding control level; and
   (iii) provide an output relating to each data value relative to the corresponding control level.

29. A computer-readable storage media having stored thereon machine-readable instructions executable by a processor, wherein the instructions comprise:
   (i) instructions for receiving a plurality of data values, each data value is a measured level of at least two of the following:
      a) Alpha-1 microglobulin (α1m);
      b) Uromodulin (UMOD); and
      c) Chitinase-3-like protein (YKL-40).
   (ii) instructions for comparing each data value to in (i) to a corresponding control level; and
   (iii) instructions for providing an output relating to each data value relative to the corresponding control level.

30. A method implemented by a processor in a computer, the method comprising the steps of:
   (i) receiving a plurality of data values, each data value is a measured level of at least two of the following:
      a) Alpha-1 microglobulin (α1m);
      b) Uromodulin (UMOD); and
      c) Chitinase-3-like protein (YKL-40).
   (ii) comparing each data value in (i) to a corresponding control level; and
   (iii) providing an output relating to each data value relative to the corresponding control level.

31. The system, computer-readable storage medium, or method of any one of embodiments 28-30, wherein the output relates to (i) whether a subject treated for hypertension should continue, discontinue, or decrease hypertension treatment, (ii) whether a subject is at risk for CKD, (iii) whether a subject needs treatment for CKD, (iv) a subject's kidney tubule health, (v) whether a subject is diagnosed with CKD.

32. The system, computer-readable storage medium, or method of any one of embodiments 28-31, further comprising
   a. instructions for or the step of receiving a plurality of data values, each data value is a measured level of at least two of the following:
      i. neutrophil gelatinase associated lipocalin (NGAL);
      ii. kidney injury molecule (KIM-1);
      iii. Interleukin-18 (IL-18)
      iv. Beta-2 microglobulin (β2m); and
      v. Monocyte chemoattractant protein-1 (MCP-1) and
   b. instructions for or the step of comparing each data value in (a) to a corresponding control level.

The following examples are given merely to illustrate the present invention and not in any way to limit its scope.

EXAMPLES

Example 1

This example demonstrates urinary biomarkers of kidney damage in incident chronic kidney disease among persons undergoing intensive systolic blood pressure control.

It is unknown whether the increased incidence of chronic kidney disease (CKD) in the setting of intensive systolic blood pressure (SBP) lowering is accompanied by intrinsic kidney injury. The objective of this study was to determine whether changes in urinary biomarkers of kidney damage were associated with risk of incident CKD and whether the extent of biomarker changes among incident CKD cases differed between persons undergoing intensive (<120 mmHg) vs. standard (<140 mmHg) SBP management. The study design was a nested case-control study within the Systolic Blood Pressure Intervention Trial (SPRINT). In adults with high blood pressure and elevated cardiovascular risk without baseline kidney disease, nine urinary biomarkers of kidney damage were measured at baseline and 1 year. Linear mixed-effects models were used to estimate 1-year biomarker changes. Cases (N=162) were persons who developed incident CKD during the entire trial follow-up period (128 in the intensive arm and 124 in the standard arm). Controls (N=162) were persons without CKD, who were matched on age, sex, race, baseline estimated glomerular filtration rate (eGFR), and randomization arm. We aimed to determine (1) whether baseline biomarker concentrations were associated with incident CKD; (2) whether changes in urinary biomarkers were associated with risk of incident CKD; and (3) whether the extent of biomarker changes in the setting of incident CKD differed between participants who were randomized to intensive vs. standard SBP management. We hypothesized that biomarker changes among incident CKD cases in the intensive arm would represent benign hemodynamic accommodation rather than intrinsic tissue injury.

Results

Following matching controls to cases on age, gender, race, baseline eGFR and randomization arm, additional baseline characteristics and cardiovascular risk factors were well balanced between respective incident CKD cases and controls (Table 1). The only exception was baseline systolic blood pressure, which was significantly higher among incident CKD cases than among matched controls within both intervention arms. At 1 year after randomization, incident CKD cases in both intervention arms had significantly increased serum creatinine concentrations and decreased eGFRs, compared with respective controls. In addition, individuals in the intensive arm were prescribed greater numbers of anti-hypertensive medications, including angiotensin-converting enzyme inhibitors and angiotensin receptor blockers, at 1 year than those in the standard arm. Within the intensive arm, incident CKD cases were prescribed significantly more antihypertensive medications and had significantly lower diastolic blood pressures at 1 year, compared with matched controls.

TABLE 1

Characteristics of Incident CKD Case Participants and Matched Control
Participants in SPRINT at Baseline and Year 1, by Randomization Group*

| | Intensive Arm (N = 128 pairs) | | | Standard Arm (N = 34 pairs) | | |
|---|---|---|---|---|---|---|
| | Cases | Controls | P-value* | Cases | Controls | P-value* |
| Baseline Characteristics | | | | | | |
| Age, years | 67 ± 9 | 67 ± 9 | & | 68 ± 8 | 68 ± 9 | & |
| Female, N (%) | 45 (35) | 45 (35) | & | 14 (41) | 14 (41) | & |
| Race, N (%) | | | & | | | & |
| African American | 41 (32) | 42 (33) | | 13 (38) | 13 (38) | |
| Caucasian | 71 (56) | 67 (52) | | 18 (53) | 18 (53) | |
| Hispanic/Other | 16 (13) | 19 (15) | | 3 (9) | 3 (9) | |
| eGFR, mL/min/1.73 m$^2$ | | | | | | |
| MDRD | 80 ± 15 | 79 ± 17 | & | 75 ± 9 | 74 ± 12 | & |
| CKD-EPI (with CysC) | 80 ± 14 | 80 ± 14 | | 77 ± 12 | 77 ± 12 | |
| SBP, mmHg | 146 ± 19 | 140 ± 15 | 0.007 | 151 ± 14 | 140 ± 15 | 0.009 |
| DBP, mmHg | 80 ± 14 | 80 ± 11 | 0.92 | 80 ± 13 | 78 ± 11 | 0.34 |
| Serum creatine, g/dL | 0.94 ± 0.18 | 0.95 ± 0.19 | 0.17 | 0.97 ± 0.16 | 0.99 ± 0.18 | 0.42 |
| Total cholesterol, mg/dL | 195 ± 47 | 192 ± 40 | 0.53 | 193 ± 44 | 195 ± 32 | 0.80 |
| HDL cholesterol, mg/dL | 54 ± 16 | 52 ± 14 | 0.26 | 57 ± 15 | 59 ± 14 | 0.67 |
| Body mass index, kg/m$^2$ | 30 ± 6 | 31 ± 6 | 0.66 | 28 ± 5 | 30 ± 6 | 0.40 |
| History of clinical CVD, N (%) | 24 (19) | 24 (19) | 1.00 | 7 (21) | 5 (15) | 0.57 |
| History of CHF, N (%) | 2 (1.6) | 2 (1.6) | 1.00 | 0 (0.0) | 0 (0.0) | — |
| ACE-I or ARB use, N (%) | 54 (42) | 51 (40) | 0.71 | 10 (29) | 10 (29) | 1.00 |
| # anti-hypertensives, N | 1.8 ± 1.1 | 1.7 (1.1) | 0.52 | 1.7 ± 1.0 | 1.8 ± 1.1 | 0.71 |
| Current smoker, N (%) | 18 (14) | 15 (12) | 0.58 | 7 (21) | 3 (9) | 0.18 |
| Year 1$^\#$ characteristics | | | | | | |
| Serum creatinine, g/dL | 1.25 ± 0.27 | 0.99 ± 0.20 | <0.001 | 1.35 ± 0.83 | 0.99 ± 0.19 | 0.006 |
| Change from baseline | 0.31 ± 0.22 | 0.04 ± 0.12 | <0.001 | 0.39 ± 0.83 | 0.01 ± 0.09 | 0.008 |
| eGRF, mL/min/1.73 m$^2$ | | | | | | |
| MDRD | 58 ± 12 | 75 ± 15 | <0.001 | 59 ± 19 | 74 ± 15 | 0.004 |
| SBP, mmHg | 119 ± 14 | 121 ± 12 | 0.25 | 140 ± 15 | 133 ± 13 | 0.077 |
| DBP, mmHg | 66 ± 11 | 70 ± 10 | 0.002 | 76 ± 13 | 76 ± 9 | 0.74 |
| ACE-I or ARB use, N (%) | 114 (92) | 92 (74) | <0.0007 | 25 (74) | 18 (53) | 0.083 |
| # anti-hypertensive, N | 3.3 ± 1.2 | 2.7 ± 0.9 | <0.0001 | 2.3 ± 1.1 | 1.9 ± 1.4 | 0.19 |

ACE = angiotensin-converting enzyme;
ARB = angiotensin-receptor blocker;
CHF = congestive heart failure;
CKD = chronic kidney disease;
CKD-EPI = Chronic Kidney Disease Epidemiology Collaboration;
CVD = cardiovascular disease;
eGFR = estimated glomerular filtration rate;
HDL = high-density lipoprotein;
MDRD = Modification of Diet in Renal Disease;
SPRINT = Systolic Blood Pressure Intervention Trial
*percentages may not sum to 100 due to rounding.
& Calculated using a univariate conditional logistic regression model
Matching factor; no test was performed.

At baseline, the nine kidney biomarkers were only weakly inter-correlated (Appendix Table 3); moderate correlations were observed for only two biomarkers pairs ($\alpha$1m and $\beta$2m, r=0.53; KIM-1 and MCP-1, r=0.49), whereas the other pairwise comparisons showed weak associations. We evaluated the association of baseline biomarker concentrations and incident CKD case status, adjusting for baseline SBP and urine creatinine (Table 2). Higher concentrations of ACR, KIM-1, and MCP-1 were each significantly associated with higher odds of incident CKD. These results were not impacted by re-weighting of the matched controls to the broader cohort of non-cases (Appendix Table 4). When stratified by intervention arm, we observed similar effect sizes in each group, although the associations were not statistically significant in the standard arm (Appendix Table 5).

APPENDIX TABLE 3

Spearman correlations of Baseline Biomarker Concentrations

| Variable | ACR | $\alpha_1$M | $\beta_2$M | Uromodulin | IL-18 | KIM-1 | MCP-1 | YKL-40 | NGAL |
|---|---|---|---|---|---|---|---|---|---|
| ACR | 1 | | | | | | | | |
| $\alpha_1$M | 0.36 | 1 | | | | | | | |
| $\beta_2$M | 0.27 | 0.53 | 1 | | | | | | |
| Uromodulin | 0.01 | 0.16 | 0.21 | 1 | | | | | |
| IL-18 | 0.23 | 0.21 | 0.09 | −0.08 | 1 | | | | |
| KIM-1 | 0.25 | 0.03 | 0.08 | −0.003 | 0.23 | 1 | | | |
| MCP-1 | 0.27 | 0.05 | 0.07 | −0.01 | 0.24 | 0.49 | 1 | | |
| YKL-40 | 0.21 | 0.08 | 0.28 | −0.04 | 0.26 | 0.11 | 0.17 | 1 | |

APPENDIX TABLE 3-continued

| | | | | Spearman correlations of Baseline Biomarker Concentrations | | | | | |
|---|---|---|---|---|---|---|---|---|---|
| Variable | ACR | $\alpha_1$M | $\beta_2$M | Uromodulin | IL-18 | KIM-1 | MCP-1 | YKL-40 | NGAL |
| NGAL | 0.19 | 0.03 | 0.19 | 0.08 | 0.41 | 0.21 | 0.20 | 0.43 | 1 |

ACR = albumin-creatinine ratio;
$\alpha_1$M = $\alpha_1$-microglobulin;
$\beta_2$M = $\beta_2$-microglobulin;
IL-18 = interleukin-18;
KIM-1 = kidney injury molecule-1;
MCP-1 = monocyte chemoattractant protein-1;
NGAL = neutrophil gelatinase-associated lipocalin;
YKL-40 = anti-chitinase-3-like protein 1.

APPENDIX TABLE 4

Appendix Table 4. Baseline Biomarker Concentrations Among
Incident CKD Case Participants and Matched Control Participants
in Both Randomization Groups of SPRINT Combined: Comparison
of Results of Unweighted and Weighted LR Analyses

| Biomarker | Pairs, n | Unweighted LR Analysis* | | Weighted LR Analysis | |
|---|---|---|---|---|---|
| | | OR (95% CI)† | P Value | OR (95% CI)† | P Value |
| ACR, mg/g | 150 | 1.50 (1.14-1.98) | 0.004 | 1.58 (1.16-2.15) | 0.004 |
| IL-18, pg/mL | 158 | 1.30 (0.93-1.79) | 0.12 | 1.29 (0.94-1.77) | 0.11 |
| KIM-1, pg/mL | 158 | 1.51 (1.05-2.17) | 0.027 | 1.54 (0.99-2.40) | 0.058 |
| NGAL, ng/mL | 157 | 0.96 (0.71-1.30) | 0.80 | 0.89 (0.67-1.19) | 0.43 |
| MCP-1, pg/mL | 158 | 1.70 (1.13-2.56) | 0.012 | 1.70 (1.10-2.62) | 0.018 |
| YKL-40, pg/mL | 158 | 1.18 (0.90-1.56) | 0.23 | 1.10 (0.86-1.42) | 0.44 |
| $\beta_2$M, ng/mL | 154 | 0.95 (0.74-1.22) | 0.68 | 0.95 (0.74-1.21) | 0.66 |
| $\alpha_1$M, mg/L | 157 | 1.18 (0.90-1.56) | 0.23 | 1.14 (0.84-1.53) | 0.40 |
| Uromodulin, µg/mL | 157 | 1.04 (0.77-1.40) | 0.80 | 0.91 (0.66-1.25) | 0.55 |

ACR = albumin-creatinine ratio;
$\alpha_1$M = $\alpha_1$-microglobulin;
$\beta_2$M = $\beta_2$-microglobulin;
CKD = chronic kidney disease;
IL-18 = interleukin-18;
KIM-1 = kidney injury molecule-1;
LR = logistic regression;
MCP-1 = monocyte chemoattractant protein-1;
NGAL = neutrophil gelatinase-associated lipocalin;
OR = odds ratio;
SPRINT = Systolic Blood Pressure Intervention Trial;
YKL-40 = anti-chitinase-3-like protein 1.
*See Table 2.
†Per SD increase in $\log_2$-transformed biomarker concentrations. All models except for ACR adjust for $\log_2$-transformed urinary creatinine concentrations. All models adjust for baseline systolic blood pressure.

APPENDIX TABLE 5

Comparison of Baseline Biomarker Concentrations Among Incident CKD Case Participants
and Matched Control Participants in SPRINT, by Randomization Group Appendix Table 5A.

| Biomarker | Pairs, n | Intensive BP Group | | | |
|---|---|---|---|---|---|
| | | Geometric Mean (±SE) | | | |
| | | Case Participants | Control Participants | OR (95% CI)* | P Value |
| ACR, mg/g | 118 | 19.3 ± 2.4 | 10.6 ± 1.01 | 1.55 (1.13-2.11) | 0.006 |
| IL-18, pg/mL | 124 | 37.0 ± 3.3 | 36.6 ± 3.1 | 1.20 (0.85-1.69) | 0.30 |
| KIM-1, pg/mL | 124 | 621.3 ± 72.4 | 601.0 ± 70.8 | 1.47 (0.98-2.20) | 0.062 |
| NGAL, ng/mL | 124 | 25.3 ± 2.7 | 28.5 ± 3.1 | 0.96 (0.69-1.33) | 0.80 |
| MCP-1, pg/mL | 124 | 163.3 ± 15.2 | 154.7 ± 16.6 | 1.78 (1.12-2.83) | 0.014 |
| YKL-40, pg/mL | 124 | 641.6 ± 68.6 | 627.1 ± 66.1 | 1.13 (0.64-1.53) | 0.41 |
| $\beta_2$M, ng/mL | 121 | 78.5 ± 9.5 | 83.0 ± 9.1 | 0.89 (0.66-1.20) | 0.45 |

APPENDIX TABLE 5-continued

Comparison of Baseline Biomarker Concentrations Among Incident CKD Case Participants and Matched Control Participants in SPRINT, by Randomization Group

| $\alpha_1$M, mg/L | 124 | 5.12 ± 0.69 | 4.51 ± 0.64 | 1.15 (0.84-1.58) | 0.39 |
| Uromodulin, µg/mL | 124 | 10.3 ± 0.70 | 10.6 ± 0.83 | 1.10 (0.79-1.52) | 0.58 |

Appendix Table 5B.

| | | Standard BP Group | | | |
| | | Geometric Mean (±SE) | | | |
| Biomarker | Pairs, n | Case Participants | Control Participants | OR (95% CI)* | P Value |
|---|---|---|---|---|---|
| ACR, mg/g | 32 | 14.9 ± 2.5 | 10.2 ± 1.4 | 1.39 (0.67-2.88) | 0.38 |
| IL-18, pg/mL | 34 | 36.5 ± 4.2 | 27.7 ± 3.8 | 2.65 (0.85-8.24) | 0.092 |
| KIM-1, pg/mL | 34 | 511.8 ± 97.9 | 384.8 ± 74.4 | 1.58 (0.66-3.79) | 0.30 |
| NGAL, ng/mL | 33 | 28.3 ± 6.2 | 26.3 ± 4.7 | 0.90 (0.40-2.00) | 0.79 |
| MCP-1, pg/mL | 34 | 149.2 ± 28.3 | 127.5 ± 20.4 | 1.09 (0.41-2.89) | 0.87 |
| YKL-40, pg/mL | 34 | 735.9 ± 213.2 | 475.2 ± 78.3 | 1.36 (0.58-3.20) | 0.48 |
| $\beta_2$M, ng/mL | 33 | 77.7 ± 20.0 | 58.5 ± 10.4 | 1.17 (0.70-1.93) | 0.55 |
| $\alpha_1$M, mg/L | 33 | 4.48 ± 1.24 | 3.01 ± 0.81 | 1.45 (0.78-2.70) | 0.24 |
| Uromodulin, µg/mL | 33 | 8.8 ± 1.0 | 9.4 ± 0.80 | 0.84 (0.41-1.73) | 0.63 |

ACR = albumin-creatinine ratio;
$\alpha_1$M = $\alpha_1$-microglobulin;
$\beta_2$M = $\beta_2$-microglobulin;
BP = blood pressure;
CKD = chronic kidney disease;
IL-18 = interleukin-18;
KIM-1 = kidney injury molecule-1;
MCP-1 = monocyte chemoattractant protein-1;
NGAL = neutrophil gelatinase-associated lipocalin;
OR = odds ratio;
SPRINT = Systolic Blood Pressure Intervention Trial;
YKL-40 = anti-chitinase-3-like protein 1.
*Based on SD increase in $\log_2$-transformed biomarker concentrations. All models except those for ACR adjust for $\log_2$-transformed urinary creatinine concentrations. All models adjust for baseline systolic BP.

TABLE 2

Comparison of Baseline Biomarker Concentrations in Incident CKD Case Participants and Matched Control Participants in Both Randomization Groups of SPRINT Combined

| | | Baseline Biomarker Concentrations | | | |
| Biomarker | N (pairs) | Cases | Controls | OR* (95% CI) | P-value |
|---|---|---|---|---|---|
| ACR, mg/g | 150 | 18.2 ± 1.9 | 10.5 ± 0.85 | 1.50 (1.14-1.98) | 0.004 |
| IL-18, pg/mL | 158 | 36.9 ± 2.7 | 34.4 ± 2.5 | 1.30 (0.93-1.79) | 0.12 |
| KIM-1, pg/mL | 158 | 595.9 ± 59.7 | 546.2 ± 55.8 | 1.51 (1.05-2.17) | 0.027 |
| NGAL, ng/mL | 157 | 25.9 ± 2.5 | 28.1 ± 2.6 | 0.96 (0.71-1.30) | 0.80 |
| MCP-1, pg/mL | 158 | 160.2 ± 13.4 | 148.4 ± 13.5 | 1.70 (1.13-2.56) | 0.012 |
| YKL-40, pg/mL | 158 | 660.8 ± 68.8 | 590.8 ± 53.3 | 1.18 (0.90-1.56) | 0.23 |
| B2M, ng/mL | 154 | 78.3 ± 8.5 | 77.0 ± 7.3 | 0.95 (0.74-1.22) | 0.68 |
| A1M, mg/L | 157 | 4.98 ± 0.61 | 4.14 ± 0.52 | 1.18 (0.90-1.56) | 0.23 |
| UMOD, µg/mL | 157 | 9.95 ± 0.58 | 10.34 ± 0.67 | 1.04 (0.77-1.40) | 0.80 |

A1M = $\alpha_1$-microglobulin;
ACR = albumin-creatinine ratio;
B2M = $\beta_2$-microglobulin;
CKD = chronic kidney disease;
IL-18 = interleukin-18;
KIM-1 = kidney injury molecule-1;
MCP-1 = monocyte chemoattractant protein-1;
NGAL = neutrophil gelatinase-associated lipocalin;
OR = odds ratio;
SPRINT = Systolic Blood Pressure Intervention Trial;
YKL-40 = anti-chitinase-3-like protein 1.
*Per SD increase in $\log_2$-transformed biomarker concentrations. All models except that for ACR were adjusted for $\log_2$-transformed urinary creatinine concentrations. All models were adjusted for baseline systolic blood pressure.

The 1-year biomarker concentrations of cases and controls for each intervention arm are presented in Appendix Table 6. We compared the 1-year relative changes of each biomarker between cases and controls and found that incident CKD cases in the intensive arm had relative declines in ACR, IL-18, YKL-40, and uromodulin that significantly differed from the relative changes in matched controls (FIG. 1). The 1-year relative changes in KIM-1, NGAL, $\beta$2M, and $\alpha$1m did not differ significantly between intensive arm cases and controls, and MCP-1 relatively increased in intensive arm cases. In the standard arm, there were no significant differences between cases and controls in the 1-year relative changes for any biomarker. We tested for interactions comparing the case-control differences between the two intervention arms and found none to be statistically significant (Appendix Table 7).

APPENDIX TABLE 6

One-Year Biomarker Concentrations Among Incident CKD Case Participants and Matched Control Participants in SPRINT, Overall and by Intervention Group

Appendix Table 6A.

| | | Intensive BP Group | |
| | | Geometric Mean (±SE) | |
| Biomarker | Pairs, n | Case Participants | Control Participants |
| --- | --- | --- | --- |
| ACR, mg/g | 99 | 11.2 ± 1.3 | 9.3 ± 1.0 |
| IL-18, pg/mL | 121 | 33.6 ± 2.9 | 36.9 ± 3.3 |
| KIM-1, pg/mL | 121 | 819.2 ± 88.3 | 634.9 ± 76.4 |
| NGAL, ng/mL | 120 | 32.4 ± 3.5 | 32.8 ± 3.9 |
| MCP-1, pg/mL | 121 | 244.8 ± 23.5 | 162.6 ± 18.7 |
| YKL-40, pg/mL | 121 | 427.1 ± 59.3 | 506.3 ± 60.9 |
| $\beta_2$M, ng/mL | 110 | 56.5 ± 9.0 | 56.4 ± 6.3 |
| $\alpha_1$M, mg/L | 120 | 4.14 ± 0.64 | 2.92 ± 0.42 |
| Uromodulin, $\mu$g/mL | 119 | 8.4 ± 0.54 | 11.1 ± 0.70 |

Appendix Table 6B.

| | | Standard BP Group | |
| | | Geometric Mean (±SE) | |
| Biomarker | Pairs, n | Case Participants | Control Participants |
| --- | --- | --- | --- |
| ACR, mg/g | 30 | 13.3 ± 3.0 | 11.1 ± 2.2 |
| IL-18, pg/mL | 34 | 43.0 ± 6.6 | 34.5 ± 4.9 |
| KIM-1, pg/mL | 34 | 977.3 ± 165.1 | 560.3 ± 93.2 |
| NGAL, ng/mL | 32 | 40.8 ± 8.5 | 29.6 ± 6.2 |
| MCP-1, pg/mL | 34 | 275.8 ± 48.6 | 152.6 ± 27.3 |
| YKL-40, pg/mL | 34 | 948.8 ± 295.0 | 610.3 ± 115.2 |
| $\beta_2$M, ng/mL | 29 | 92.9 ± 24.5 | 58.7 ± 14.1 |
| $\alpha_1$M, mg/L | 32 | 7.52 ± 2.00 | 2.52 ± 0.71 |
| Uromodulin, $\mu$g/mL | 32 | 10.1 ± 1.22 | 9.8 ± 1.02 |

Appendix Table 6C.

| | | Overall | |
| | | Geometric Mean (±SE) | |
| Biomarker | Pairs, n | Case Participants | Control Participants |
| --- | --- | --- | --- |
| ACR, mg/g | 129 | 11.6 ± 1.2 | 9.7 ± 0.9 |
| IL-18, pg/mL | 155 | 35.5 ± 2.7 | 36.4 ± 2.8 |
| KIM-1, pg/mL | 155 | 851.5 ± 78.3 | 617.9 ± 62.2 |
| NGAL, ng/mL | 152 | 34.1 ± 3.2 | 32.1 ± 3.3 |
| MCP-1, pg/mL | 155 | 251.3 ± 21.2 | 160.4 ± 15.7 |
| YKL-40, pg/mL | 155 | 508.9 ± 66.3 | 527.5 ± 54.1 |

APPENDIX TABLE 6-continued

One-Year Biomarker Concentrations Among Incident CKD Case Participants and Matched Control Participants in SPRINT, Overall and by Intervention Group

| | | | |
| --- | --- | --- | --- |
| $\beta_2$M, ng/mL | 139 | 62.7 ± 8.6 | 56.9 ± 5.8 |
| $\alpha_1$M, mg/L | 152 | 4.70 ± 0.64 | 2.83 ± 0.36 |
| Uromodulin, $\mu$g/mL | 151 | 8.8 ± 0.49 | 10.8 ± 0.59 |

ACR = albumin-creatinine ratio;
$\alpha_1$M = $\alpha_1$-microglobulin;
$\beta_2$M = $\beta_2$-microglobulin;
BP = blood pressure;
CKD = chronic kidney disease;
IL-18 = interleukin-18;
KIM-1 = kidney injury molecule-1;
MCP-1 = monocyte chemoattractant protein-1;
NGAL = neutrophil gelatinase-associated lipocalin;
SPRINT = Systolic Blood Pressure Intervention Trial;
YKL-40 = anti-chitinase-3-like protein 1.

APPENDIX TABLE 7

Comparisons of 1-Year Changes in Biomarker Concentrations Among Incident CKD Case Participants and Matched Control Participants in SPRINT, by Randomization Group

Appendix Table 7A.

| | | Intensive Group | |
| | | Change (95% CI), %* | |
| Biomarker | Pairs, n | Case Participants | Control Participants |
| --- | --- | --- | --- |
| ACR | 99 | −41 (−52 to −27) | −20 (−34 to −1) |
| IL-18 | 121 | −14 (−25 to −2) | 5 (−8 to 20) |
| KIM-1 | 121 | 26 (10 to 44) | 16 (2 to 33) |
| NGAL | 120 | 23 (2 to 50) | 25 (3 to 51) |
| MCP-1 | 121 | 39 (20 to 61) | 13 (−2 to 31) |
| YKL-40 | 121 | −40 (−54 to −24) | −18 (−36 to 5) |
| $\beta_2$M | 110 | −38 (−54 to −18) | −40 (−54 to −20) |
| $\alpha_1$M | 120 | −20 (−39 to 6) | −36 (−51 to −16) |
| Uromodulin | 119 | −23 (−34 to −11) | 10 (−6 to 28) |

Appendix Table 7B.

| | | Intensive Group | |
| | | Change (95% CI), %* | |
| Biomarker | Pairs, n | Case Participants | Control Participants |
| --- | --- | --- | --- |
| ACR | 30 | 17 (−19 to 70) | 10 (−25 to 60) |
| IL-18 | 34 | −5 (−25 to 21) | 20 (−6 to 52) |
| KIM-1 | 34 | 54 (20 to 97) | 40 (10 to 79) |
| NGAL | 32 | 15 (−20 to 67) | 11 (−22 to 58) |
| MCP-1 | 34 | 44 (10 to 89) | 18 (−10 to 54) |
| YKL-40 | 34 | 0 (−37 to 58) | 8 (−32 to 70) |
| $\beta_2$M | 29 | 25 (−28 to 114) | −7 (−45 to 59) |
| $\alpha_1$M | 32 | 56 (−8 to 163) | −23 (−54 to 28) |
| Uromodulin | 32 | 10 (−18 to 48) | 8 (−19 to 42) |

Appendix Table 7C.

| | | P Value | | | |
| | Case Participants | Case Participants vs. Control Participants | | | Control Participants |
| Biomarker | vs. Case Participants | Intensive Group | Standard Group | Inter-action | vs. Control Participants |
| --- | --- | --- | --- | --- | --- |
| ACR | 0.001 | 0.027 | 0.80 | 0.20 | 0.14 |
| IL-18 | 0.44 | 0.019 | 0.16 | 0.89 | 0.33 |
| KIM-1 | 0.14 | 0.37 | 0.58 | 0.94 | 0.17 |
| NGAL | 0.74 | 0.94 | 0.87 | 0.85 | 0.55 |

APPENDIX TABLE 7-continued

Comparisons of 1-Year Changes in Biomarker Concentrations
Among Incident CKD Case Participants and Matched Control
Participants in SPRINT, by Randomization Group

| MCP-1 | 0.80 | 0.04 | 0.28 | 0.99 | 0.79 |
|---|---|---|---|---|---|
| YKL-40 | 0.04 | 0.06 | 0.81 | 0.49 | 0.28 |
| $\beta_2$M | 0.02 | 0.91 | 0.44 | 0.52 | 0.14 |
| $\alpha_1$M | 0.02 | 0.21 | 0.05 | 0.24 | 0.50 |
| Uromodulin | 0.02 | 0.0005 | 0.89 | 0.08 | 0.90 |

ACR = albumin-creatinine ratio;
$\alpha_1$M = $\alpha_1$-microglobulin;
$\beta_2$M = $\beta_2$-microglobulin;
CKD = chronic kidney disease;
IL-18 = interleukin-18;
KIM-1 = kidney injury molecule-1;
MCP-1 = monocyte chemoattractant protein-1;
NGAL = neutrophil gelatinase-associated lipocalin;
SPRINT = Systolic Blood Pressure Intervention Trial;
YKL-40 = anti-chitinase-3-like protein 1.
*Changes estimated from linear models with $\log_2$ (biomarker) as the outcome. All models except those for ACR adjust for $\log_2$-transformed urinary creatinine concentrations. All models adjust for baseline systolic blood pressure.

At 1 year, the cases in the standard arm had higher concentrations of all nine biomarkers compared with cases in the intensive arm but was only statistically significant for YKL-40 (p=0.01) (Appendix Table 6). We compared the 1-year relative changes of each biomarker between incident CKD cases in the intensive vs. standard arms, adjusting for baseline SBP and urine creatinine, and found significant differences for ACR, $\beta$2M, $\alpha$1m, YKL-40, and uromodulin (FIG. 1). All five of these biomarkers were decreased at 1 year among cases in the intensive arm and either increased or remained unchanged among cases in the standard arm.

To determine whether use of renin-angiotensin-aldosterone system inhibitors influenced the ACR declines, we stratified the intensive arm cases by users (N=90) and non-users (N=19) of angiotensin converting enzyme inhibitors or angiotensin receptor blockers during follow-up until CKD diagnosis. The median (IQR) reduction in ACR was near unity among these two groups [−33% (−66% to +25%) vs.-46% (−86% to +41%), respectively]. Among standard arm cases, the change in ACR differed substantially by use of these medications: −16% (−68% to +44%) among the 23 users vs. +85% (+54% to +159%) among the 10 non-users.

Discussion

In this case-control study nested within a trial of hypertensive participants without CKD at baseline, we used a diverse panel of urinary biomarkers to characterize intrinsic kidney damage among incident CKD cases in the setting of intensive blood pressure reduction to SBP<120 mmHg. Our findings demonstrate that, despite their substantial eGFR declines in the first year of SPRINT, incident CKD cases in the setting of intensive blood pressure lowering were not characterized by intrinsic kidney damage and rather had less injury overall than matched controls without CKD. In contrast, cases of incident CKD in the standard arm of the trial had relative elevations of 5 of the 9 biomarkers we evaluated, compared with intensive arm cases. These data support the notion that eGFR declines in the setting of intensive blood pressure lowering are generally manifestations of benign changes in renal blood flow.

Although participants did not have clinically diagnosed CKD at baseline, we found that baseline concentrations of urinary ACR, KIM-1 and MCP-1 were associated with the development of incident CKD during follow-up. Compared with their respective controls, baseline characteristics of the future incident CKD cases were otherwise distinguished only by higher SBP. These findings suggest that urinary biomarkers may identify individuals with sub-clinical kidney injury who may be at increased risk for subsequent eGFR changes. These findings are consistent with studies in other settings that reported associations of ACR, KIM-1, and MCP-1 with incident CKD and kidney function decline. (15-17)

Our comparisons of 1-year biomarker changes are also consistent with prior clinical trials reporting the distinct associations of eGFR declines from intensive vs. standard SBP management with cardiovascular disease and mortality. (18-22) For example, a post hoc analysis of the Secondary Prevention of Small Subcortical Strokes (SPS3) trial found that early eGFR declines within the intensive SBP reduction arm were not associated with adverse cardiovascular outcomes, in contrast to eGFR declines within the standard care arm, which portended higher cardiovascular risk. (23) Similarly, analyses of the MDRD and African American Study of Kidney Disease and Hypertension (AASK) trials found that participants randomized to more intensive SBP lowering had initial elevations in creatinine but lower long-term mortality risk, compared to those randomized to less intensive management. (24, 25) These investigators hypothesized that blood pressure treatment lowers renal blood flow and reduces hydrostatic pressure gradients across the glomerular capillaries, in turn benignly decreasing creatinine clearance and eGFR. Building upon these findings, our results suggest that blood pressure lowering may even alleviate hypertensive kidney injury, regardless of changes in serum creatinine.

Although we measured a panel of biomarkers to broadly characterize kidney damage, it is important to highlight the unique physiological domains that these biomarkers represent. For example, ACR, $\alpha$1m, and $\beta$2m, systemic proteins that are freely filtered at the glomerulus and reabsorbed by the proximal tubules, significantly decreased in the intensive vs. standard arm cases at 1 year. (26-28) These relative declines among cases in the intensive arm may be a direct reflection of reduced renal blood flow and glomerular filtration in the setting of intensive blood pressure lowering, independent of renin-angiotensin-aldosterone system inhibitor use. In contrast, the relative elevations among standard arm cases may represent impaired tubular absorption of these proteins, a manifestation of true intrinsic kidney damage.

The other 6 biomarkers are largely produced within the kidney and released into urine, and two of these biomarkers differed significantly in the case vs. case comparisons: YKL-40 and uromodulin decreased in the intensive arm cases and remained unaltered or increased in the standard arm cases. YKL-40 is largely produced by kidney tubular cells and signifies kidney tubular injury and repair. (29, 30) The relative declines of YKL-40 suggest that incident CKD cases in the setting of intensive blood pressure lowering have less tubular damage compared with matched controls and with cases in the standard arm. However, this pattern was not observed for other traditional markers of tubule injury (IL-18, KIM-1, NGAL, and MCP-1).

The relative declines of uromodulin among intensive arm cases that significantly differed from elevations among standard arm cases were unexpected. Uromodulin, which is produced in the thick ascending limb of Henle's loop and the distal tubule and is believed to protect against CKD. When measured at a single timepoint, higher uromodulin has been associated with less CKD progression in prior studies, (31) although baseline uromodulin was not associated with odds of incident CKD in this study. Thus, we expected to observe relative elevations in uromodulin among intensive arm cases. However, dynamic changes in uromodulin have not been evaluated in prior studies. It is possible that lower renal blood flow may lead to decreased requirement for uromodulin production and/or secretion. Nonetheless, we acknowledge that this finding may be discrepant with our overall hypotheses. Future studies are necessary to examine the dynamic changes of uromodulin in response to treatments that influence kidney health and its association with outcomes.

Strengths of this study include the matched case-control design in a randomized trial setting that minimized potential confounding. The SPRINT cohort involved 102 centers across the U.S. and Puerto Rico, had close follow-up of participants, and frequent creatinine measurements and longitudinal urine samples, which provided a unique opportunity to investigate kidney changes in the context of intensive blood pressure reduction.

We also acknowledge several important limitations. While the biomarker results exhibit an overall consistent pattern, we are unable to explain the biological mechanisms of some of the specific changes. For example, KIM-1 and NGAL were significantly increased in a similar magnitude in case versus control comparisons. We are uncertain why these biomarkers would increase during follow-up, and no prior study to our knowledge has measured them repeatedly in a similar cohort. In addition, our study lacked power to compare cases and controls within the standard arm, as only 34 incident CKD cases occurred in this arm. This may explain the absence of significant differences of baseline biomarkers with incident CKD in the standard arm and of significant differences in the 1-year changes between cases and controls in this arm. Because we measured biomarkers only at baseline and at year 1, we do not have biomarker concentrations from the precise time of CKD diagnosis. The majority of incident CKD endpoints occurred after the 1 year biomarker measurements; thus, concentrations may have been different if measured at the time of incident CKD diagnosis. However, the mean eGFR decline at 1 year was significantly larger among cases vs. controls in the intensive arm (20 vs. 4 mL/min/1.73 m$^2$) and in the standard arm (16 vs. 0 mL/min/1.73 m$^2$), so the eGFR had already declined substantially among the CKD cases at the time of biomarker measurement. If the substantial eGFR declines found among incident CKD cases in the intervention arm had been associated with intrinsic kidney injury, we should have detected elevations in biomarker concentrations at 1 year. Finally, our findings may not be generalizable to all hypertensive persons, particularly to those with diabetes or proteinuria >1 gram/day, as such persons were excluded from SPRINT.

Two important and distinct roles for urinary biomarkers emerge from our findings: identifying persons susceptible to CKD using the baseline concentrations; and using changes in the biomarkers to evaluate longitudinal changes in kidney health. The biomarkers that provided baseline prediction of CKD, a potential proxy of kidney reserve, were not the same as those that reflect responses to blood pressure changes. An eventual biomarker panel in clinical care will warrant a collection of proteins that achieve both of these objectives. Future work should investigate whether urinary biomarkers can prognosticate and distinguish individuals with true tubular injury accompanying eGFR changes in CKD, similar to their use in acute kidney injury. (32, 33)

In conclusion, the perception of a trade-off between cardiovascular benefits and kidney harms during intensive blood pressure lowering may be misguided. We found that incident CKD cases in the setting of intensive SBP treatment did not have elevations in biomarkers of kidney damage in the first year of treatment and, instead, had relative declines in several biomarkers compared both with matched controls and with incident CKD cases in the standard arm. These findings suggest that eGFR declines observed in the setting of intensive blood pressure lowering are mostly hemodynamic in nature, even among patients who may be inappropriately labeled as having a new diagnosis of CKD. We also demonstrate the limitations of serum creatinine and the potential utility of urinary biomarkers for monitoring kidney health during hypertension treatment when changes in renal blood flow may confound the clinical interpretation of changes in serum creatinine. Ultimately, these findings, in conjunction with lower cardiovascular disease and mortality risk reported in SPRINT, should be reassuring for clinicians who embark on evidence-based intensive blood pressure lowering for their patients.

Example 2

This example describes the methods used in the study described in Example 1.

Study Design and Population

SPRINT was a randomized, controlled, open-label trial of intensive (targeting <120 mmHg) vs. standard (targeting <140 mmHg) SBP therapy among individuals at high cardiovascular risk and without diabetes. (4) A total of 9,361 participants were enrolled between November 2010 and March 2013 at 102 sites in the U.S. and Puerto Rico. Among these, 2,646 participants (28%) had baseline CKD, defined as an eGFR <60 ml/min/1.73 m$^2$ by the Modification of Diet in Renal Disease (MDRD) equation. Full details of the study protocols are published elsewhere. (6)

Among participants without CKD at baseline, the SPRINT protocol defined incident CKD as >30% reduction from baseline in eGFR defined by the MDRD equation and eGFR <60 ml/min/1.73 m$^2$ confirmed on two serial eGFR measurements at least 3 months apart. Over SPRINT follow-up of a median of 3.26 years, there were 162 participants who developed incident CKD: 128 in the intensive arm and 34 in the standard arm. Among these 162 incident CKD cases, 26.5% (N=43) had been diagnosed by the 1-year follow-up visit, whereas the remaining cases were diagnosed subsequently. In the SPRINT Kidney Tubule Health ancillary project, we defined baseline CKD using the CKD Epidemiology Collaboration (CKD-EPI) equation with both cystatin C and creatinine (resulting in 2,503 cases of baseline CKD), which accounts for the modest difference between the number of incident CKD cases in our study (N=162) relative to the original publication (N=154). For each incident CKD case, we used prevalent control sampling to select one matched control that had not developed CKD at the end of follow-up. We used a hierarchical matching scheme prioritizing the following factors in order: randomization arm, age (within 5 years), sex, race, and baseline eGFR (within 5 ml/min/1.73 m²) to account for these potential confounders. There was 1 control in which race could not be matched following matching on randomization drift. Most biomarkers were measured simultaneously using multiplex immunoassays from Meso Scale Discovery (MSD, Gaithersburg, MD), except for α1m, which was measured using the BN II Nephelometer assay (Siemens, Newark, DE). Urine creatinine was measured using a Cobas c311 clinical analyzer (Roche Diagnostics, Indianapolis, IN). Details regarding assay methods are shown in Appendix Tables 1 and 2. Biomarker concentrations below the lower limit of detection were imputed with a value calculated from subtracting a small number from the limit of detection. Laboratory personnel were blinded to clinical information about the participants, and specimens were evaluated in random order. With the exception of urinary ACR and α1m, all biomarkers were measured in duplicate and results were averaged to improve precision.

APPENDIX TABLE 1

Appendix Table 1. Urinary Biomarker Assay Information for MSD Multiplex Panels

| Assays | Dilution | Standard Range | Minimum Detectable Concentration | Manufacturer-Defined "Normal" Range |
|---|---|---|---|---|
| Albumin | 1:251 | 0.0488-200 ng/mL | 0.141 ng/mL | Undetectable-48 757 ng/mL |
| IL-18 | 1:10 | 0.64-10 000 pg/mL | 0.161 pg/mL | NA |
| KIM-1 | 1:10 | 1.28-20 000 pg/mL | 0.19 pg/mL | NA |
| NGAL | 1:251 | 0.0024-10.00 ng/mL | 0.0029 ng/mL | 4.20-225.00 ng/mL |
| MCP-1 | 1:10 | 0.64-10 000 pg/mL | 0.071 pg/mL | 1.95-1173 pg/mL |
| YKL-40 | 1:10 | 3.20-50 000 pg/mL | 0.346 pg/mL | NA |
| β2M | 1:251 | 0.0049-20.00 ng/mL | 0.0061 ng/mL | 38.00-1130.00 ng/mL |
| Uromodulin | 1:251 | 0.0244-100.00 ng/mL | 0.026 ng/mL | 347.00-7846.00 ng/mL |

β2M = β2-microglobulin;
CKD = chronic kidney disease,
IL-18 = interleukin-18;
KIM-1 = kidney injury molecule-1;
MCP-1 = monocyte chemoattrac-tant protein-1;
MSD = Meso Scale Discovery;
NA = not available;
NGAL = neutrophil gelatinase-associated lipocalin;
YKL-40 = anti-chitinase-3-like protein 1.

arm, eGFR, and age. The SPRINT Research Group approved the study protocol, which was adherent to the Declaration of Helsinki.

Urinary Kidney Damage Biomarker Measurements

Our biomarker panel included the following nine urinary biomarkers:albumin-creatinine ratio (ACR), interleukin-18 (IL-18), kidney injury molecule-1 (KIM-1), neutrophil gelatinase-associated lipocalin (NGAL), monocyte chemoattractant protein-1 (MCP-1), chitinase-3-like protein 1 (YKL-40), beta-2 microglobulin (β2M), alpha-1 microglobulin (α1M), and uromodulin (UMOD). These proteins have been well-studied in kidney disease as direct markers of kidney damage, particularly in the settings of drug nephrotoxocity (7, 8) and acute kidney injury. (9-11) Broadly, the biomarkers reflect glomerular injury (ACR), tubular injury and fibrosis (IL-18, KIM-1, NGAL, MCP-1), tubular injury repair (YKL-40), proximal tubular dysfunction (β2M, α1m), and loop of Henle protein production (uromodulin).

We used urine specimens that were collected from cases and controls at randomization (baseline) and at the 1-year follow-up visit. All specimens were in continuous storage at −80° C. without previous freeze-thaw until measurement. Biomarkers were measured at the University of Vermont Laboratory for Clinical Biochemistry Research. Urinary biomarkers from both baseline and 1 year were measured contemporaneously to minimize influence of laboratory

APPENDIX TABLE 2

Appendix Table 2. Urinary Biomarker Assay Information for Non-MSD Assays

| Assay | Instrument | Method | Detectable Range |
|---|---|---|---|
| α₁M | BN II nephelometer | Immunochemical | 5-80 mg/L |
| Creatinine | Cobas c 311 | Enzymatic | 1.1-610 mg/dL |

α₁M = α₁-microglobulin;
MSD = Meso Scale Discovery

Covariates

In addition to matching factors, covariates examined included baseline and 1-year SBP and diastolic blood pressure (DBP); number of anti-hypertensive medications; angiotensin-converting enzyme inhibitor or angiotensin receptor blocker use; and baseline total cholesterol and high-density lipoprotein cholesterol concentrations, body mass index, history of clinical cardiovascular disease, history of chronic heart failure, and smoking status. Covariates were selected based on evidence from prior studies (12) and were collected as part of the parent trial. Our pre-specified analytic plan included statistical adjustments for baseline covariates that differed between cases and controls within each intervention arm.

Statistical Methods

We first summarized baseline characteristics in cases and matched controls, stratified by intervention arm, and tested for differences using univariate conditional logistic regression models. We next compared baseline biomarker concentrations between incident CKD cases and matched controls in our overall study sample, as well as stratified by intervention arm, by fitting separate conditional logistic regression models for each biomarker with adjustment for baseline SBP and urine creatinine. Due to their skewed distributions, biomarker concentrations were summarized using geometric mean and standard errors. All models except those for ACR were adjusted for log 2-transformed urine creatinine concentrations to account for urine tonicity. We assessed the potential for bias due to the choice of prevalent control sampling at the end of follow-up rather than incidence-density sampling. To account these potential control selection biases, we employed the semi-parametric weighted estimator proposed by Landsman and Graubard. (13) We then re-calculated associations between biomarkers at baseline and case-control status using the sample weights.

We next compared 1-year changes in each biomarker between cases and controls, stratified by intervention arm. We also compared 1-year changes between incident CKD cases in the intensive and standard arms. Although comparing controls between intervention arms was not part of our pre-specified analytic plan, these data have been included for completeness. We examined 1-year changes by modeling the difference (1-year minus baseline) in log 2-transformed biomarker concentrations using linear mixed-effect models, adjusting for baseline SBP and both linear and quadratic terms for log 2-transformed urine creatinine concentrations. To account for the matched study design, we included case-control pair ID as a random effect and adjusted for the matching variables (age, race, sex, and eGFR). Only subjects with complete data for case-control pairs were used in these analyses, which resulted in varying samples sizes across the biomarkers. Predicted (least-squares) means of the change in biomarker and associated 95% confidence intervals were back-transformed to estimate the mean ratio of 1-year to baseline levels. Associated Wald tests for differences in the predicted mean changes were used to test significance. The mean changes in each biomarker and the comparisons between groups were presented graphically for ease of communication. We used an interaction term to evaluate whether relative biomarker changes between cases and controls were statistically different comparing the intervention and standard arms.

P-values <0.05 were considered statistically significant for all analyses without adjustment for multiple comparisons, as biomarkers were hypothesized to be mutually reinforcing rather than a series of independent tests. (14) All analyses were performed using SAS® version 9.4 software (SAS Institute, Cary, NC), in particular the LOGISTIC® procedure for conditional logistic regression analyses and the MIXED® procedure for linear mixed-effects models.
Table Descriptions Table 1 lists baseline and year 1 characteristics among incident CKD cases and matched controls stratified by randomization arm, in SPRINT. Data are presented as mean±standard deviation for continuous variables and frequency (%) for categorical variables. *P-values from univariate conditional logistic regression model. †Matching factor, no test performed. ‡Year 1 number of case/control pairs for Intensive Arm: serum creatinine, eGFR-N=123; SBP, DBP, ACE-inhibitor use, ARB use, number of anti-hypertensive medications-N=124. Standard Arm: serum creatinine, eGFR-N=33; SBP, DBP, ACE-inhibitor use, ARB use, number of anti-hypertensive medications-N=34. eGFR=estimated glomerular filtration rate;

MDRD=Modification of Diet in Renal Disease study equation; CKD-EPI=Chronic Kidney Disease Epidemiology Collaboration equation; SBP=systolic blood pressure; DBP=diastolic blood pressure; HDL=high density lipoprotein; CVD=cardiovascular disease; CHF=congestive heart failure; ACE=angiotensin-converting enzyme; ARB=angiotensin receptor blocker.

Table 2 lists baseline biomarker concentrations among incident CKD cases and matched controls among SPRINT participants in both randomization arms combined. *Odds Ratio (OR) per standard deviation increase in log 2-transformed biomarker concentrations. All models except for albumin-creatinine ratio adjust for log 2-transformed urine creatinine concentrations. All models adjust for baseline systolic blood pressure. Data presented as geometric means±standard error of the mean (SEM). Full names for each urinary biomarker are as follows: albumin-creatinine ratio (ACR), interleukin-18 (IL-18), kidney injury molecule-1 (KIM-1), neutrophil gelatinase-associated lipocalin (NGAL), monocyte chemoattractant protein-1 (MCP-1), chitinase-3-like protein 1 (YKL-40), beta-2 microglobulin (β2M), α1-microglobulin (α1M), and uromodulin (UMOD).

Appendix Table 1 lists urinary biomarker assay information for Meso Scale Discovery (MSD) multiplex panels.

Appendix Table 2 lists urinary biomarker assay information for non-MSD assays. Full names for each urinary biomarker are as follows: albumin-creatinine ratio (ACR), interleukin-18 (IL-18), kidney injury molecule-1 (KIM-1), neutrophil gelatinase-associated lipocalin (NGAL), monocyte chemoattractant protein-1 (MCP-1), chitinase-3-like protein 1 (YKL-40), beta-2 microglobulin (β2M), α1-microglobulin (α1M), and uromodulin (UMOD).

Appendix Table 3 lists Spearman correlations of baseline biomarker concentrations. Full names for each urinary biomarker are as follows: albumin-creatinine ratio (ACR), interleukin-18 (IL-18), kidney injury molecule-1 (KIM-1), neutrophil gelatinase-associated lipocalin (NGAL), monocyte chemoattractant protein-1 (MCP-1), chitinase-3-like protein 1 (YKL-40), beta-2 microglobulin (β2M), α1-microglobulin (α1M), and uromodulin (UMOD).

Appendix Table 4 lists baseline biomarker concentrations among incident CKD cases and matched controls among SPRINT participants in both randomization arms combined, comparison of results of unweighted and weighted logistic regression (LR) analyses. *Odds Ratio (OR) per standard deviation increase in log 2-transformed biomarker concentrations. All models except for albumin-creatinine ratio adjust for log 2-transformed urine creatinine concentrations. All models adjust for baseline systolic blood pressure. Data presented as geometric means±standard error of the mean (SEM). Full names for each urinary biomarker are as follows: albumin-creatinine ratio (ACR), interleukin-18 (IL-18), kidney injury molecule-1 (KIM-1), neutrophil gelatinase-associated lipocalin (NGAL), monocyte chemoattractant protein-1 (MCP-1), chitinase-3-like protein 1 (YKL-40), beta-2 microglobulin (β2M), α1-microglobulin (α1M), and uromodulin (UMOD).

Appendix Table 5 lists baseline biomarker concentrations among incident CKD cases and matched controls, stratified by intervention arm, in SPRINT*Odds Ratio (OR) based on standard deviation increase in log 2-transformed biomarker concentrations. All models except those for albumin-creatinine ratio adjust for log 2-transformed urine creatinine concentrations. All models adjust for baseline systolic blood pressure. Data presented as geometric means±standard error of the mean (SEM). Full names for each urinary biomarker are as follows: albumin-creatinine ratio (ACR), interleukin- 18 (IL-18), kidney injury molecule-1 (KIM-1), neutrophil gelatinase-associated lipocalin (NGAL), monocyte chemoattractant protein-1 (MCP-1), anti-chitinase-3-like protein 1 (YKL-40), beta-2 microglobulin (32M), α1-microglobulin (α1M), and uromodulin (UMOD).

Appendix Table 6 lists one-year biomarker concentrations among incident CKD cases and matched controls, overall and stratified by intervention arm, in SPRINT. Data presented as geometric means±standard error of the mean (SEM). Full names for each urinary biomarker are as follows: albumin-creatinine ratio (ACR), interleukin-18 (IL-18), kidney injury molecule-1 (KIM-1), neutrophil gelatinase-associated lipocalin (NGAL), monocyte chemoattractant protein-1 (MCP-1), chitinase-3-like protein 1 (YKL-40), beta-2 microglobulin (β2M), α1-microglobulin (α1M), and uromodulin (UMOD).

Appendix Table 7 lists 1-year changes in biomarker concentrations among incident CKD cases and matched controls, stratified by randomization arm, in SPRINT*Changes estimated from linear mixed models with $\log_2$ (biomarker) as the outcome. All models except those for albumin-creatinine ratio adjust for log 2-transformed urine creatinine concentrations. All models adjust for baseline systolic blood pressure. Full names for each urinary biomarker are as follows: albumin-creatinine ratio (ACR), interleukin-18 (IL-18), kidney injury molecule-1 (KIM-1), neutrophil gelatinase-associated lipocalin (NGAL), monocyte chemoattractant protein-1 (MCP-1), chitinase-3-like protein 1 (YKL-40), beta-2 microglobulin (β2M), α1-microglobulin (α1M), and uromodulin (UMOD).

Example 3

This example demonstrates urinary biomarkers of kidney damage and incident CKD in SPRINT.

Background: Randomization to the intensive arm (SBP<120 mmHg) in SPRINT was associated with a 3-fold increased incidence of CKD, compared with the standard arm (SBP<140 mmHg). However, it is unknown whether incident CKD in the setting of intensive SBP lowering is accompanied by intrinsic kidney injury.

Methods: Among the 162 incident CKD cases (128 in the intensive arm and 34 in the standard arm) that occurred during SPRINT follow-up and 162 controls matched on age, sex, race, baseline eGFR, and randomization arm, we measured 9 urinary biomarkers of kidney damage at baseline and 1 year. Linear mixed-effects models adjusting for baseline SBP and urine creatinine estimated 1-year biomarker changes to compare incident CKD cases vs. matched controls in the intensive arm; and to contrast cases in the intensive vs. standard arms.

Results: At 1 year, cases in the intensive arm had significant eGFR declines, compared with matched controls (−22 vs.−4 mL/min/1.73 m$^2$; p<0.0001). Incident CKD cases in the intensive arm had either significantly greater 1-year reductions or similar patterns of kidney damage biomarkers, compared with both matched controls and with cases in the standard arm (FIG. 1).

Conclusions: Incident CKD cases in the intensive arm had substantial 1-year eGFR reductions yet did not have relative increases in biomarkers of kidney damage, compared with matched controls; rather, these cases had decreases in several of these biomarkers, compared with both matched controls and cases in the standard arm. Thus, incident CKD in the setting of intensive SBP lowering may reflect hemodynamic accommodation rather than intrinsic injury, providing reassuring evidence clinicians who embark on evidence-based blood pressure lowering for their patients.

Example 4

This example describes a study to determine associations of additional markers at baseline reflecting the complexity of kidney tubules with risk for mortality, CKD progression, CVD and AKI among SPRINT-CKD participants. The markers of tubule secretion (fractional excretion of tiglylglycine, isovalerylglycine, hippuric acid, suberic acid, phenylacetylglutamine and cinnamoylglycine), urine NH4+, serum uromodulin, serum KIM-1, serum sTNFR1 & sTNFR2, urine trefoil factor 3, and clusterin are evaluated in this study.

A pilot study was carried out to (1) demonstrate that tubule secretion markers (hippuric acid, isovalerylglycine, phenylacetylglutamine, triglycine, cinnamoylglycine and suberric acid) could be measured with high precision (via LC-MS/MS) in both blood and urine in SPRINT specimens, (2) evaluate whether there were marked diurnal changes in endogenous secretion markers over 24 hours, and (3) compare the similarity of secretion estimates in spot vs. 24 hour urine specimens. 21 specimens were selected from SPRINT participants at our center to represent the full spectrum of eGFR and it was found all 6 secretion markers with good precision (Coefficients of Variation [CVs] between 8-14%.

| Analytes | Plasma | Urine | Coefficient of Variation (%) |
|---|---|---|---|
| 1. hippuric acid | x | x | 9.0 |
| 2. isovalerylglycine | x | x | 8.0 |
| 3. phenylacetylglutamine | x | x | 11.0 |
| 4. triglycine | x | x | 9.4 |
| 5. cinnamoylglycine | x | x | 12.6 |
| 6. suberric acid | x | x | 14.0 |

| Comparison of Tubule Secretion in 24 Hr. vs. Spot Urine Specimens*[23] | | |
|---|---|---|
| Metabolite | 24 Hr. Urine Fractional Excretion | Spot Urine Fractional Excretion |
| Tiglylglycine | 1019% | 1036% |
| Isovalerylglycine | 947% | 1024% |
| Hippuric acid | 746% | 715% |
| Suberic acid | 220% | 186% |
| Cinnamoylglycine | 218% | 318% |

*Percentages reflect renal clearance relative to creatinine (i.e. % greater clearance than GFR).

The measurement of the 6 markers of secretion in blood and urine in SPRINT is carried out and then examined for a relationship with CKD progression, acute kidney injury (AKI), cardiovascular disease (CVD) events, and mortality in this study. These measures are made at baseline among the 2,514 individuals with CKD and therefore are expected to have 100% overlap with baseline biomarkers. Currently, follow-up for these events is available through the end of the SPRINT trial (Aug. 20, 2015), during which the SPRINT-CKD subset experienced 87 CKD progression events (50% decline in eGFR, dialysis, or transplantation), 184 hospitalized AKI events, 306 CVD events, and 233 all-cause deaths. The secretion markers for this study are measured in paired blood and urine by liquid chromatography-tandem mass spectrometry (LC-MS/MS) using the procedures utilized in Garimella et al., Am J Kidney Disease 69:709-711 (2017).

Method validation is conducted following the FDA guidance for bioanalytical assays including assessment of method performance utilizing quality control (QC) samples as a measure of accuracy and precision. Ion-exchange chromatography is employed for the analytical separation using a Millipore Sigma apHera™ amino (NH2) column (5 micron, 15 cm×2 mm). The secretion metabolites and internal standards are detected using scheduled multiple reaction monitoring (sMRM) and polarity switching to utilize both positive and negative ionization modes in a single run.

In addition to the above 6 markers, urine $NH4^+$ a marker of acid base is also measured from samples via a straightforward glutamate dehydrogenase assay on a standard clinical chemistry analyzer. In a pilot study, urine ammonia had a coefficient of variation of 4.6%.

In a pilot study, serum UMOD, a marker of kidney immune defense, was measured and demonstrated a coefficient of variation of 7.8%. Plasma UMOD was measured in samples obtained from stable kidney transplant recipients who participated in the FAVORIT trial. Associations of plasma UMOD with kidney allograft failure events was evaluated. Participants had mean eGFR of 46±18 ml/min/1.73 $m^2$ at baseline. During follow-up, there were 226 kidney allograft failure events. It was found that persons with more advanced CKD had lower plasma UMOD levels at baseline. Moreover, lower plasma UMOD was strongly associated with allograft failure, independent of baseline eGFR, ACR, or other risk factors (HR low vs. high tertile 2.00; 95% CI 1.06, 3.77). Plasma UMOD is measured using an ELISA (Euroimmun Inc).

Plasma concentrations of sTNFR-1, sTNFR-2, and KIM-1 (markers of inflammatory response) are measured using 96-well multiplex assays from MESO scale Diagnostics (MSD)®; the MSD platform has been previously used and excellent results were yielded. For the proximal tubule damage markers, urine TFF3 and clusterin are also measured by multi-plex immunoassay on the MSD platform. TFF3 and clusterin are measured using the same multiplex MSD immunoassay. The coefficients of variation are provided in the table below.

| Analytes | Plasma | Urine | Coefficient of Variation (%) |
|---|---|---|---|
| Soluble TNFR-1 | x | | 10.0 |
| Soluble TNFR-2 | x | | 9.3 |
| KIM-1 | x | | 10.5 |
| TFF3 | | x | 10.5 |
| Clusterin | | x | 9.0 |

REFERENCES

The following references are cited throughout the background and examples by the number indicated below.

1. Vasan R S, Larson M G, Leip E P, Evans J C, O'Donnell C J, Kannel W B, et al. Impact of High-Normal Blood Pressure on the Risk of Cardiovascular Disease. New England Journal of Medicine. 2001; 345(18):1291-7.
2. Sipahi I, Tuzcu E M, Schoenhagen P, Wolski K E, Nicholls S J, Balog C, et al. Effects of Normal, Pre-Hypertensive, and Hypertensive Blood Pressure Levels on Progression of Coronary Atherosclerosis. Journal of the American College of Cardiology. 2006; 48(4):833-8.
3. Lewington S C R, Qizilbash N, Peto R, Collins R; Prospective Studies Collaboration. Age-specific relevance of usual blood pressure to vascular mortality: a meta-analysis of individual data for one million adults in 61 prospective studies. The Lancet; 360(9349):1903-13.
4. A Randomized Trial of Intensive versus Standard Blood-Pressure Control. New England Journal of Medicine. 2015; 373(22):2103-16.
5. Whelton P K, Carey R M, Aronow W S, Casey D E, Collins K J, Dennison Himmelfarb C, et al. 2017 ACC/AHA/AAPA/ABC/ACPM/AGS/APhA/ASH/ASPC/NMA/PCNA Guideline for the Prevention, Detection, Evaluation, and Management of High Blood Pressure in Adults. A Report of the American College of Cardiology/American Heart Association Task Force on Clinical Practice Guidelines. Journal of the American College of Cardiology. 2017; 71(19):e127-e248.
6. Ambrosius W T, Sink K M, Foy C G, Berlowitz D R, Cheung A K, Cushman W C, et al. The design and rationale of a multicenter clinical trial comparing two strategies for control of systolic blood pressure: The Systolic Blood Pressure Intervention Trial (SPRINT). Clinical Trials. 2014; 11(5):532-46.
7. Bonventre J V, Vaidya V S, Schmouder R, Feig P, Dieterle F. Next-generation biomarkers for detecting kidney toxicity. Nat Biotech. 2010; 28(5):436-40.
8. Blank M, Felice A D, Goodsaid F, Harlow P, Hausner E, Jacobson-Kram D, et al. 2009; Pages. Accessed at Center for Drug Evaluation and Research U.S. Food and Drug Administration at www.fda.gov/downloads/drugs/developmentapprovalprocess/drugdevelopmenttoolsqualificationprogram/ucm382536.pdf on February 2018.
9. Endre Z H, Westhuyzen J. Early detection of acute kidney injury: Emerging new biomarkers (Review Article). Nephrology. 2008; 13(2):91-8.
10. Parikh C R, Devarajan P. New biomarkers of acute kidney injury. Critical Care Medicine. 2008; 36(4):S159-S65.
11. Vaidya V S, Ferguson M A, Bonventre J V. Biomarkers of Acute Kidney Injury. Annual review of pharmacology and toxicology. 2008; 48:463-93.
12. Kazancioğlu R. Risk factors for chronic kidney disease: an update. Kidney International Supplements. 2013; 3(4):368-71.
13. Landsman V, Graubard B I. Efficient analysis of case-control studies with sample weights. Statistics in Medicine. 2013; 32(2):347-60.
14. Bacchetti P. Peer review of statistics in medical research: the other problem. BMJ. 2002; 324(7348):1271-3.
15. Peralta C A, Katz R, Bonventre J V, Sabbisetti V, Siscovick D, Sarnak M, et al. Associations of Urinary Levels of Kidney Injury Molecule-1 (KIM-1) and Neutrophil Gelatinase-Associated Lipocalin (NGAL) With Kidney Function Decline in the Multi-Ethnic Study of Atherosclerosis (MESA). American journal of kidney diseases: the official journal of the National Kidney Foundation. 2012; 60(6):904-11.
16. Shastri S, Katz R, Shlipak M, Kestenbaum B, Peralta C A, Kramer H, et al. Cystatin C and Albuminuria as Risk Factors for Development of CKD Stage 3: The Multi-Ethnic Study of Atherosclerosis (MESA). American journal of kidney diseases: the official journal of the National Kidney Foundation. 2011; 57(6):832-40.
17. Nadkarni G N, Rao V, Ismail-Beigi F, Fonseca V A, Shah S V, Simonson M S, et al. Association of Urinary Biomarkers of Inflammation, Injury, and Fibrosis with Renal Function Decline: The ACCORD Trial. Clinical Journal of the American Society of Nephrology: CJASN. 2016; 11(8):1343-52.

18. Wright, Jr J T, Bakris G, Greene T, et al. Effect of blood pressure lowering and antihypertensive drug class on progression of hypertensive kidney disease: Results from the AASK trial. JAMA. 2002; 288(19):2421-31.

19. Klahr S, Levey A S, Beck G J, Caggiula A W, Hunsicker L, Kusek J W, et al. The Effects of Dietary Protein Restriction and Blood-Pressure Control on the Progression of Chronic Renal Disease. New England Journal of Medicine. 1994; 330(13):877-84.

20. Blood-pressure targets in patients with recent lacunar stroke: the SPS3 randomised trial. The Lancet; 382 (9891):507-15.

21. Effects of Intensive Blood-Pressure Control in Type 2 Diabetes Mellitus. New England Journal of Medicine. 2010; 362(17):1575-85.

22. Appel L J, Wright J T J, Greene T, Agodoa L Y, Astor B C, Bakris G L, et al. Intensive Blood-Pressure Control in Hypertensive Chronic Kidney Disease. New England Journal of Medicine. 2010; 363(10):918-29.

23. Peralta C A, McClure L A, Scherzer R, Odden M C, White C L, Shlipak M, et al. Effect of Intensive Versus Usual Blood Pressure Control on Kidney Function Among Individuals With Prior Lacunar Stroke: A Post Hoc Analysis of the Secondary Prevention of Small Subcortical Strokes (SPS3) Randomized Trial. Circulation. 2016; 133(6):584-91.

24. Ku E, Glidden D V, Johansen K L, Sarnak M, Tighiouart H, Grimes B, et al. Association between strict blood pressure control during chronic kidney disease and lower mortality after onset of end-stage renal disease. Kidney International; 87(5):1055-60.

25. Kimura T, Yasuda K, Yamamoto R, Soga T, Rakugi H, Hayashi T, et al. Identification of biomarkers for development of end-stage kidney disease in chronic kidney disease by metabolomic profiling. Scientific Reports. 2016; 6:26138.

26. Birn H, Christensen El. Renal albumin absorption in physiology and pathology. Kidney International. 2006; 69(3):440-9.

27. Penders J, Delanghe J R. Alpha 1-microglobulin: clinical laboratory aspects and applications. Clinica Chimica Acta. 2004; 346(2):107-18.

28. Argyropoulos C P, Chen S S, Ng Y-H, Roumelioti M-E, Shaffi K, Singh P P, et al. Rediscovering Beta-2 Microglobulin As a Biomarker across the Spectrum of Kidney Diseases. Frontiers in Medicine. 2017; 4:73.

29. Parikh C R, Mishra J, Thiessen-Philbrook H, Dursun B, Ma Q, Kelly C, et al. Urinary IL-18 is an early predictive biomarker of acute kidney injury after cardiac surgery. Kidney International. 2006; 70(1):199-203.

30. Schmidt I M, Hall I E, Kale S, Lee S, He C-H, Lee Y, et al. Chitinase-Like Protein Brp-39/YKL-40 Modulates the Renal Response to Ischemic Injury and Predicts Delayed Allograft Function. Journal of the American Society of Nephrology. 2013; 24(2):309-19.

31. El-Achkar™, Wu X-R. Uromodulin in Kidney Injury: An Instigator, Bystander, or Protector? American Journal of Kidney Diseases. 2012; 59(3):452-61.

32. Huen S C, Parikh C R. Molecular phenotyping of clinical AKI with novel urinary biomarkers. American Journal of Physiology-Renal Physiology. 2015; 309(5):F406-F13.

33. Siew E D, Ware L B, Ikizler T A. Biological Markers of Acute Kidney Injury. Journal of the American Society of Nephrology. 2011; 22(5):810-20.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed:

1. A method of treating a subject with hypertension, wherein the subject is on an intense hypertension treatment comprising an ACE inhibitor or an angiotensin II receptor blocker, wherein the subject was not known to have a kidney disease at the time hypertension treatment began, the method comprising (a) determining levels of Alpha-1 micro-globulin (α1m) and kidney injury molecule (KIM-1) in a urine sample from the subject receiving the hypertension treatment, and (b) decreasing the hypertension treatment when the levels of α1m and KIM-1 are increased in a urine sample obtained from the subject relative to a matched control subject known to have hypertension but has not been treated for hypertension.

2. The method of claim 1, wherein the subject has an estimated glomerular filtration rate (eGFR) greater than 60.

3. The method of claim 1, further comprising determining the subject's urine albumin:urine creatinine ratio (ACR).

4. The method of claim 1, further comprising measuring the level of at least one of the following protein biomarkers in the urine sample from the subject:
   i. neutrophil gelatinase associated lipocalin (NGAL);
   ii. Uromodulin (UMOD);
   iii. Interleukin-18 (IL-18)
   iv. Beta-2 microglobulin (β2m); and
   v. Monocyte chemoattractant protein-1 (MCP-1).

5. The method of claim 1, further comprising (i) measuring the subject's blood level of one or more of Soluble TNFR-1, Soluble TNFR-2, and UMOD, (ii) measuring the subject's urine level of TFF3 and/or clusterin, (iii) measuring the levels of hippuric acid, isovalerylglycine, pheylacetylglutamine, triglycine, cinnamoylglycine, suberric acid from a urine or blood sample obtained from the subject, (iv) measuring the subject's urine level ammonia, (v) measuring the level of blood creatinine, and optionally calculating the subject's estimated glomerular filtration rate, or (vi) a combination thereof.

* * * * *

SEQUENCE LISTING

```
<160> NUMBER OF SEQ ID NOS: 56

<210> SEQ ID NO 1
<211> LENGTH: 1450
<212> TYPE: PRT
<213> ORGANISM: Homo sapiens

<400> SEQUENCE: 1
```

```
Ala Thr Thr Gly Thr Gly Cys Thr Thr Gly Gly Cys Cys Ala Ala Thr
1               5                   10                  15

Gly Cys Cys Thr Cys Thr Thr Cys Thr Gly Ala Ala Gly Cys Ala Gly
                20                  25                  30

Cys Cys Ala Thr Cys Cys Cys Gly Gly Cys Cys Thr Cys Thr Thr Gly
        35                  40                  45

Gly Thr Ala Cys Thr Gly Cys Thr Gly Ala Cys Cys Cys Cys Ala Gly
    50                  55                  60

Cys Cys Ala Gly Gly Cys Thr Ala Cys Ala Gly Gly Ala Thr Cys
65                  70                  75                  80

Gly Ala Thr Thr Gly Gly Ala Gly Cys Thr Gly Thr Cys Cys Thr Thr
                85                  90                  95

Gly Gly Gly Gly Cys Thr Gly Thr Ala Ala Thr Thr Gly Gly Cys Cys
            100                 105                 110

Cys Cys Ala Gly Cys Thr Gly Ala Gly Cys Ala Gly Gly Gly Cys Ala
        115                 120                 125

Ala Ala Cys Ala Cys Thr Gly Ala Gly Gly Thr Cys Ala Ala Cys Thr
    130                 135                 140

Ala Cys Ala Ala Gly Cys Cys Ala Cys Ala Gly Gly Cys Cys Cys Cys
145                 150                 155                 160

Thr Thr Cys Cys Cys Cys Ala Gly Cys Cys Thr Cys Ala Gly Thr Thr
            165                 170                 175

Cys Ala Cys Ala Gly Cys Thr Gly Cys Cys Cys Thr Gly Thr Thr Gly
            180                 185                 190

Cys Ala Gly Gly Gly Ala Gly Gly Cys Gly Gly Thr Gly Gly Cys Cys
            195                 200                 205

Cys Thr Thr Cys Thr Gly Thr Thr Gly Cys Thr Ala Gly Ala Cys Cys
    210                 215                 220

Gly Ala Gly Cys Cys Thr Gly Thr Gly Gly Ala Thr Ala Thr Ala
225                 230                 235                 240

Cys Cys Ala Ala Gly Gly Cys Ala Gly Ala Gly Gly Ala Gly Cys Cys
            245                 250                 255

Cys Ala Thr Ala Gly Cys Cys Ala Thr Gly Ala Gly Gly Ala Gly Cys
        260                 265                 270

Cys Thr Cys Gly Gly Gly Gly Cys Cys Cys Thr Gly Cys Thr Cys Thr
    275                 280                 285

Thr Gly Cys Thr Gly Cys Thr Gly Ala Gly Cys Gly Cys Cys Thr Gly
    290                 295                 300

Cys Cys Thr Gly Gly Cys Gly Gly Thr Gly Ala Gly Cys Gly Cys Thr
305                 310                 315                 320

Gly Gly Cys Cys Cys Thr Gly Thr Gly Cys Cys Ala Ala Cys Gly Cys
            325                 330                 335

Cys Gly Cys Cys Cys Gly Ala Cys Ala Ala Cys Ala Thr Cys Cys Ala
        340                 345                 350

Ala Gly Thr Gly Cys Ala Gly Gly Ala Ala Ala Ala Cys Thr Thr Cys
    355                 360                 365

Ala Ala Thr Ala Thr Cys Thr Cys Thr Cys Gly Gly Ala Thr Cys Thr
    370                 375                 380

Ala Thr Gly Gly Gly Ala Ala Gly Thr Gly Gly Thr Ala Cys Ala Ala
385                 390                 395                 400

Cys Cys Thr Gly Gly Cys Cys Ala Thr Cys Gly Gly Thr Thr Cys Cys
            405                 410                 415
```

-continued

```
Ala Cys Cys Thr Gly Cys Cys Cys Thr Gly Gly Cys Thr Gly Ala
            420             425             430

Ala Gly Ala Ala Gly Ala Thr Cys Ala Thr Gly Gly Ala Cys Ala Gly
            435             440             445

Gly Ala Thr Gly Ala Cys Ala Gly Thr Gly Ala Gly Cys Ala Cys Gly
            450             455             460

Cys Thr Gly Gly Thr Gly Cys Thr Gly Gly Gly Ala Gly Ala Gly Gly
465             470             475             480

Gly Cys Gly Cys Thr Ala Cys Ala Gly Ala Gly Gly Cys Gly Gly Ala
            485             490             495

Gly Ala Thr Cys Ala Gly Cys Ala Thr Gly Ala Cys Cys Ala Gly Cys
            500             505             510

Ala Cys Thr Cys Gly Thr Thr Gly Gly Cys Gly Gly Ala Ala Ala Gly
            515             520             525

Gly Thr Gly Thr Cys Thr Gly Thr Gly Ala Gly Gly Ala Gly Ala Cys
            530             535             540

Gly Thr Cys Thr Gly Gly Ala Gly Cys Thr Thr Ala Thr Gly Ala Gly
545             550             555             560

Ala Ala Ala Ala Cys Ala Gly Ala Thr Ala Cys Thr Gly Ala Thr Gly
            565             570             575

Gly Gly Ala Ala Gly Thr Thr Thr Cys Thr Cys Thr Ala Thr Cys Ala
            580             585             590

Cys Ala Ala Ala Thr Cys Cys Ala Ala Ala Thr Gly Gly Ala Ala Cys
            595             600             605

Ala Thr Ala Ala Cys Cys Ala Thr Gly Gly Ala Gly Thr Cys Cys Thr
            610             615             620

Ala Thr Gly Thr Gly Gly Thr Cys Cys Ala Cys Ala Cys Cys Ala Ala
625             630             635             640

Cys Thr Ala Thr Gly Ala Thr Gly Ala Gly Thr Ala Thr Gly Cys Cys
            645             650             655

Ala Thr Thr Thr Thr Cys Cys Thr Gly Ala Cys Cys Ala Ala Gly Ala
            660             665             670

Ala Ala Thr Thr Cys Ala Gly Cys Cys Gly Cys Cys Ala Thr Cys Ala
            675             680             685

Thr Gly Gly Ala Cys Cys Cys Ala Cys Cys Ala Thr Thr Ala Cys Thr
            690             695             700

Gly Cys Cys Ala Ala Gly Cys Thr Cys Thr Ala Cys Gly Gly Gly Cys
705             710             715             720

Gly Gly Gly Cys Gly Cys Cys Gly Cys Ala Gly Cys Thr Gly Ala Gly
            725             730             735

Gly Gly Ala Ala Ala Cys Thr Cys Thr Cys Cys Thr Gly Cys Ala Gly
            740             745             750

Gly Ala Cys Thr Thr Cys Ala Gly Ala Gly Thr Gly Gly Thr Thr Gly
            755             760             765

Cys Cys Cys Ala Gly Gly Gly Thr Gly Thr Gly Gly Gly Cys Ala Thr
            770             775             780

Cys Cys Cys Thr Gly Ala Gly Gly Ala Cys Thr Cys Cys Ala Thr Cys
785             790             795             800

Thr Thr Cys Ala Cys Cys Ala Thr Gly Gly Cys Thr Gly Ala Cys Cys
            805             810             815

Gly Ala Gly Gly Thr Gly Ala Ala Thr Gly Thr Gly Thr Cys Cys Cys
            820             825             830

Thr Gly Gly Gly Gly Ala Gly Cys Ala Gly Gly Ala Ala Cys Cys Ala
```

-continued

```
              835              840              845

Gly Ala Gly Cys Cys Cys Ala Thr Cys Thr Thr Ala Ala Thr Cys Cys
    850              855              860

Cys Gly Ala Gly Ala Gly Thr Cys Cys Gly Gly Ala Gly Gly Gly Cys
865              870              875              880

Thr Gly Thr Gly Cys Thr Ala Cys Cys Cys Ala Ala Gly Ala Ala
                 885              890              895

Gly Ala Gly Gly Ala Ala Gly Gly Ala Thr Cys Ala Gly Gly Gly Gly
                 900              905              910

Gly Thr Gly Gly Gly Cys Ala Ala Cys Thr Gly Gly Thr Ala Ala Cys
                 915              920              925

Thr Gly Ala Ala Gly Thr Cys Ala Cys Cys Ala Ala Gly Ala Ala Ala
    930              935              940

Gly Ala Ala Gly Ala Thr Thr Cys Cys Thr Gly Cys Cys Ala Gly Cys
945              950              955              960

Thr Gly Gly Gly Cys Thr Ala Cys Thr Cys Gly Gly Cys Cys Gly Gly
                 965              970              975

Thr Cys Cys Cys Thr Gly Cys Ala Thr Gly Gly Gly Ala Ala Thr Gly
                 980              985              990

Ala Cys Cys Ala Gly Cys Ala Gly  Gly Thr Ala Thr Thr  Thr Cys Thr
                 995              1000             1005

Ala Thr  Ala Ala Thr Gly Gly  Thr Ala Cys Ala Thr  Cys Cys Ala
    1010             1015             1020

Thr Gly  Gly Cys Cys Thr Gly  Thr Gly Ala Gly Ala  Cys Thr Thr
    1025             1030             1035

Thr Cys  Cys Ala Gly Thr Ala  Cys Gly Gly Cys Gly  Gly Cys Thr
    1040             1045             1050

Gly Cys  Ala Thr Gly Gly Gly  Cys Ala Ala Cys Gly  Gly Thr Ala
    1055             1060             1065

Ala Cys  Ala Ala Cys Thr Thr  Cys Gly Thr Cys Ala  Cys Ala Gly
    1070             1075             1080

Ala Ala  Ala Ala Gly Gly Ala  Gly Thr Gly Thr Cys  Thr Gly Cys
    1085             1090             1095

Ala Gly  Ala Cys Cys Thr Gly  Cys Cys Gly Ala Ala  Cys Thr Gly
    1100             1105             1110

Thr Gly  Gly Cys Gly Gly Cys  Cys Thr Gly Cys Ala  Ala Thr Cys
    1115             1120             1125

Thr Cys  Cys Cys Ala Thr  Ala Gly Thr Cys Cys  Gly Gly Gly
    1130             1135             1140

Gly Cys  Cys Cys Cys Thr Gly  Cys Cys Gly Ala Gly  Cys Cys Thr
    1145             1150             1155

Thr Cys  Ala Thr Cys Cys Ala  Gly Cys Thr Cys Thr  Gly Gly Gly
    1160             1165             1170

Cys Ala  Thr Thr Thr Gly Ala  Thr Gly Cys Thr Gly  Thr Cys Ala
    1175             1180             1185

Ala Gly  Gly Gly Gly Ala Ala  Gly Thr Gly Cys Gly  Thr Cys Cys
    1190             1195             1200

Thr Cys  Thr Thr Cys Cys Cys  Cys Thr Ala Cys Gly  Gly Gly Gly
    1205             1210             1215

Gly Cys  Thr Gly Cys Cys Ala  Gly Gly Gly Cys Ala  Ala Cys Gly
    1220             1225             1230

Gly Gly  Ala Ala Cys Ala Ala  Gly Thr Thr Cys Thr  Ala Cys Thr
    1235             1240             1245
```

```
Cys Ala  Gly Ala Gly Ala Ala  Gly Gly Ala Gly Thr  Gly Cys Ala
    1250             1255              1260

Gly Ala  Gly Ala Gly Thr Ala  Cys Thr Gly Cys Gly  Gly Thr Gly
    1265             1270              1275

Thr Cys  Cys Cys Thr Gly Gly  Thr Gly Ala Thr Gly  Gly Thr Gly
    1280             1285              1290

Ala Thr  Gly Ala Gly Gly Ala  Gly Cys Thr Gly Cys  Thr Gly Cys
    1295             1300              1305

Gly Cys  Thr Thr Cys Thr Cys  Cys Ala Ala Cys Thr  Gly Ala Cys
    1310             1315              1320

Ala Ala  Cys Thr Gly Gly Cys  Cys Gly Gly Thr Cys  Thr Gly Cys
    1325             1330              1335

Ala Ala  Gly Thr Cys Ala Gly  Ala Gly Gly Ala Thr  Gly Gly Cys
    1340             1345              1350

Cys Ala  Gly Thr Gly Thr Cys  Thr Gly Thr Cys Cys  Cys Gly Gly
    1355             1360              1365

Gly Gly  Thr Cys Cys Thr Gly  Thr Gly Gly Cys Ala  Gly Gly Cys
    1370             1375              1380

Ala Gly  Cys Gly Cys Cys Ala  Ala Gly Cys Ala Ala  Cys Cys Thr
    1385             1390              1395

Gly Gly  Gly Thr Cys Cys Ala  Ala Ala Thr Ala Ala  Ala Ala Ala
    1400             1405              1410

Cys Thr  Ala Ala Ala Thr Thr  Gly Thr Ala Ala Ala  Cys Thr Cys
    1415             1420              1425

Cys Thr  Gly Ala Ala Ala Ala  Ala Ala Ala Ala Ala  Ala Ala Ala
    1430             1435              1440

Ala Ala  Ala Ala Ala Ala Ala
    1445             1450

<210> SEQ ID NO 2
<211> LENGTH: 352
<212> TYPE: PRT
<213> ORGANISM: Homo sapiens

<400> SEQUENCE: 2

Met Arg Ser Leu Gly Ala Leu Leu Leu Leu Ser Ala Cys Leu Ala
1               5                   10                  15

Val Ser Ala Gly Pro Val Pro Thr Pro Pro Asp Asn Ile Gln Val Gln
                20                  25                  30

Glu Asn Phe Asn Ile Ser Arg Ile Tyr Gly Lys Trp Tyr Asn Leu Ala
            35                  40                  45

Ile Gly Ser Thr Cys Pro Trp Leu Lys Lys Ile Met Asp Arg Met Thr
        50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
            115                 120                 125

Glu Tyr Ala Ile Phe Leu Thr Lys Lys Phe Ser Arg His His Gly Pro
        130                 135                 140

Thr Ile Thr Ala Lys Leu Tyr Gly Arg Ala Pro Gln Leu Arg Glu Thr
```

-continued

```
145             150             155             160

Leu Leu Gln Asp Phe Arg Val Val Ala Gln Gly Val Gly Ile Pro Glu
            165             170             175

Asp Ser Ile Phe Thr Met Ala Asp Arg Gly Glu Cys Val Pro Gly Glu
            180             185             190

Gln Glu Pro Glu Pro Ile Leu Ile Pro Arg Val Arg Ala Val Leu
            195             200             205

Pro Gln Glu Glu Glu Gly Ser Gly Gly Gly Gln Leu Val Thr Glu Val
        210             215             220

Thr Lys Lys Glu Asp Ser Cys Gln Leu Gly Tyr Ser Ala Gly Pro Cys
225             230             235             240

Met Gly Met Thr Ser Arg Tyr Phe Tyr Asn Gly Thr Ser Met Ala Cys
            245             250             255

Glu Thr Phe Gln Tyr Gly Gly Cys Met Gly Asn Gly Asn Asn Phe Val
            260             265             270

Thr Glu Lys Glu Cys Leu Gln Thr Cys Arg Thr Val Ala Ala Cys Asn
            275             280             285

Leu Pro Ile Val Arg Gly Pro Cys Arg Ala Phe Ile Gln Leu Trp Ala
        290             295             300

Phe Asp Ala Val Lys Gly Lys Cys Val Leu Phe Pro Tyr Gly Gly Cys
305             310             315             320

Gln Gly Asn Gly Asn Lys Phe Tyr Ser Glu Lys Glu Cys Arg Glu Tyr
            325             330             335

Cys Gly Val Pro Gly Asp Gly Asp Glu Glu Leu Leu Arg Phe Ser Asn
            340             345             350
```

```
<210> SEQ ID NO 3
<211> LENGTH: 2427
<212> TYPE: DNA
<213> ORGANISM: Homo sapiens

<400> SEQUENCE: 3
aacaacaacc tcacagcttg gacaaggcaa acattatgcc aggaggaaaa aatattccac      60
ccccaagaaa acaatatcaa aaaacagaac tagagactaa ttggaggaga gattgccagc     120
ctggggcaaa tgtgtatata taagtatgag gcacatcatg accagactaa ctctaccttt     180
ctggcttcag gtgctatcta gacctgaagt agcgggaaga gcagaaagga tggggcagcc     240
atctctgact tggatgctga tggtggtggt ggcctcttgg ttcatcacaa ctgcagccac     300
tgacacctca gaagcaagat ggtgctctga atgtcacagc aatgccacct gcacggagga     360
tgaggccgtt acgacgtgca cctgtcagga gggcttcacc ggcgatggcc tgacctgcgt     420
ggacctggat gagtgcgcca ttcctggagc tcacaactgc tccgccaaca gcagctgcgt     480
aaacacgcca ggctccttct cctgcgtctg ccccgaaggc ttccgcctgt cgcccggtct     540
cggctgcaca gacgtggatg agtgcgctga gcctgggctt agccactgcc acgccctggc     600
cacatgtgtc aatgtggtgg gcagctactt gtgcgtatgc cccgcgggct accggggga     660 tggatggcac tgtgagtgct ccccgggctc ctgcgggccg gggttggact gcgtgcccga     720
gggcgacgcg ctcgtgtgcg cggatccgtg ccaggcgcac cgcaccctgg acgagtactg     780
gcgcagcacc gagtacgggg agggctacgc ctgcgacacg gacctgcgcg gctggtaccg     840
cttcgtgggc cagggcggtg cgcgcatggc cgagacctgc gtgccagtcc tgcgctgcaa     900
cacggccgcc cccatgtggc tcaatggcac gcatccgtcc agcgacgagg gcatcgtgag     960
ccgcaaggcc tgcgcgcact ggagcggcca ctgctgcctg tgggatgcgt ccgtccaggt    1020
```

-continued

```
gaaggcctgt gccggcggct actacgtcta caacctgaca gcgcccccg agtgtcacct    1080 ggcgtactgc acagacccca gctccgtgga ggggacgtgt gaggagtgca gtatagacga    1140
ggactgcaaa tcgaataatg gcagatggca ctgccagtgc aaacaggact tcaacatcac    1200
tgatatctcc ctcctggagc acaggctgga atgtgggggcc aatgacatga aggtgtcgct    1260
gggcaagtgc cagctgaaga gtctgggctt cgacaaggtc ttcatgtacc tgagtgacag    1320
ccggtgctcg ggcttcaatg acagagacaa ccgggactgg gtgtctgtag tgaccccagc    1380
ccgggatggc ccctgtggga cagtgttgac gaggaatgaa acccatgcca cttacagcaa    1440
caccctctac ctggcagatg agatcatcat ccgtgacctc aacatcaaaa tcaactttgc    1500
atgctcctac cccctggaca tgaaagtcag cctgaagacc gccctacagc caatggtcag    1560
tgctctaaac atcagagtgg gcgggaccgg catgttcacc gtgcggatgg cgctcttcca    1620 gacccccttcc tacacgcagc cctaccaagg ctcctccgtg acactgtcca ctgaggcttt    1680
tctctacgtg ggcaccatgt tggatggggg cgacctgtcc cgatttgcac tgctcatgac    1740
caactgctat gccacaccca gtagcaatgc cacggacccc ctgaagtact tcatcatcca    1800
ggacagatgc ccacacacta gagactcaac tatccaagtg gtggagaatg gggagtcctc    1860
ccagggccga ttttccgtcc agatgttccg gtttgctgga aactatgacc tagtctacct    1920
gcactgtgaa gtctatctct gtgacaccat gaatgaaaag tgcaagccta cctgctctgg    1980
gaccagattc cgaagtggga gtgtcataga tcaatcccgt gtcctgaact gggtcccat    2040 cacacggaaa ggtgtccagg ccacagtctc aagggctttt agcagcttgg ggctcctgaa    2100
agtctggctg cctctgcttc tctcggccac cttgaccctg acttttcagt gactgacagc    2160
ggaaagccct gtgctccatg gctgccatct cacctcctgc tgggcagggg gcatgatgcg    2220
ggccagtgct ccagccacag aaaagaaagt tcatgctttg ttcagcctgc cttcttttct    2280
cccttttaat cctggctgtc gagaaacagc ctgtgtcttt aaatgctgct ttttctcaaa    2340
atgggacttg tgacggtgta cctgaggccc ccatctcctt aaagagtgtg gcaaaataat    2400
gatttttaaa tctcaaaaaa aaaaaaa                                        2427
```

<210> SEQ ID NO 4
<211> LENGTH: 640
<212> TYPE: PRT
<213> ORGANISM: Homo sapiens

<400> SEQUENCE: 4

```
Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg Trp Cys
            20                  25                  30

Ser Glu Cys His Ser Asn Ala Thr Cys Thr Glu Asp Glu Ala Val Thr
        35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
            100                 105                 110

Ala Glu Pro Gly Leu Ser His Cys His Ala Leu Ala Thr Cys Val Asn
```

-continued

```
           115                 120                 125

Val Val Gly Ser Tyr Leu Cys Val Cys Pro Ala Gly Tyr Arg Gly Asp
    130                 135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
                165                 170                 175

His Arg Thr Leu Asp Glu Tyr Trp Arg Ser Thr Glu Tyr Gly Glu Gly
            180                 185                 190

Tyr Ala Cys Asp Thr Asp Leu Arg Gly Trp Tyr Arg Phe Val Gly Gln
        195                 200                 205

Gly Gly Ala Arg Met Ala Glu Thr Cys Val Pro Val Leu Arg Cys Asn
    210                 215                 220

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
                245                 250                 255

Leu Trp Asp Ala Ser Val Gln Val Lys Ala Cys Ala Gly Gly Tyr Tyr
            260                 265                 270

Val Tyr Asn Leu Thr Ala Pro Pro Glu Cys His Leu Ala Tyr Cys Thr
        275                 280                 285

Asp Pro Ser Ser Val Glu Gly Thr Cys Glu Glu Cys Ser Ile Asp Glu
    290                 295                 300

Asp Cys Lys Ser Asn Asn Gly Arg Trp His Cys Gln Cys Lys Gln Asp
305                 310                 315                 320

Phe Asn Ile Thr Asp Ile Ser Leu Leu Glu His Arg Leu Glu Cys Gly
                325                 330                 335

Ala Asn Asp Met Lys Val Ser Leu Gly Lys Cys Gln Leu Lys Ser Leu
            340                 345                 350

Gly Phe Asp Lys Val Phe Met Tyr Leu Ser Asp Ser Arg Cys Ser Gly
        355                 360                 365

Phe Asn Asp Arg Asp Asn Arg Asp Trp Val Ser Val Val Thr Pro Ala
    370                 375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Ile Arg Asp
                405                 410                 415

Leu Asn Ile Lys Ile Asn Phe Ala Cys Ser Tyr Pro Leu Asp Met Lys
            420                 425                 430

Val Ser Leu Lys Thr Ala Leu Gln Pro Met Val Ser Ala Leu Asn Ile
        435                 440                 445

Arg Val Gly Gly Thr Gly Met Phe Thr Val Arg Met Ala Leu Phe Gln
    450                 455                 460

Thr Pro Ser Tyr Thr Gln Pro Tyr Gln Gly Ser Ser Val Thr Leu Ser
465                 470                 475                 480

Thr Glu Ala Phe Leu Tyr Val Gly Thr Met Leu Asp Gly Gly Asp Leu
                485                 490                 495

Ser Arg Phe Ala Leu Leu Met Thr Asn Cys Tyr Ala Thr Pro Ser Ser
            500                 505                 510

Asn Ala Thr Asp Pro Leu Lys Tyr Phe Ile Ile Gln Asp Arg Cys Pro
        515                 520                 525

His Thr Arg Asp Ser Thr Ile Gln Val Val Glu Asn Gly Glu Ser Ser
    530                 535                 540
```

```
Gln Gly Arg Phe Ser Val Gln Met Phe Arg Phe Ala Gly Asn Tyr Asp
545                 550                 555                 560

Leu Val Tyr Leu His Cys Glu Val Tyr Leu Cys Asp Thr Met Asn Glu
                565                 570                 575

Lys Cys Lys Pro Thr Cys Ser Gly Thr Arg Phe Arg Ser Gly Ser Val
            580                 585                 590

Ile Asp Gln Ser Arg Val Leu Asn Leu Gly Pro Ile Thr Arg Lys Gly
        595                 600                 605

Val Gln Ala Thr Val Ser Arg Ala Phe Ser Ser Leu Gly Leu Leu Lys
    610                 615                 620

Val Trp Leu Pro Leu Leu Leu Ser Ala Thr Leu Thr Leu Thr Phe Gln
625                 630                 635                 640

<210> SEQ ID NO 5
<211> LENGTH: 1867
<212> TYPE: DNA
<213> ORGANISM: Homo sapiens

<400> SEQUENCE: 5
cacatagctc agttcccata aaagggctgg tttgccgcgt cggggagtgg agtgggacag      60
gtatataaag gaagtacagg gcctggggaa gaggccctgt ctaggtagct ggcaccagga     120
gccgtgggca agggaagagg ccacaccctg ccctgctctg ctgcagccag aatgggtgtg     180
aaggcgtctc aaacaggctt tgtggtcctg gtgctgctcc agtgctgctc tgcatacaaa     240
ctggtctgct actacaccag ctggtcccag taccgggaag gcgatgggag ctgcttccca     300
gatgcccttg accgcttcct ctgtacccac atcatctaca gctttgccaa tataagcaac     360
gatcacatcg acacctggga gtggaatgat gtgacgctct acggcatgct caacacactc     420
aagaacagga accccaacct gaagactctc ttgtctgtcg gaggatggaa ctttgggtct     480
caaagatttt ccaagatagc ctccaacacc cagagtcgcc ggactttcat caagtcagta     540
ccgccatttc tgcgcaccca tggctttgat gggctggacc ttgcctggct ctaccctgga     600
cggagagaca aacagcattt taccacccta atcaaggaaa tgaaggccga atttataaag     660
gaagcccagc cagggaaaaa gcagctcctg ctcagcgcag cactgtctgc ggggaaggtc     720
accattgaca gcagctatga cattgccaag atatcccaac acctggattt cattagcatc     780
atgacctacg attttcatgg agcctggcgt gggaccacag gccatcacag tcccctgttc     840
cgaggtcagg aggatgcaag tcctgacaga ttcagcaaca ctgactatgc tgtggggtac     900
atgttgaggc tggggctcc tgccagtaag ctggtgatgg gcatcccac cttcgggagg      960 agcttcactc tggcttcttc tgagactggt gttggagccc caatctcagg accgggaatt    1020
ccaggccggt tcaccaagga ggcagggacc cttgcctact atgagatctg tgacttcctc    1080
cgcggagcca cagtccatag aatcctcggc cagcaggtcc cctatgccac caagggcaac    1140
cagtgggtag gatacgacga ccaggaaagc gtcaaaagca aggtgcagta cctgaaggac    1200
aggcagctgg cgggcgccat ggtatgggcc ctggacctgg atgacttcca gggctccttc    1260
tgcggccagg atctgcgctt ccctctcacc aatgccatca aggatgcact cgctgcaacg    1320
tagccctctg ttctgcacac agcacggggg ccaaggatgc cccgtccccc tctggctcca    1380
gctggccggg agcctgatca cctgccctgc tgagtcccag gctgagcctc agtctccctc    1440
ccttggggcc tatgcagagg tccacaacac acagatttga gctcagccct ggtgggcaga    1500
gaggtaggga tggggctgtg gggatagtga ggcatcgcaa tgtaagactc gggattagta    1560
```

-continued

```
cacacttgtt gattaatgga aatgtttaca gatccccaag cctggcaagg gaatttcttc      1620
aactccctgc cccccagccc tccttatcaa aggacaccat tttggcaagc tctatcacca      1680
aggagccaaa catcctacaa gacacagtga ccatactaat tataccccct gcaaagccca      1740
gcttgaaacc ttcacttagg aacgtaatcg tgtcccctat cctacttccc cttcctaatt      1800
ccacagctgc tcaataaagt acaagagctt aacagtgaaa aaaaaaaaa aaaaaaaaa      1860 aaaaaaa                                                               1867
```

```
<210> SEQ ID NO 6
<211> LENGTH: 383
<212> TYPE: PRT
<213> ORGANISM: Homo sapiens

<400> SEQUENCE: 6

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
        290                 295                 300

Gly Ala Thr Val His Arg Ile Leu Gly Gln Gln Val Pro Tyr Ala Thr
305                 310                 315                 320
```

```
Lys Gly Asn Gln Trp Val Gly Tyr Asp Asp Gln Glu Ser Val Lys Ser
            325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380
```

```
<210> SEQ ID NO 7
<211> LENGTH: 863
<212> TYPE: DNA
<213> ORGANISM: Homo sapiens

<400> SEQUENCE: 7
agggccaccc aggtgagcct ctcactcgcc acctcctctt ccacccctgc caggcccagc      60
agccaccaca gcgcctgctt cctcggccct gaaatcatgc ccctaggtct cctgtggctg     120
ggcctagccc tgttgggggc tctgcatgcc caggcccagg actccacctc agacctgatc     180
ccagccccac ctctgagcaa ggtccctctg cagcagaact ccaggacaa ccaattccag      240 gggaagtggt atgtggtagg cctggcaggg aatgcaattc tcagagaaga caaagacccg     300
caaaagatgt atgccaccat ctatgagctg aaagaagaca gagctacaa tgtcacctcc      360 gtcctgtttta ggaaaaagaa gtgtgactac tggatcagga cttttgttcc aggttgccag     420
cccggcgagt tcacgctggg caacattaag agttaccctg gattaacgag ttacctcgtc     480
cgagtggtga gcaccaacta caaccagcat gctatggtgt tcttcaagaa agtttctcaa     540
aacagggagt acttcaagat caccctctac gggagaacca aggagctgac ttcggaacta     600
aaggagaact tcatccgctt ctccaaatct ctgggcctcc ctgaaaacca tcgtcttc       660 cctgtcccaa tcgaccagtg tatcgacggc tgagtgcaca ggtgccgcca gctgccgcac     720
cagcccgaac accattgagg gagctgggag accctcccca cagtgccacc catgcagctg     780
ctccccaggc caccccgctg atggagcccc accttgtctg ctaaataaac atgtgccctc     840
aggccaaaaa aaaaaaaaaa aaa                                            863
```

```
<210> SEQ ID NO 8
<211> LENGTH: 198
<212> TYPE: PRT
<213> ORGANISM: Homo sapiens

<400> SEQUENCE: 8

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110
```

```
Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195

<210> SEQ ID NO 9
<211> LENGTH: 1626
<212> TYPE: DNA
<213> ORGANISM: Homo sapiens

<400> SEQUENCE: 9
agtgctatta ctgcatatga tgtaggttta gttttccaag ttcttccgtg gccctttttg      60
cttattatat caatccttgg tgggagatag aggaagcatt tttagtgcta ttttacaact     120
gaggaaatag aggtttgaag agaactcagg aactctcagg gttacccagc attgtgagtg     180
acagagcctg gatctgaacg ctgatcccat aatgcatcct caagtggtca tcttaagcct     240
catcctacat ctggcagatt ctgtagctgg ttctgtaaag gttggtggag aggcaggtcc     300
atctgtcaca ctaccctgcc actacagtgg agctgtcaca tccatgtgct ggaatagagg     360
ctcatgttct ctattcacat gccaaaatgg cattgtctgg accaatggaa cccacgtcac     420
ctatcggaag gacacacgct ataagctatt gggggacctt tcaagaaggg atgtctcttt     480
gaccatagaa aatacagctg tgtctgacag tggcgtatat tgttgccgtg ttgagcaccg     540
tgggtggttc aatgacatga aaatcaccgt atcattggag attgtgccac ccaaggtcac     600
gactactcca attgtcacaa ctgttccaac cgtcacgact gttcgaacga gcaccactgt     660
tccaacgaca acgactgttc caatgacgac tgttccaacg acaactgttc caacaacaat     720
gagcattcca acgacaacga ctgttctgac gacaatgact gtttcaacga caacgagcgt     780
tccaacgaca acgagcattc caacaacaac aagtgttcca gtgacaacaa ctgtctctac     840
ctttgttcct ccaatgcctt gcccaggca gaaccatgaa ccagtagcca cttcaccatc     900
ttcacctcag ccagcagaaa cccaccctac gacactgcag ggagcaataa ggagagaacc     960
caccagctca ccattgtact cttacacaac agatgggaat gacaccgtga cagagtcttc    1020
agatggcctt tggaataaca atcaaactca actgttccta gaacatagtc tactgacggc    1080
caataccact aaaggaatct atgctggagt ctgtatttct gtcttggtgc ttcttgctct    1140
tttgggtgtc atcattgcca aaaagtattt cttcaaaaag gaggttcaac aactaagtgt    1200
ttcatttagc agccttcaaa ttaaagcttt gcaaaatgca gttgaaaagg aagtccaagc    1260
agaagacaat atctacattg agaatagtct ttatgccacg gactaagacc cagtggtgct    1320
ctttgagagt ttacgcccat gagtgcagaa gactgaacag acatcagcac atcagacgtc    1380
ttttagaccc caagacaatt tttctgtttc agtttcatct ggcattccaa catgtcagtg    1440
atactgggta gagtaactct ctcactccaa actgtgtata gtcaacctca tcattaatgt    1500
agtcctaatt ttttatgcta aaactggctc aatccttctg atcattgcag ttttctctca    1560
```
aatatgaaca ctttataatt gtatgttctt tttagacccc ataaatcctg tatacatcaa    1620
agagaa                                                               1626

<210> SEQ ID NO 10
<211> LENGTH: 364
<212> TYPE: PRT
<213> ORGANISM: Homo sapiens

<400> SEQUENCE: 10

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
            195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
            260                 265                 270

Leu Trp Asn Asn Asn Gln Thr Gln Leu Phe Leu Glu His Ser Leu Leu
            275                 280                 285

Thr Ala Asn Thr Thr Lys Gly Ile Tyr Ala Gly Val Cys Ile Ser Val
    290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
            340                 345                 350

Asn Ile Tyr Ile Glu Asn Ser Leu Tyr Ala Thr Asp

```
            355                   360
```

```
<210> SEQ ID NO 11
<211> LENGTH: 1151
<212> TYPE: DNA
<213> ORGANISM: Homo sapiens

<400> SEQUENCE: 11
attctctccc cagcttgctg agccctttgc tcccctggcg actgcctgga cagtcagcaa      60
ggaattgtct cccagtgcat tttgccctcc tggctgccaa ctctggctgc taaagcggct     120
gccacctgct gcagtctaca cagcttcggg aagaggaaag gaacctcaga ccttccagat     180
cgcttcctct cgcaacaaac tatttgtcgc aggaataaag atggctgctg aaccagtaga     240
agacaattgc atcaactttg tggcaatgaa atttattgac aatacgcttt actttataga     300
aaacctggaa tcagattact ttggcaagct tgaatctaaa ttatcagtca taagaaattt     360
gaatgaccaa gttctcttca ttgaccaagg aaatcggcct ctatttgaag atatgactga     420
ttctgactgt agagataatg cacccgggac catatttatt ataagtatgt ataaagatag     480
ccagcctaga ggtatggctg taactatctc tgtgaagtgt gagaaaattt caactctctc     540
ctgtgagaac aaaattattt cctttaagga aatgaatcct cctgataaca tcaaggatac     600
aaaaagtgac atcatattct ttcagagaag tgtcccagga catgataata agatgcaatt     660
tgaatcttca tcatacgaag gatactttct agcttgtgaa aaagagagag accttttttaa     720 actcattttg aaaaaagagg atgaattggg ggatagatct ataatgttca ctgttcaaaa     780
cgaagactag ctattaaaat ttcatgccgg gcgcagtggc tcacgcctgt aatcccagcc     840
ctttgggagg ctgaggcggg cagatcacca gaggtcaggt gttcaagacc agcctgacca     900
acatggtgaa acctcatctc tactaaaaat acaaaaaatt agctgagtgt agtgacgcat     960
gccctcaatc ccagctactc aagaggctga ggcaggagaa tcacttgcac tccggaggta    1020
gaggttgtgg tgagccgaga ttgcaccatt gcgctctagc ctgggcaaca acagcaaaac    1080
tccatctcaa aaaataaaat aaataaataa acaaataaaa aattcataat gtgaaaaaaa    1140
aaaaaaaaaa a                                                          1151

<210> SEQ ID NO 12
<211> LENGTH: 189
<212> TYPE: PRT
<213> ORGANISM: Homo sapiens

<400> SEQUENCE: 12

Met Ala Ala Glu Pro Val Glu Asp Asn Cys Ile Asn Phe Val Ala Met
1               5                   10                  15

Lys Phe Ile Asp Asn Thr Leu Tyr Phe Ile Glu Asn Leu Glu Ser Asp
            20                  25                  30

Tyr Phe Gly Lys Leu Glu Ser Lys Leu Ser Val Ile Arg Asn Leu Asn
        35                  40                  45

Asp Gln Val Leu Phe Ile Asp Gln Gly Asn Arg Pro Leu Phe Glu Asp
    50                  55                  60

Met Thr Asp Ser Asp Cys Arg Asp Asn Ala Pro Arg Thr Ile Phe Ile
65                  70                  75                  80

Ile Ser Met Tyr Lys Asp Ser Gln Pro Arg Gly Met Ala Val Thr Ile
                85                  90                  95

Ser Val Lys Cys Glu Lys Ile Ser Thr Leu Ser Cys Glu Asn Lys Ile
            100                 105                 110
```

```
Ile Ser Phe Lys Glu Met Asn Pro Pro Asp Asn Ile Lys Asp Thr Lys
        115                 120                 125

Ser Asp Ile Ile Phe Phe Gln Arg Ser Val Pro Gly His Asp Asn Lys
    130                 135                 140

Met Gln Phe Glu Ser Ser Ser Tyr Glu Gly Tyr Phe Leu Ala Cys Glu
145                 150                 155                 160

Lys Glu Arg Asp Leu Phe Lys Leu Ile Leu Lys Lys Glu Asp Glu Leu
                165                 170                 175

Gly Asp Arg Ser Ile Met Phe Thr Val Gln Asn Glu Asp
            180                 185
```

```
<210> SEQ ID NO 13
<211> LENGTH: 1675
<212> TYPE: DNA
<213> ORGANISM: Homo sapiens

<400> SEQUENCE: 13
attcctgaag ctgacagcat tcgggccgag atgtctcgct ccgtggcctt agctgtgctc      60
gcgctactct ctctttctgg cctggaggct atccagcgta ctccaaagat tcaggtttac     120
tcacgtcatc cagcagagaa tggaaagtca aatttcctga attgctatgt gtctgggttt     180
catccatccg acattgaagt tgacttactg aagaatggag agagaattga aaaagtggag     240
cattcagact tgtctttcag caaggactgg tctttctatc tcttgtacta cactgaattc     300 accccccactg aaaaagatga gtatgcctgc cgtgtgaacc atgtgacttt gtcacagccc     360
aagatagtta agtgggatcg agacatgtaa gcagcatcat ggaggtttga agatgccgca     420
tttggattgg atgaattcca aattctgctt gcttgctttt taatattgat atgcttatac     480
acttacactt tatgcacaaa atgtagggtt ataataatgt taacatggac atgatcttct     540
ttataattct actttgagtg ctgtctccat gtttgatgta tctgagcagg ttgctccaca     600
ggtagctcta ggagggctgg caacttagag gtggggagca gagaattctc ttatccaaca     660
tcaacatctt ggtcagattt gaactcttca atctcttgca ctcaaagctt gttaagatag     720
ttaagcgtgc ataagttaac ttccaattta catactctgc ttagaatttg ggggaaaatt     780
tagaaatata attgacagga ttattggaaa tttgttataa tgaatgaaac attttgtcat     840
ataagattca tatttacttc ttatacattt gataaagtaa ggcatggttg tggttaatct     900
ggtttatttt tgttccacaa gttaaataaa tcataaaact tgatgtgtta tctcttatat     960
ctcactccca ctattacccc tttatttttca aacagggaaa cagtcttcaa gttccacttg    1020
gtaaaaaatg tgaacccctt gtatatagag tttggctcac agtgtaaagg gcctcagtga    1080
ttcacatttt ccagattagg aatctgatgc tcaaagaagt taaatggcat agttggggtg    1140
acacagctgt ctagtgggag gccagccttc tatattttag ccagcgttct ttcctgcggg    1200
ccaggtcatg aggagtatgc agactctaag agggagcaaa agtatctgaa ggatttaata    1260
ttttagcaag gaatagatat acaatcatcc cttggtctcc ctgggggatt ggtttcagga    1320
ccccttcttg gacaccaaat ctatggatat ttaagtccct tctataaaat ggtatagtat    1380
ttgcatataa cctatccaca tcctcctgta tactttaaat catttctaga ttacttgtaa    1440
tacctaatac aatgtaaatg ctatgcaaat agttgttatt gtttaaggaa taatgacaag    1500
aaaaaaaagt ctgtacatgc tcagtaaaga cacaaccatc cctttttttc cccagtgttt    1560
ttgatccatg gtttgctgaa tccacagatg tggagcccct ggatacggaa ggcccgctgt    1620
actttgaatg acaaataaca gatttaaaat tttcaaggca tagttttata cctga         1675
```

```
<210> SEQ ID NO 14
<211> LENGTH: 119
<212> TYPE: PRT
<213> ORGANISM: Homo sapiens

<400> SEQUENCE: 14

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 15
<211> LENGTH: 760
<212> TYPE: DNA
<213> ORGANISM: Homo sapiens

<400> SEQUENCE: 15
gaggaaccga gaggctgaga ctaacccaga aacatccaat tctcaaactg aagctcgcac        60
tctcgcctcc agcatgaaag tctctgccgc ccttctgtgc ctgctgctca tagcagccac       120
cttcattccc caagggctcg ctcagccaga tgcaatcaat gccccagtca cctgctgtta       180
taacttcacc aataggaaga tctcagtgca gaggctcgcg agctatagaa gaatcaccag       240
cagcaagtgt cccaaagaag ctgtgatctt caagaccatt gtggccaagg agatctgtgc       300
tgaccccaag cagaagtggg ttcaggattc catggaccac ctggacaagc aaacccaaac       360
tccgaagact tgaacactca ctccacaacc caagaatctg cagctaactt attttcccct       420
agctttcccc agacaccctg tttttatttt attataatga ttttgtttgt tgatgtgaaa       480
cattatgcct taagtaatgt taattcttat ttaagttatt gatgttttaa gtttatcttt       540
catggtacta gtgttttttta gatacagaga cttggggaaa ttgcttttcc tcttgaacca       600
cagttctacc cctgggatgt tttgagggtc tttgcaagaa tcattaatac aaagaatttt       660
ttttaacatt ccaatgcatt gctaaaatat tattgtggaa atgaatattt tgtaactatt       720
acaccaaata aatatatttt tgtacaaaaa aaaaaaaaaa                            760

<210> SEQ ID NO 16
<211> LENGTH: 99
<212> TYPE: PRT
<213> ORGANISM: Homo sapiens

<400> SEQUENCE: 16

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30
```

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 17
<211> LENGTH: 929
<212> TYPE: DNA
<213> ORGANISM: Homo sapiens

<400> SEQUENCE: 17
gaggcgttcc ggaaaaggga gtgcaggccg cggtgggggtg gggcggcgaa ggccggaagg      60
gataaaaccg cagtcgccgg cctcgcgggg ctcacggcct cgcctcggta tcgcagcggg     120
tcctctctat ctagctccag cctctcgcct gcgccccact ccccgcgtcc cgcgtcctag     180
ccgaccatgg ccgggcccct gcgcgccccg ctgctcctgc tggccatcct ggccgtggcc     240
ctggccgtga gccccgcggc cggctccagt cccggcaagc cgccgcgcct ggtgggaggc     300
cccatggacg ccagcgtgga ggaggagggt gtgcggcgtg cactggactt tgccgtcggc     360
gagtacaaca aagccagcaa cgacatgtac cacagccgcg cgctgcaggt ggtgcgcgcc     420
cgcaagcaga tcgtagctgg ggtgaactac ttcttggacg tggagctggg ccgaaccacg     480
tgtaccaaga cccagcccaa cttggacaac tgccccttcc atgaccagcc acatctgaaa     540
aggaaagcat tctgctcttt ccagatctac gctgtgcctt ggcagggcac aatgaccttg     600
tcgaaatcca cctgtcagga cgcctagggg tctgtaccgg gctggcctgt gcctatcacc     660
tcttatgcac acctcccacc ccctgtattc ccaccctgg actggtggcc cctgccttgg      720
ggaaggtctc cccatgtgcc tgcaccagga gacagacaga gaaggcagca ggcggccttt     780
gttgctcagc aaggggctct gccctccctc cttccttctt gcttctcata gccccggtgt     840
gcggtgcata cacccccacc tcctgcaata aaatagtagc atcggcaaaa aaaaaaaaaa     900
aaaaaaaaaa aaaaaaaaaa aaaaaaaaa                                        929

<210> SEQ ID NO 18
<211> LENGTH: 146
<212> TYPE: PRT
<213> ORGANISM: Homo sapiens

<400> SEQUENCE: 18

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
                20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg

-continued

```
                    85                  90                  95
Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
        130                 135                 140

Asp Ala
145
```

```
<210> SEQ ID NO 19
<211> LENGTH: 1054
<212> TYPE: DNA
<213> ORGANISM: Homo sapiens

<400> SEQUENCE: 19
gccaaaacag tggggggctga actgacctct cccctttggg agagaaaaac tgtctgggag      60
cttgacaaag gcatgcagga gagaacagga gcagccacag ccaggaggga gagccttccc     120
caagcaaaca atccagagca gctgtgcaaa caacggtgca taaatgaggc ctcctggacc     180
atgaagcgag tcctgagctg cgtcccggag cccacggtgg tcatggctgc cagagcgctc     240
tgcatgctgg ggctggtcct ggccttgctg tcctccagct ctgctgagga gtacgtgggc     300
ctgtctgcaa accagtgtgc cgtgccagcc aaggacaggt ggactgcgg ctaccccat      360 gtcacccca aggagtgcaa caaccggggc tgctgctttg actccaggat ccctggagtg     420
ccttggtgtt tcaagcccct gcaggaagca gaatgcacct tctgaggcac ctccagctgc     480
ccccggccgg gggatgcgag gctcggagca cccttgcccg gctgtgattg ctgccaggca     540
ctgttcatct cagcttttct gtcccttgc tcccggcaag cgcttctgct gaaagttcat      600
atctggagcc tgatgtctta acgaataaag gtcccatgct ccaccccgagg acagttcttc    660 gtgcctgaga ctttctgagg ttgtgcttta tttctgctgc gtcgtgggag agggcgggag     720
ggtgtcaggg gagagtctgc ccaggcctca agggcaggaa aagactccct aaggagctgc     780
agtgcatgca aggatatttt gaatccagac tggcacccac gtcacaggaa agcctaggaa     840
cactgtaagt gccgcttcct cgggaaagca gaaaaaatac atttcaggta gaagttttca     900
aaaatcacaa gtctttcttg gtgaagacag caagccaata aaactgtctt ccaaagtggt      960
cctttatttc acaaccactc tcgctactgt tcaatacttg tactattcct gggttttgtt    1020
tctttgtaca gtaaacatta tgaacaaaca ggca                                 1054
```

```
<210> SEQ ID NO 20
<211> LENGTH: 94
<212> TYPE: PRT
<213> ORGANISM: Homo sapiens

<400> SEQUENCE: 20

Met Lys Arg Val Leu Ser Cys Val Pro Glu Pro Thr Val Val Met Ala
1               5                   10                  15

Ala Arg Ala Leu Cys Met Leu Gly Leu Val Leu Ala Leu Leu Ser Ser
            20                  25                  30

Ser Ser Ala Glu Glu Tyr Val Gly Leu Ser Ala Asn Gln Cys Ala Val
        35                  40                  45

Pro Ala Lys Asp Arg Val Asp Cys Gly Tyr Pro His Val Thr Pro Lys
        50                  55                  60

Glu Cys Asn Asn Arg Gly Cys Cys Phe Asp Ser Arg Ile Pro Gly Val
```

-continued

```
65                  70                  75                  80

Pro Trp Cys Phe Lys Pro Leu Gln Glu Ala Glu Cys Thr Phe
                85                  90
```

```
<210> SEQ ID NO 21
<211> LENGTH: 2877
<212> TYPE: DNA
<213> ORGANISM: Homo sapiens

<400> SEQUENCE: 21
gctttccgcg gcattctttg ggcgtgagtc atgcaggttt gcagccagcc ccaaaggggg        60
tgtgtgcgcg agcagagcgc tataaatacg gcgcctccca gtgcccacaa cgcggcgtcg       120
ccaggaggag cgcgcgggca cagggtgccg ctgaccgagg cgtgcaaaga ctccagaatt       180
ggaggcatga tgaagactct gctgctgttt gtggggctgc tgctgacctg ggagagtggg       240
caggtcctgg gggaccagac ggtctcagac aatgagctcc aggaaatgtc caatcaggga       300
agtaagtacg tcaataagga aattcaaaat gctgtcaacg gggtgaaaca gataaagact       360
ctcatagaaa aaacaaacga agagcgcaag acactgctca gcaacctaga agaagccaag       420
aagaagaaag aggatgccct aaatgagacc agggaatcag agacaaagct gaaggagctc       480
ccaggagtgt gcaatgagac catgatggcc ctctgggaag agtgtaagcc ctgcctgaaa       540
cagacctgca tgaagttcta cgcacgcgtc tgcagaagtg gctcaggcct ggttggccgc       600
cagcttgagg agttcctgaa ccagagctcg cccttctact tctggatgaa tggtgaccgc       660
atcgactccc tgctggagaa cgaccggcag cagacgcaca tgctggatgt catgcaggac       720
cacttcagcc gcgcgtccag catcatagac gagctcttcc aggacaggtt cttcacccgg       780
gagccccagg atacctacca ctacctgccc ttcagcctgc cccaccggag gcctcacttc       840
ttctttccca agtcccgcat cgtccgcagc ttgatgccct tctctccgta cgagcccctg       900
aacttccacg ccatgttcca gcccttcctt gagatgatac acgaggctca gcaggccatg       960
gacatccact tccatagccc ggccttccag cacccgccaa cagaattcat acgagaaggc      1020
gacgatgacc ggactgtgtg ccgggagatc cgccacaact ccacgggctg cctgcggatg      1080
aaggaccagt gtgacaagtg ccgggagatc ttgtctgtgg actgttccac caacaacccc      1140
tcccaggcta agctgcggcg ggagctcgac gaatccctcc aggtcgctga gaggttgacc      1200
aggaaataca cgagctgct aaagtcctac cagtggaaga tgctcaacac ctcctccttg      1260
ctggagcagc tgaacgagca gtttaactgg gtgtcccggc tggcaaacct cacgcaaggc      1320
gaagaccagt actatctgcg ggtcaccacg gtggcttccc acacttctga ctcggacgtt      1380
ccttccggtg tcactgaggt ggtcgtgaag ctctttgact ctgatccat cactgtgacg      1440 gtccctgtag aagtctccag gaagaaccct aaatttatgg agaccgtggc ggagaaagcg      1500
ctgcaggaat accgcaaaaa gcaccgggag gagtgagatg tggatgttgc ttttgcacct      1560
acgggggcat ctgagtccag ctcccccaa gatgagctgc agcccccag agagagctct      1620 gcacgtcacc aagtaaccag gccccagcct ccaggccccc aactccgccc agcctctccc      1680
cgctctggat cctgcactct aacactcgac tctgctgctc atgggaagaa cagaattgct      1740
cctgcatgca actaattcaa taaaactgtc ttgtgagctg atcgcttgga gggtcctctt      1800
tttatgttga gttgctgctt cccggcatgc cttcattttg ctatgggggg caggcagggg      1860
ggatggaaaa taagtagaaa caaaaaagca gtggctaaga tggtataggg actgtcatac      1920
cagtgaagaa taaaagggtg aagaataaaa gggatatgat gacaaggttg atccacttca      1980
```

-continued

```
agaattgctt gctttcagga agagagatgt gtttcaacaa gccaactaaa atatattgct      2040
gcaaatggaa gctttttctgt tctattataa aactgtcgat gtattctgac caaggtgcga      2100
caatctccta aaggaataca ctgaaagtta aggagaagaa tcagtaagtg taaggtgtac      2160
ttggtattat aatgcataat tgatgttttc gttatgaaaa catttggtgc ccagaagtcc      2220
aaattatcag ttttatttgt aagagctatt gcttttgcag cggtttttatt tgtaaaagct      2280 gttgatttcg agttgtaaga gctcagcatc ccaggggcat cttcttgact gtggcatttc      2340
ctgtccaccg ccggtttata tgatcttcat acctttccct ggaccacagg cgtttctcgg      2400
cttttagtct gaaccatagc tgggctgcag taccctacgc tgccagcagg tggccatgac      2460
tacccgtggt accaatctca gtcttaaagc tcaggctttt cgttcattaa cattctctga      2520
tagaattctg gtcatcagat gtactgcaat ggaacaaaac tcatctggct gcatcccagg      2580
tgtgtagcaa agtccacatg taaatttata gcttagaata ttcttaagtc actgtccctt      2640
gtctctcttt gaagttataa acaacaaact taaagcttag cttatgtcca aggtaagtat      2700
tttagcatgg ctgtcaagga aattcagagt aaagtcagtg tgattcactt aatgatatac      2760
attaattaga attatggggt cagaggtatt tgcttaagtg atcataattg taaagtatat      2820
gtcacattgt cacattaatg tcacactgtt tcaaaagtta aaaaaaaaaa aaaaaaa       2877
```

```
<210> SEQ ID NO 22
<211> LENGTH: 449
<212> TYPE: PRT
<213> ORGANISM: Homo sapiens

<400> SEQUENCE: 22

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Phe Pro Lys Ser Arg
    210                 215                 220
```

```
Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
                260                 265                 270

Glu Phe Ile Arg Glu Gly Asp Asp Asp Arg Thr Val Cys Arg Glu Ile
            275                 280                 285

Arg His Asn Ser Thr Gly Cys Leu Arg Met Lys Asp Gln Cys Asp Lys
        290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
                340                 345                 350

Leu Asn Thr Ser Ser Leu Leu Glu Gln Leu Asn Glu Gln Phe Asn Trp
            355                 360                 365

Val Ser Arg Leu Ala Asn Leu Thr Gln Gly Glu Asp Gln Tyr Tyr Leu
        370                 375                 380

Arg Val Thr Thr Val Ala Ser His Thr Ser Asp Ser Asp Val Pro Ser
385                 390                 395                 400

Gly Val Thr Glu Val Val Val Lys Leu Phe Asp Ser Asp Pro Ile Thr
                405                 410                 415

Val Thr Val Pro Val Glu Val Ser Arg Lys Asn Pro Lys Phe Met Glu
                420                 425                 430

Thr Val Ala Glu Lys Ala Leu Gln Glu Tyr Arg Lys Lys His Arg Glu
        435                 440                 445

Glu
```

```
<210> SEQ ID NO 23
<211> LENGTH: 2335
<212> TYPE: DNA
<213> ORGANISM: Homo sapiens

<400> SEQUENCE: 23
aattattggt taaagaagta tattagtgct aatttccctc cgtttgtcct agctttttctc        60 ttctgtcaac cccacacgcc tttggcacaa tgaagtgggt aacctttatt tcccttctttt      120 ttctctttag ctcggcttat tccaggggtg tgtttcgtcg agatgcacac aagagtgagg      180
ttgctcatcg gtttaaagat ttgggagaag aaaatttcaa agccttggtg ttgattgcct      240
ttgctcagta tcttcagcag tgtccatttg aagatcatgt aaaattagtg aatgaagtaa      300
ctgaatttgc aaaaacatgt gttgctgatg agtcagctga aaattgtgac aaatcacttc      360 atacccttttt tggagacaaa ttatgcacag ttgcaactct tcgtgaaacc tatggtgaaa      420
tggctgactg ctgtgcaaaa caagaacctg agagaaatga atgcttcttg caacacaaag      480
atgacaaccc aaacctcccc cgattggtga accagaggt tgatgtgatg tgcactgctt      540
ttcatgacaa tgaagagaca tttttgaaaa aatacttata tgaaattgcc agaagacatc      600
cttactttta tgccccggaa ctcctttttct ttgctaaaag gtataaagct gctttttacag      660 aatgttgcca agctgctgat aaagctgcct gcctgttgcc aaagctcgat gaacttcggg      720
atgaagggaa ggcttcgtct gccaaacaga gactcaagtg tgccagtctc caaaaatttg      780
```

-continued

```
gagaaagagc tttcaaagca tgggcagtag ctcgcctgag ccagagattt cccaaagctg      840
agtttgcaga agtttccaag ttagtgacag atcttaccaa agtccacacg gaatgctgcc      900
atggagatct gcttgaatgt gctgatgaca gggcggacct tgccaagtat atctgtgaaa      960
atcaagattc gatctccagt aaactgaagg aatgctgtga aaaacctctg ttggaaaaat     1020
cccactgcat tgccgaagtg gaaaatgatg agatgcctgc tgacttgcct tcattagctg     1080
ctgattttgt tgaaagtaag gatgtttgca aaaactatgc tgaggcaaag gatgtcttcc     1140
tgggcatgtt tttgtatgaa tatgcaagaa ggcatcctga ttactctgtc gtgctgctgc     1200
tgagacttgc caagacatat gaaaccactc tagagaagtg ctgtgccgct gcagatcctc     1260
atgaatgcta tgccaaagtg ttcgatgaat ttaaacctct tgtggaagag cctcagaatt     1320
taatcaaaca aaattgtgag cttttttgagc agcttggaga gtacaaattc cagaatgcgc     1380
tattagttcg ttacaccaag aaagtacccc aagtgtcaac tccaactctt gtagaggtct     1440
caagaaacct aggaaaagtg ggcagcaaat gttgtaaaca tcctgaagca aaaagaatgc     1500
cctgtgcaga agactatcta tccgtggtcc tgaaccagtt atgtgtgttg catgagaaaa     1560
cgccagtaag tgcacagagtc accaaatgct gcacagaatc cttggtgaac aggcgaccat     1620
gcttttcagc tctggaagtc gatgaaacat acgttcccaa agagtttaat gctgaaacat     1680
tcaccttcca tgcagatata tgcacacttt ctgagaagga gagacaaatc aagaaacaaa     1740
ctgcacttgt tgagctcgtg aaacacaagc ccaaggcaac aaaagagcaa ctgaaagctg     1800
ttatggatga tttcgcagct tttgtagaga agtgctgcaa ggctgacgat aaggagacct     1860
gctttgccga ggagggtaaa aaacttgttg ctgcaagtca agctgcctta ggcttataac     1920
atcacattta aaagcatctc agcctaccat gagaataaga gaaagaaaat gaagatcaaa     1980
agcttattca tctgtttttc tttttcgttg gtgtaaagcc aacaccctgt ctaaaaaaca     2040
taaatttctt taatcatttt gcctcttttc tctgtgcttc aattaataaa aaatggaaag     2100
aatctaatag agtggtacag cactgttatt tttcaaagat gtgttgctat cctgaaaatt     2160
ctgtaggttc tgtggaagtt ccagtgttct ctcttattcc acttcggtag aggatttcta     2220
gtttcttgtg ggctaattaa ataaatcatt aatactcttc taagttatgg attataaaca     2280
ttcaaaataa tattttgaca ttatgataat tctgaataaa agaacaaaaa ccatg          2335
```

```
<210> SEQ ID NO 24
<211> LENGTH: 609
<212> TYPE: PRT
<213> ORGANISM: Homo sapiens

<400> SEQUENCE: 24

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
```

```
                    100                 105                 110

Asp Cys Cys Ala Lys Gln Glu Pro Glu Arg Asn Glu Cys Phe Leu Gln
                    115                 120                 125

His Lys Asp Asp Asn Pro Asn Leu Pro Arg Leu Val Arg Pro Glu Val
                    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                    165                 170                 175

Glu Leu Leu Phe Phe Ala Lys Arg Tyr Lys Ala Ala Phe Thr Glu Cys
                    180                 185                 190

Cys Gln Ala Ala Asp Lys Ala Ala Cys Leu Leu Pro Lys Leu Asp Glu
                    195                 200                 205

Leu Arg Asp Glu Gly Lys Ala Ser Ser Ala Lys Gln Arg Leu Lys Cys
                    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                    245                 250                 255

Lys Leu Val Thr Asp Leu Thr Lys Val His Thr Glu Cys Cys His Gly
                    260                 265                 270

Asp Leu Leu Glu Cys Ala Asp Asp Arg Ala Asp Leu Ala Lys Tyr Ile
                    275                 280                 285

Cys Glu Asn Gln Asp Ser Ile Ser Ser Lys Leu Lys Glu Cys Cys Glu
                    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                    325                 330                 335

Lys Asp Val Cys Lys Asn Tyr Ala Glu Ala Lys Asp Val Phe Leu Gly
                    340                 345                 350

Met Phe Leu Tyr Glu Tyr Ala Arg Arg His Pro Asp Tyr Ser Val Val
                    355                 360                 365

Leu Leu Leu Arg Leu Ala Lys Thr Tyr Glu Thr Thr Leu Glu Lys Cys
                    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                    405                 410                 415

Glu Leu Phe Glu Gln Leu Gly Glu Tyr Lys Phe Gln Asn Ala Leu Leu
                    420                 425                 430

Val Arg Tyr Thr Lys Lys Val Pro Gln Val Ser Thr Pro Thr Leu Val
                    435                 440                 445

Glu Val Ser Arg Asn Leu Gly Lys Val Gly Ser Lys Cys Cys Lys His
                    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                    485                 490                 495

Val Thr Lys Cys Cys Thr Glu Ser Leu Val Asn Arg Arg Pro Cys Phe
                    500                 505                 510

Ser Ala Leu Glu Val Asp Glu Thr Tyr Val Pro Lys Glu Phe Asn Ala
                    515                 520                 525
```

-continued

```
Glu Thr Phe Thr Phe His Ala Asp Ile Cys Thr Leu Ser Glu Lys Glu
    530                 535             540

Arg Gln Ile Lys Lys Gln Thr Ala Leu Val Glu Leu Val Lys His Lys
545                 550                 555             560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
        595                 600                 605

Leu

<210> SEQ ID NO 25
<211> LENGTH: 2258
<212> TYPE: DNA
<213> ORGANISM: Homo sapiens

<400> SEQUENCE: 25
ctcctccagc tcttcctgtc ccgctgttgc aacactgcct cactcttccc ctcccacctt      60
ctctcccctc ctctctgctt taattttctc agaattctct ggactgaggc tccagttctg     120
gcctttgggg ttcaagatca ctgggaccag gccgtgatct ctatgcccga gtctcaaccc     180
tcaactgtca ccccaaggca cttgggacgt cctggacaga ccgagtcccg ggaagcccca     240
gcactgccgc tgccacactg ccctgagccc aaatggggga gtgagaggcc atagctgtct     300
ggcatgggcc tctccaccgt gcctgacctg ctgctgccac tggtgctcct ggagctgttg     360
gtgggaatat acccctcagg ggttattgga ctggtccctc acctagggga cagggagaag     420
agagatagtg tgtgtcccca aggaaaatat atccaccctc aaaataattc gatttgctgt     480
accaagtgcc acaaaggaac ctacttgtac aatgactgtc caggcccggg gcaggatacg     540
gactgcaggt agtgtgagag cggctccttc accgcttcag aaaaccacct cagacactgc     600
ctcagctgct ccaaatgccg aaaggaaatg ggtcaggtgg agatctcttc ttgcacagtg     660
gaccgggaca ccgtgtgtgg ctgcaggaag aaccagtacc ggcattattg gagtgaaaac     720 ctttttccagt gcttcaattg cagcctctgc ctcaatggga ccgtgcacct ctcctgccag     780
gagaaacaga acaccgtgtg cacctgccat gcaggtttct ttctaagaga aaacgagtgt     840
gtctcctgta gtaactgtaa gaaaagcctg gagtgcacga agttgtgcct accccagatt     900
gagaatgtta agggcactga ggactcaggc accacagtgc tgttgcccct ggtcatttc     960 tttggtcttt gccttttatc cctcctcttc attggtttaa tgtatcgcta ccaacggtgg    1020
aagtccaagc tctactccat tgtttgtggg aaatcgacac ctgaaaaaga gggggagctt    1080
gaaggaacta ctactaagcc cctggcccca aacccaagct tcagtcccac tccaggcttc    1140 accccaccc tgggcttcag tcccgtgccc agttccacct tcacctccag ctccacctat    1200 accccggtg actgtcccaa ctttgcggct ccccgcagag aggtggcacc accctatcag    1260
ggggctgacc ccatccttgc gacagccctc gcctccgacc ccatccccaa ccccttcag    1320 aagtgggagc acagcgccca caagccacag agcctagaca ctgatgaccc cgcgacgctg    1380
tacgccgtgg tggagaacgt gccccgttg cgctggaagg aattcgtgcg gcgcctaggg    1440
ctgagcgacc acgagatcga tcggctggag ctgcagaacg ggcgctgcct gcgcgaggcg    1500
caatacagca tgctggcgac ctggaggcgg cgcacgccgc ggcgcgaggc cacgctggag    1560
ctgctgggac gcgtgctccg cgacatggac ctgctgggct gcctggagga catcgaggag    1620
```

```
gcgctttgcg gccccgccgc cctcccgccc gcgcccagtc ttctcagatg aggctgcgcc    1680
cctgcgggca gctctaagga ccgtcctgcg agatcgcctt ccaaccccac tttttttctgg   1740 aaaggagggg tcctgcaggg gcaagcagga gctagcagcc gcctacttgg tgctaaccccc   1800 tcgatgtaca tagcttttct cagctgcctg cgcgccgccg acagtcagcg ctgtgcgcgc    1860
ggagagaggt gcgccgtggg ctcaagagcc tgagtgggtg gtttgcgagg atgagggacg    1920
ctatgcctca tgcccgtttt gggtgtcctc accagcaagg ctgctcgggg gccctggtt     1980 cgtccctgag cctttttcac agtgcataag cagttttttt tgtttttgtt ttgttttgtt    2040
ttgtttttaa atcaatcatg ttacactaat agaaacttgg cactcctgtg ccctctgcct    2100
ggacaagcac atagcaagct gaactgtcct aaggcagggg cgagcacgga acaatggggc    2160
cttcagctgg agctgtggac ttttgtacat acactaaaat tctgaagtta aagctctgct    2220
cttggaaaaa aaaaaaaaaa aaaaaaaaaa aaaaaaaa                            2258
```

<210> SEQ ID NO 26
<211> LENGTH: 455
<212> TYPE: PRT
<213> ORGANISM: Homo sapiens

<400> SEQUENCE: 26

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
        130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
        210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255
```

```
Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
        290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 27
<211> LENGTH: 3682
<212> TYPE: DNA
<213> ORGANISM: Homo sapiens

<400> SEQUENCE: 27
gcgagcgcag cggagcctgg agagaaggcg ctgggctgcg agggcgcgag ggcgcgaggg     60
cagggggcaa ccggacccccg cccgcaccca tggcgcccgt cgccgtctgg gccgcgctgg    120
ccgtcggact ggagctctgg gctgcggcgc acgccttgcc cgcccaggtg gcatttacac    180
cctacgcccc ggagcccggg agcacatgcc ggctcagaga atactatgac cagacagctc    240
agatgtgctg cagcaaatgc tcgccgggcc aacatgcaaa agtcttctgt accaagacct    300
cggacaccgt gtgtgactcc tgtgaggaca gcacatacac ccagctctgg aactgggttc    360
ccgagtgctt gagctgtggc tcccgctgta gctctgacca ggtggaaact caagcctgca    420
ctcgggaaca gaaccgcatc tgcacctgca ggccccggctg gtactgcgcg ctgagcaagc    480
aggaggggtg ccggctgtgc gcgccgctgc gcaagtgccg cccgggcttc ggcgtggcca    540
gaccaggaac tgaaacatca gacgtggtgt gcaagccctg tgccccgggg acgttctcca    600
acacgacttc atccacggat atttgcaggc cccaccagat ctgtaacgtg gtggccatcc    660
ctgggaatgc aagcatggat gcagtctgca cgtccacgtc ccccacccgg agtatggccc    720
caggggcagt acacttaccc cagccagtgt ccacacgatc ccaacacacg cagccaactc    780
cagaacccag cactgctcca agcacctcct tcctgctccc aatgggcccc agcccccag     840 ctgaagggag cactggcgac ttcgctcttc cagttggact gattgtgggt gtgacagcct    900
tgggtctact aataatagga gtggtgaact gtgtcatcat gacccaggtg aaaaagaagc    960
```

-continued

```
ccttgtgcct gcagagagaa gccaaggtgc ctcacttgcc tgccgataag gcccgggta      1020 cacagggccc cgagcagcag cacctgctga tcacagcgcc gagctccagc agcagctccc      1080
tggagagctc ggccagtgcg ttggacagaa gggcgcccac tcggaaccag ccacaggcac      1140
caggcgtgga ggccagtggg gccggggagg cccgggccag caccgggagc tcagattctt      1200
cccctggtgg ccatgggacc caggtcaatg tcacctgcat cgtgaacgtc tgtagcagct      1260
ctgaccacag ctcacagtgc tcctcccaag ccagctccac aatgggagac acagattcca      1320
gcccctcgga gtccccgaag gacgagcagg tcccccttctc caaggaggaa tgtgcctttc     1380
ggtcacagct ggagacgcca gagaccctgc tggggagcac cgaagagaag ccctgcccc       1440 ttggagtgcc tgatgctggg atgaagccca gttaaccagg ccggtgtggg ctgtgtcgta      1500
gccaaggtgg gctgagccct ggcaggatga ccctgcgaag gggccctggt ccttccaggc      1560
ccccaccact aggactctga ggctctttct gggccaagtt cctctagtgc cctccacagc      1620
cgcagcctcc ctctgacctg caggccaaga gcagaggcag cgagttgtgg aaagcctctg      1680
ctgccatggc gtgtccctct cggaaggctg gctgggcatg gacgttcggg gcatgctggg      1740
gcaagtccct gactctctgt gacctgcccc gcccagctgc acctgccagc ctggcttctg      1800
gagcccttgg gttttttgtt tgtttgtttg tttgtttgtt tgtttctccc cctgggctct      1860
gccccagctc tggcttccag aaaaccccag catccttttc tgcagagggg ctttctggag      1920
aggagggatg ctgcctgagt cacccatgaa gacaggacag tgcttcagcc tgaggctgag      1980
actgcgggat ggtcctgggg ctctgtgcag ggaggaggtg gcagccctgt agggaacggg      2040
gtccttcaag ttagctcagg aggcttggaa agcatcacct caggccaggt gcagtggctc      2100
acgcctatga tcccagcact ttgggaggct gaggcgggtg gatcacctga ggttaggagt      2160
tcgagaccag cctggccaac atggtaaaac cccatctcta ctaaaaatac agaaattagc      2220
cgggcgtggt ggcgggcacc tatagtccca gctactcaga agcctgaggc tgggaaatcg      2280
tttgaacccg ggaagcggag gttgcaggga gccgagatca cgccactgca ctccagcctg      2340
ggcgacagag cgagagtctg tctcaaaaga aaaaaaaaag caccgcctcc aaatgccaac      2400
ttgtcctttt gtaccatggt gtgaaagtca gatgcccaga gggcccaggc aggccaccat      2460
attcagtgct gtggcctggg caagataacg cacttctaac tagaaatctg ccaattttttt    2520 aaaaaagtaa gtaccactca ggccaacaag ccaacgacaa agccaaactc tgccagccac      2580
atccaacccc ccacctgcca tttgcaccct ccgccttcac tccggtgtgc ctgcagcccc      2640
gcgcctcctt ccttgctgtc ctaggccaca ccatctcctt tcagggaatt tcaggaacta      2700
gagatgactg agtcctcgta gccatctctc tactcctacc tcagcctaga ccctcctcct      2760
cccccagagg ggtgggttcc tcttccccac tccccacctt caattcctgg gccccaaacg      2820
ggctgccctg ccactttggt acatggccag tgtgatccca agtgccagtc ttgtgtctgc      2880
gtctgtgttg cgtgtcgtgg gtgtgtgtag ccaaggtcgg taagttgaat ggcctgcctt      2940
gaagccactg aagctgggat tcctccccat tagagtcagc cttccccctc ccagggccag      3000
ggccctgcag aggggaaacc agtgtagcct tgcccggatt ctgggaggaa gcaggttgag      3060
gggctcctgg aaaggctcag tctcaggagc atggggataa aggagaaggc atgaaattgt      3120
ctagcagagc aggggcaggg tgataaattg ttgataaatt ccactggact tgagcttggc      3180
agctgaacta ttggagggtg ggagagccca gccattacca tggagacaag aagggttttc      3240
caccctggaa tcaagatgtc agactggctg gctgcagtga cgtgcacctg tactcaggag      3300
gctgagggga ggatcactgg agcccaggag tttgaggctg cagcgagcta tgatcgcgcc      3360
```

-continued

```
actacactcc agcctgagca acagagtgag accctgtctc ttaaagaaaa aaaaagtcag    3420
actgctggga ctggccaggt ttctgcccac attggaccca catgaggaca tgatggagcg    3480
cacctgcccc ctggtggaca gtcctgggag aacctcaggc ttccttggca tcacagggca    3540
gagccgggaa gcgatgaatt tggagactct gtggggcctt ggttcccttg tgtgtgtgtg    3600
ttgatcccaa gacaatgaaa gtttgcactg tatgctggac ggcattcctg cttatcaata    3660
aacctgtttg ttttaaaaaa aa                                             3682
```

<210> SEQ ID NO 28
<211> LENGTH: 461
<212> TYPE: PRT
<213> ORGANISM: Homo sapiens

<400> SEQUENCE: 28

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
```

```
        305                 310                 315                 320
Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
            355                 360                 365

Asp Ser Ser Pro Gly Gly His Gly Thr Gln Val Asn Val Thr Cys Ile
            370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
            435                 440                 445

Leu Pro Leu Gly Val Pro Asp Ala Gly Met Lys Pro Ser
    450                 455                 460

<210> SEQ ID NO 29
<211> LENGTH: 151
<212> TYPE: PRT
<213> ORGANISM: Homo Sapiens

<400> SEQUENCE: 29

Arg Val Arg Arg Ala Val Leu Pro Gln Glu Glu Glu Gly Ser Gly Gly
1               5                   10                  15

Gly Gln Leu Val Thr Glu Val Thr Lys Lys Glu Asp Ser Cys Gln Leu
            20                  25                  30

Gly Tyr Ser Ala Gly Pro Cys Met Gly Met Thr Ser Arg Tyr Phe Tyr
            35                  40                  45

Asn Gly Thr Ser Met Ala Cys Glu Thr Phe Gln Tyr Gly Gly Cys Met
    50                  55                  60

Gly Asn Gly Asn Asn Phe Val Thr Glu Lys Glu Cys Leu Gln Thr Cys
65                  70                  75                  80

Arg Thr Val Ala Ala Cys Asn Leu Pro Ile Val Arg Gly Pro Cys Arg
                85                  90                  95

Ala Phe Ile Gln Leu Trp Ala Phe Asp Ala Val Lys Gly Lys Cys Val
            100                 105                 110

Leu Phe Pro Tyr Gly Gly Cys Gln Gly Asn Gly Asn Lys Phe Tyr Ser
            115                 120                 125

Glu Lys Glu Cys Arg Glu Tyr Cys Gly Val Pro Gly Asp Gly Asp Glu
    130                 135                 140

Glu Leu Leu Arg Phe Ser Asn
145                 150

<210> SEQ ID NO 30
<211> LENGTH: 15
<212> TYPE: PRT
<213> ORGANISM: Homo Sapiens

<400> SEQUENCE: 30

Glu Cys Val Pro Gly Glu Gln Glu Pro Glu Pro Ile Leu Ile Pro
1               5                   10                  15
```

-continued

<210> SEQ ID NO 31
<211> LENGTH: 352
<212> TYPE: PRT
<213> ORGANISM: Homo Sapiens

<400> SEQUENCE: 31

Met Arg Ser Leu Gly Ala Leu Leu Leu Leu Leu Ser Ala Cys Leu Ala
1               5                   10                  15

Val Ser Ala Gly Pro Val Pro Thr Pro Pro Asp Asn Ile Gln Val Gln
            20                  25                  30

Glu Asn Phe Asn Ile Ser Arg Ile Tyr Gly Lys Trp Tyr Asn Leu Ala
            35                  40                  45

Ile Gly Ser Thr Cys Pro Trp Leu Lys Lys Ile Met Asp Arg Met Thr
    50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
            115                 120                 125

Glu Tyr Ala Ile Phe Leu Thr Lys Lys Phe Ser Arg His His Gly Pro
    130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro Arg Val Arg Arg Ala Val Leu
            195                 200                 205

Pro Gln Glu Glu Glu Gly Ser Gly Gly Gly Gln Leu Val Thr Glu Val
    210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
            275                 280                 285

Leu Pro Ile Val Arg Gly Pro Cys Arg Ala Phe Ile Gln Leu Trp Ala
    290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Glu Leu Leu Arg Phe Ser Asn
            340                 345                 350

<210> SEQ ID NO 32
<211> LENGTH: 687
<212> TYPE: PRT
<213> ORGANISM: Homo Sapiens

```
<400> SEQUENCE: 32

Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg Trp Cys
            20                  25                  30

Ser Glu Cys His Ser Asn Ala Thr Cys Thr Glu Asp Glu Ala Val Thr
        35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
            85                  90                  95

Gly Phe Arg Leu Ser Pro Gly Leu Gly Cys Thr Asp Val Asp Glu Cys
            100                 105                 110

Ala Glu Pro Gly Leu Ser His Cys His Ala Leu Ala Thr Cys Val Asn
        115                 120                 125

Val Val Gly Ser Tyr Leu Cys Val Cys Pro Ala Gly Tyr Arg Gly Asp
    130                 135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
            165                 170                 175

His Arg Thr Leu Asp Glu Tyr Trp Arg Ser Thr Glu Tyr Gly Glu Gly
            180                 185                 190

Tyr Ala Cys Asp Thr Asp Leu Arg Gly Trp Tyr Arg Phe Val Gly Gln
            195                 200                 205

Gly Gly Ala Arg Met Ala Glu Thr Cys Val Pro Val Leu Arg Cys Asn
    210                 215                 220

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
            245                 250                 255

Leu Trp Asp Ala Ser Val Gln Val Lys Ala Cys Ala Gly Gly Tyr Tyr
            260                 265                 270

Val Tyr Asn Leu Thr Ala Pro Pro Glu Cys His Leu Ala Tyr Cys Thr
            275                 280                 285

Asp Pro Ser Ser Val Glu Gly Thr Cys Glu Glu Cys Ser Ile Asp Glu
    290                 295                 300

Asp Cys Lys Ser Asn Asn Gly Arg Trp His Cys Gln Cys Lys Gln Asp
305                 310                 315                 320

Phe Asn Ile Thr Asp Ile Ser Leu Leu Glu His Arg Leu Glu Cys Gly
            325                 330                 335

Ala Asn Asp Met Lys Val Ser Leu Gly Lys Cys Gln Leu Lys Ser Leu
            340                 345                 350

Gly Phe Asp Lys Val Phe Met Tyr Leu Ser Asp Ser Arg Cys Ser Gly
        355                 360                 365

Phe Asn Asp Arg Asp Asn Arg Asp Trp Val Ser Val Val Thr Pro Ala
    370                 375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Ile Arg Asp
            405                 410                 415
```

-continued

```
Leu Asn Ile Lys Ile Asn Phe Ala Cys Ser Tyr Pro Leu Asp Met Lys
            420                 425                 430

Val Ser Leu Lys Thr Ala Leu Gln Pro Met Val Ser Gln Thr Gln Glu
            435                 440                 445

Arg Met Leu Gly Thr Asp Glu Gly Ala Gln Leu Thr Trp Arg Lys Lys
            450                 455                 460

Ser Ala His Cys Lys Leu Leu Ala Gly Thr Ser Pro Gly Leu Ala Val
465                 470                 475                 480

Ser Trp Ser Asn Val Ala Pro Ser Ser Ala Cys Ala Leu Asn Ile Arg
                485                 490                 495

Val Gly Gly Thr Gly Met Phe Thr Val Arg Met Ala Leu Phe Gln Thr
            500                 505                 510

Pro Ser Tyr Thr Gln Pro Tyr Gln Gly Ser Ser Val Thr Leu Ser Thr
            515                 520                 525

Glu Ala Phe Leu Tyr Val Gly Thr Met Leu Asp Gly Gly Asp Leu Ser
            530                 535                 540

Arg Phe Ala Leu Leu Met Thr Asn Cys Tyr Ala Thr Pro Ser Ser Asn
545                 550                 555                 560

Ala Thr Asp Pro Leu Lys Tyr Phe Ile Ile Gln Asp Arg Cys Pro His
                565                 570                 575

Thr Arg Asp Ser Thr Ile Gln Val Val Glu Asn Gly Glu Ser Ser Gln
                580                 585                 590

Gly Arg Phe Ser Val Gln Met Phe Arg Phe Ala Gly Asn Tyr Asp Leu
            595                 600                 605

Val Tyr Leu His Cys Glu Val Tyr Leu Cys Asp Thr Met Asn Glu Lys
            610                 615                 620

Cys Lys Pro Thr Cys Ser Gly Thr Arg Phe Arg Ser Gly Ser Val Ile
625                 630                 635                 640

Asp Gln Ser Arg Val Leu Asn Leu Gly Pro Ile Thr Arg Lys Gly Val
                645                 650                 655

Gln Ala Thr Val Ser Arg Ala Phe Ser Ser Leu Gly Leu Leu Lys Val
                660                 665                 670

Trp Leu Pro Leu Leu Leu Ser Ala Thr Leu Thr Leu Thr Phe Gln
            675                 680                 685

<210> SEQ ID NO 33
<211> LENGTH: 687
<212> TYPE: PRT
<213> ORGANISM: Homo Sapiens

<400> SEQUENCE: 33

Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg Trp Cys
                20                  25                  30

Ser Glu Cys His Ser Asn Ala Thr Cys Thr Glu Asp Glu Ala Val Thr
            35                  40                  45

Thr Cys Thr Cys Gln Glu Gly Phe Thr Gly Asp Gly Leu Thr Cys Val
            50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
```

```
            100             105             110

Ala Glu Pro Gly Leu Ser His Cys His Ala Leu Ala Thr Cys Val Asn
        115             120             125

Val Val Gly Ser Tyr Leu Cys Val Cys Pro Ala Gly Tyr Arg Gly Asp
    130             135             140

Gly Trp His Cys Glu Cys Ser Pro Gly Ser Cys Gly Pro Gly Leu Asp
145             150             155             160

Cys Val Pro Glu Gly Asp Ala Leu Val Cys Ala Asp Pro Cys Gln Ala
            165             170             175

His Arg Thr Leu Asp Glu Tyr Trp Arg Ser Thr Glu Tyr Gly Glu Gly
        180             185             190

Tyr Ala Cys Asp Thr Asp Leu Arg Gly Trp Tyr Arg Phe Val Gly Gln
        195             200             205

Gly Gly Ala Arg Met Ala Glu Thr Cys Val Pro Val Leu Arg Cys Asn
    210             215             220

Thr Ala Ala Pro Met Trp Leu Asn Gly Thr His Pro Ser Ser Asp Glu
225             230             235             240

Gly Ile Val Ser Arg Lys Ala Cys Ala His Trp Ser Gly His Cys Cys
            245             250             255

Leu Trp Asp Ala Ser Val Gln Val Lys Ala Cys Ala Gly Gly Tyr Tyr
        260             265             270

Val Tyr Asn Leu Thr Ala Pro Pro Glu Cys His Leu Ala Tyr Cys Thr
        275             280             285

Asp Pro Ser Ser Val Glu Gly Thr Cys Glu Glu Cys Ser Ile Asp Glu
    290             295             300

Asp Cys Lys Ser Asn Asn Gly Arg Trp His Cys Gln Cys Lys Gln Asp
305             310             315             320

Phe Asn Ile Thr Asp Ile Ser Leu Leu Glu His Arg Leu Glu Cys Gly
            325             330             335

Ala Asn Asp Met Lys Val Ser Leu Gly Lys Cys Gln Leu Lys Ser Leu
        340             345             350

Gly Phe Asp Lys Val Phe Met Tyr Leu Ser Asp Ser Arg Cys Ser Gly
        355             360             365

Phe Asn Asp Arg Asp Asn Arg Asp Trp Val Ser Val Val Thr Pro Ala
    370             375             380

Arg Asp Gly Pro Cys Gly Thr Val Leu Thr Arg Asn Glu Thr His Ala
385             390             395             400

Thr Tyr Ser Asn Thr Leu Tyr Leu Ala Asp Glu Ile Ile Ile Arg Asp
            405             410             415

Leu Asn Ile Lys Ile Asn Phe Ala Cys Ser Tyr Pro Leu Asp Met Lys
        420             425             430

Val Ser Leu Lys Thr Ala Leu Gln Pro Met Val Ser Gln Thr Gln Glu
        435             440             445

Arg Met Leu Gly Thr Asp Glu Gly Ala Gln Leu Thr Trp Arg Lys Lys
    450             455             460

Ser Ala His Cys Lys Leu Leu Ala Gly Thr Ser Pro Gly Leu Ala Val
465             470             475             480

Ser Trp Ser Asn Val Ala Pro Ser Ala Cys Ala Leu Asn Ile Arg
            485             490             495

Val Gly Gly Thr Gly Met Phe Thr Val Arg Met Ala Leu Phe Gln Thr
        500             505             510

Pro Ser Tyr Thr Gln Pro Tyr Gln Gly Ser Ser Val Thr Leu Ser Thr
        515             520             525
```

```
Glu Ala Phe Leu Tyr Val Gly Thr Met Leu Asp Gly Gly Asp Leu Ser
    530                 535             540
```

```
Arg Phe Ala Leu Leu Met Thr Asn Cys Tyr Ala Thr Pro Ser Ser Asn
545                 550             555                 560
```

```
Ala Thr Asp Pro Leu Lys Tyr Phe Ile Ile Gln Asp Arg Cys Pro His
                565             570                 575
```

```
Thr Arg Asp Ser Thr Ile Gln Val Val Glu Asn Gly Glu Ser Ser Gln
            580             585                 590
```

```
Gly Arg Phe Ser Val Gln Met Phe Arg Phe Ala Gly Asn Tyr Asp Leu
            595             600             605
```

```
Val Tyr Leu His Cys Glu Val Tyr Leu Cys Asp Thr Met Asn Glu Lys
    610             615             620
```

```
Cys Lys Pro Thr Cys Ser Gly Thr Arg Phe Arg Ser Gly Ser Val Ile
625             630             635                 640
```

```
Asp Gln Ser Arg Val Leu Asn Leu Gly Pro Ile Thr Arg Lys Gly Val
            645             650                 655
```

```
Gln Ala Thr Val Ser Arg Ala Phe Ser Ser Leu Gly Leu Leu Lys Val
            660             665                 670
```

```
Trp Leu Pro Leu Leu Leu Ser Ala Thr Leu Thr Leu Thr Phe Gln
    675                 680             685
```

```
<210> SEQ ID NO 34
<211> LENGTH: 687
<212> TYPE: PRT
<213> ORGANISM: Homo Sapiens

<400> SEQUENCE: 34
```

```
Met Gly Gln Pro Ser Leu Thr Trp Met Leu Met Val Val Val Ala Ser
1               5               10              15
```

```
Trp Phe Ile Thr Thr Ala Ala Thr Asp Thr Ser Glu Ala Arg Trp Cys
                20              25              30
```

```
Ser Glu Cys His Ser Asn Ala Thr Cys Thr Glu Asp Glu Ala Val Thr
        35              40              45
```

```
Thr Cys Thr Cys Gln Glu Gly Phe Thr Gly Asp Gly Leu Thr Cys Val
    50              55              60
```

```
Asp Leu Asp Glu Cys Ala Ile Pro Gly Ala His Asn Cys Ser Ala Asn
65              70              75              80
```

```
Ser Ser Cys Val Asn Thr Pro Gly Ser Phe Ser Cys Val Cys Pro Glu
                85              90              95
```

```
Gly Phe Arg Leu Ser Pro Gly Leu Gly Cys Thr Asp Val Asp Glu Cys
            100             105             110
```

```
Ala Glu Pro Gly Leu Ser His Cys His Ala Leu Ala Thr Cys Val Asn
        115             120             125
```

```
Val Val Gly Ser Tyr Leu Cys Val Cys Pro Ala Gly Tyr Arg Gly Asp
    130             135             140
```

```
Gly Trp His Cys Glu Cys Ser Pro Gly Ser Cys Gly Pro Gly Leu Asp
145             150             155                 160
```

```
Cys Val Pro Glu Gly Asp Ala Leu Val Cys Ala Asp Pro Cys Gln Ala
                165             170                 175
```

```
His Arg Thr Leu Asp Glu Tyr Trp Arg Ser Thr Glu Tyr Gly Glu Gly
            180             185                 190
```

```
Tyr Ala Cys Asp Thr Asp Leu Arg Gly Trp Tyr Arg Phe Val Gly Gln
            195             200             205
```

```
Gly Gly Ala Arg Met Ala Glu Thr Cys Val Pro Val Leu Arg Cys Asn
```

```
       210                  215                  220

Thr Ala Ala Pro Met Trp Leu Asn Gly Thr His Pro Ser Ser Asp Glu
225                  230                  235                  240

Gly Ile Val Ser Arg Lys Ala Cys Ala His Trp Ser Gly His Cys Cys
                    245                  250                  255

Leu Trp Asp Ala Ser Val Gln Val Lys Ala Cys Ala Gly Gly Tyr Tyr
                260                  265                  270

Val Tyr Asn Leu Thr Ala Pro Pro Glu Cys His Leu Ala Tyr Cys Thr
                275                  280                  285

Asp Pro Ser Ser Val Glu Gly Thr Cys Glu Glu Cys Ser Ile Asp Glu
        290                  295                  300

Asp Cys Lys Ser Asn Asn Gly Arg Trp His Cys Gln Cys Lys Gln Asp
305                  310                  315                  320

Phe Asn Ile Thr Asp Ile Ser Leu Leu Glu His Arg Leu Glu Cys Gly
                325                  330                  335

Ala Asn Asp Met Lys Val Ser Leu Gly Lys Cys Gln Leu Lys Ser Leu
                340                  345                  350

Gly Phe Asp Lys Val Phe Met Tyr Leu Ser Asp Ser Arg Cys Ser Gly
            355                  360                  365

Phe Asn Asp Arg Asp Asn Arg Asp Trp Val Ser Val Val Thr Pro Ala
        370                  375                  380

Arg Asp Gly Pro Cys Gly Thr Val Leu Thr Arg Asn Glu Thr His Ala
385                  390                  395                  400

Thr Tyr Ser Asn Thr Leu Tyr Leu Ala Asp Glu Ile Ile Ile Arg Asp
                405                  410                  415

Leu Asn Ile Lys Ile Asn Phe Ala Cys Ser Tyr Pro Leu Asp Met Lys
                420                  425                  430

Val Ser Leu Lys Thr Ala Leu Gln Pro Met Val Ser Gln Thr Gln Glu
                435                  440                  445

Arg Met Leu Gly Thr Asp Glu Gly Ala Gln Leu Thr Trp Arg Lys Lys
        450                  455                  460

Ser Ala His Cys Lys Leu Leu Ala Gly Thr Ser Pro Gly Leu Ala Val
465                  470                  475                  480

Ser Trp Ser Asn Val Ala Pro Ser Ser Ala Cys Ala Leu Asn Ile Arg
                485                  490                  495

Val Gly Gly Thr Gly Met Phe Thr Val Arg Met Ala Leu Phe Gln Thr
            500                  505                  510

Pro Ser Tyr Thr Gln Pro Tyr Gln Gly Ser Ser Val Thr Leu Ser Thr
            515                  520                  525

Glu Ala Phe Leu Tyr Val Gly Thr Met Leu Asp Gly Gly Asp Leu Ser
        530                  535                  540

Arg Phe Ala Leu Leu Met Thr Asn Cys Tyr Ala Thr Pro Ser Ser Asn
545                  550                  555                  560

Ala Thr Asp Pro Leu Lys Tyr Phe Ile Ile Gln Asp Arg Cys Pro His
                565                  570                  575

Thr Arg Asp Ser Thr Ile Gln Val Val Glu Asn Gly Glu Ser Ser Gln
                580                  585                  590

Gly Arg Phe Ser Val Gln Met Phe Arg Phe Ala Gly Asn Tyr Asp Leu
            595                  600                  605

Val Tyr Leu His Cys Glu Val Tyr Leu Cys Asp Thr Met Asn Glu Lys
        610                  615                  620

Cys Lys Pro Thr Cys Ser Gly Thr Arg Phe Arg Ser Gly Ser Val Ile
625                  630                  635                  640
```

```
Asp Gln Ser Arg Val Leu Asn Leu Gly Pro Ile Thr Arg Lys Gly Val
            645                 650                 655

Gln Ala Thr Val Ser Arg Ala Phe Ser Ser Leu Gly Leu Leu Lys Val
            660                 665                 670

Trp Leu Pro Leu Leu Leu Ser Ala Thr Leu Thr Leu Thr Phe Gln
        675                 680                 685

<210> SEQ ID NO 35
<211> LENGTH: 687
<212> TYPE: PRT
<213> ORGANISM: Homo Sapiens

<400> SEQUENCE: 35

Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg Trp Cys
            20                  25                  30

Ser Glu Cys His Ser Asn Ala Thr Cys Thr Glu Asp Glu Ala Val Thr
        35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
            85                  90                  95

Gly Phe Arg Leu Ser Pro Gly Leu Gly Cys Thr Asp Val Asp Glu Cys
            100                 105                 110

Ala Glu Pro Gly Leu Ser His Cys His Ala Leu Ala Thr Cys Val Asn
        115                 120                 125

Val Val Gly Ser Tyr Leu Cys Val Cys Pro Ala Gly Tyr Arg Gly Asp
    130                 135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
            165                 170                 175

His Arg Thr Leu Asp Glu Tyr Trp Arg Ser Thr Glu Tyr Gly Glu Gly
            180                 185                 190

Tyr Ala Cys Asp Thr Asp Leu Arg Gly Trp Tyr Arg Phe Val Gly Gln
        195                 200                 205

Gly Gly Ala Arg Met Ala Glu Thr Cys Val Pro Val Leu Arg Cys Asn
    210                 215                 220

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
            245                 250                 255

Leu Trp Asp Ala Ser Val Gln Val Lys Ala Cys Ala Gly Gly Tyr Tyr
            260                 265                 270

Val Tyr Asn Leu Thr Ala Pro Pro Glu Cys His Leu Ala Tyr Cys Thr
        275                 280                 285

Asp Pro Ser Ser Val Glu Gly Thr Cys Glu Glu Cys Ser Ile Asp Glu
    290                 295                 300

Asp Cys Lys Ser Asn Asn Gly Arg Trp His Cys Gln Cys Lys Gln Asp
305                 310                 315                 320

Phe Asn Ile Thr Asp Ile Ser Leu Leu Glu His Arg Leu Glu Cys Gly
```

-continued

```
                 325                 330                 335
Ala Asn Asp Met Lys Val Ser Leu Gly Lys Cys Gln Leu Lys Ser Leu
            340                 345                 350

Gly Phe Asp Lys Val Phe Met Tyr Leu Ser Asp Ser Arg Cys Ser Gly
            355                 360                 365

Phe Asn Asp Arg Asp Asn Arg Asp Trp Val Ser Val Val Thr Pro Ala
            370                 375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Ile Arg Asp
                405                 410                 415

Leu Asn Ile Lys Ile Asn Phe Ala Cys Ser Tyr Pro Leu Asp Met Lys
            420                 425                 430

Val Ser Leu Lys Thr Ala Leu Gln Pro Met Val Ser Gln Thr Gln Glu
            435                 440                 445

Arg Met Leu Gly Thr Asp Glu Gly Ala Gln Leu Thr Trp Arg Lys Lys
            450                 455                 460

Ser Ala His Cys Lys Leu Leu Ala Gly Thr Ser Pro Gly Leu Ala Val
465                 470                 475                 480

Ser Trp Ser Asn Val Ala Pro Ser Ser Ala Cys Ala Leu Asn Ile Arg
                485                 490                 495

Val Gly Gly Thr Gly Met Phe Thr Val Arg Met Ala Leu Phe Gln Thr
                500                 505                 510

Pro Ser Tyr Thr Gln Pro Tyr Gln Gly Ser Ser Val Thr Leu Ser Thr
                515                 520                 525

Glu Ala Phe Leu Tyr Val Gly Thr Met Leu Asp Gly Gly Asp Leu Ser
            530                 535                 540

Arg Phe Ala Leu Leu Met Thr Asn Cys Tyr Ala Thr Pro Ser Ser Asn
545                 550                 555                 560

Ala Thr Asp Pro Leu Lys Tyr Phe Ile Ile Gln Asp Arg Cys Pro His
                565                 570                 575

Thr Arg Asp Ser Thr Ile Gln Val Val Glu Asn Gly Glu Ser Ser Gln
                580                 585                 590

Gly Arg Phe Ser Val Gln Met Phe Arg Phe Ala Gly Asn Tyr Asp Leu
                595                 600                 605

Val Tyr Leu His Cys Glu Val Tyr Leu Cys Asp Thr Met Asn Glu Lys
            610                 615                 620

Cys Lys Pro Thr Cys Ser Gly Thr Arg Phe Arg Ser Gly Ser Val Ile
625                 630                 635                 640

Asp Gln Ser Arg Val Leu Asn Leu Gly Pro Ile Thr Arg Lys Gly Val
                645                 650                 655

Gln Ala Thr Val Ser Arg Ala Phe Ser Ser Leu Gly Leu Leu Lys Val
            660                 665                 670

Trp Leu Pro Leu Leu Leu Ser Ala Thr Leu Thr Leu Thr Phe Gln
            675                 680                 685
```

<210> SEQ ID NO 36
<211> LENGTH: 687
<212> TYPE: PRT
<213> ORGANISM: Homo Sapiens

<400> SEQUENCE: 36

```
Met Gly Gln Pro Ser Leu Thr Trp Met Leu Met Val Val Val Ala Ser
1               5                   10                  15
```

-continued

```
Trp Phe Ile Thr Thr Ala Ala Thr Asp Thr Ser Glu Ala Arg Trp Cys
            20              25                  30

Ser Glu Cys His Ser Asn Ala Thr Cys Thr Glu Asp Glu Ala Val Thr
            35              40                  45

Thr Cys Thr Cys Gln Glu Gly Phe Thr Gly Asp Gly Leu Thr Cys Val
        50              55                  60

Asp Leu Asp Glu Cys Ala Ile Pro Gly Ala His Asn Cys Ser Ala Asn
65                      70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
            100             105                 110

Ala Glu Pro Gly Leu Ser His Cys His Ala Leu Ala Thr Cys Val Asn
        115             120                 125

Val Val Gly Ser Tyr Leu Cys Val Cys Pro Ala Gly Tyr Arg Gly Asp
    130             135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
            165             170                 175

His Arg Thr Leu Asp Glu Tyr Trp Arg Ser Thr Glu Tyr Gly Glu Gly
            180             185                 190

Tyr Ala Cys Asp Thr Asp Leu Arg Gly Trp Tyr Arg Phe Val Gly Gln
            195             200                 205

Gly Gly Ala Arg Met Ala Glu Thr Cys Val Pro Val Leu Arg Cys Asn
    210             215                 220

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
                245                 250                 255

Leu Trp Asp Ala Ser Val Gln Val Lys Ala Cys Ala Gly Gly Tyr Tyr
            260             265                 270

Val Tyr Asn Leu Thr Ala Pro Pro Glu Cys His Leu Ala Tyr Cys Thr
            275             280                 285

Asp Pro Ser Ser Val Glu Gly Thr Cys Glu Glu Cys Ser Ile Asp Glu
    290             295                 300

Asp Cys Lys Ser Asn Asn Gly Arg Trp His Cys Gln Cys Lys Gln Asp
305                 310                 315                 320

Phe Asn Ile Thr Asp Ile Ser Leu Leu Glu His Arg Leu Glu Cys Gly
            325             330                 335

Ala Asn Asp Met Lys Val Ser Leu Gly Lys Cys Gln Leu Lys Ser Leu
            340             345                 350

Gly Phe Asp Lys Val Phe Met Tyr Leu Ser Asp Ser Arg Cys Ser Gly
            355             360                 365

Phe Asn Asp Arg Asp Asn Arg Asp Trp Val Ser Val Val Thr Pro Ala
    370             375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Ile Arg Asp
            405             410                 415

Leu Asn Ile Lys Ile Asn Phe Ala Cys Ser Tyr Pro Leu Asp Met Lys
            420             425                 430

Val Ser Leu Lys Thr Ala Leu Gln Pro Met Val Ser Gln Thr Gln Glu
```

```
                435                 440                 445

Arg Met Leu Gly Thr Asp Glu Gly Ala Gln Leu Thr Trp Arg Lys Lys
    450                 455                 460

Ser Ala His Cys Lys Leu Leu Ala Gly Thr Ser Pro Gly Leu Ala Val
465                 470                 475                 480

Ser Trp Ser Asn Val Ala Pro Ser Ser Ala Cys Ala Leu Asn Ile Arg
                485                 490                 495

Val Gly Gly Thr Gly Met Phe Thr Val Arg Met Ala Leu Phe Gln Thr
                500                 505                 510

Pro Ser Tyr Thr Gln Pro Tyr Gln Gly Ser Ser Val Thr Leu Ser Thr
                515                 520                 525

Glu Ala Phe Leu Tyr Val Gly Thr Met Leu Asp Gly Gly Asp Leu Ser
    530                 535                 540

Arg Phe Ala Leu Leu Met Thr Asn Cys Tyr Ala Thr Pro Ser Ser Asn
545                 550                 555                 560

Ala Thr Asp Pro Leu Lys Tyr Phe Ile Ile Gln Asp Arg Cys Pro His
                565                 570                 575

Thr Arg Asp Ser Thr Ile Gln Val Val Glu Asn Gly Glu Ser Ser Gln
                580                 585                 590

Gly Arg Phe Ser Val Gln Met Phe Arg Phe Ala Gly Asn Tyr Asp Leu
                595                 600                 605

Val Tyr Leu His Cys Glu Val Tyr Leu Cys Asp Thr Met Asn Glu Lys
    610                 615                 620

Cys Lys Pro Thr Cys Ser Gly Thr Arg Phe Arg Ser Gly Ser Val Ile
625                 630                 635                 640

Asp Gln Ser Arg Val Leu Asn Leu Gly Pro Ile Thr Arg Lys Gly Val
                645                 650                 655

Gln Ala Thr Val Ser Arg Ala Phe Ser Ser Leu Gly Leu Leu Lys Val
                660                 665                 670

Trp Leu Pro Leu Leu Leu Ser Ala Thr Leu Thr Leu Thr Phe Gln
                675                 680                 685

<210> SEQ ID NO 37
<211> LENGTH: 687
<212> TYPE: PRT
<213> ORGANISM: Homo Sapiens

<400> SEQUENCE: 37

Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg Trp Cys
                20                  25                  30

Ser Glu Cys His Ser Asn Ala Thr Cys Thr Glu Asp Glu Ala Val Thr
                35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
                100                 105                 110

Ala Glu Pro Gly Leu Ser His Cys His Ala Leu Ala Thr Cys Val Asn
                115                 120                 125
```

```
Val Val Gly Ser Tyr Leu Cys Val Cys Pro Ala Gly Tyr Arg Gly Asp
    130                 135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
                165                 170                 175

His Arg Thr Leu Asp Glu Tyr Trp Arg Ser Thr Glu Tyr Gly Glu Gly
                180                 185                 190

Tyr Ala Cys Asp Thr Asp Leu Arg Gly Trp Tyr Arg Phe Val Gly Gln
                195                 200                 205

Gly Gly Ala Arg Met Ala Glu Thr Cys Val Pro Val Leu Arg Cys Asn
    210                 215                 220

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
                245                 250                 255

Leu Trp Asp Ala Ser Val Gln Val Lys Ala Cys Ala Gly Gly Tyr Tyr
                260                 265                 270

Val Tyr Asn Leu Thr Ala Pro Pro Glu Cys His Leu Ala Tyr Cys Thr
                275                 280                 285

Asp Pro Ser Ser Val Glu Gly Thr Cys Glu Glu Cys Ser Ile Asp Glu
    290                 295                 300

Asp Cys Lys Ser Asn Asn Gly Arg Trp His Cys Gln Cys Lys Gln Asp
305                 310                 315                 320

Phe Asn Ile Thr Asp Ile Ser Leu Leu Glu His Arg Leu Glu Cys Gly
                325                 330                 335

Ala Asn Asp Met Lys Val Ser Leu Gly Lys Cys Gln Leu Lys Ser Leu
                340                 345                 350

Gly Phe Asp Lys Val Phe Met Tyr Leu Ser Asp Ser Arg Cys Ser Gly
                355                 360                 365

Phe Asn Asp Arg Asp Asn Arg Asp Trp Val Ser Val Val Thr Pro Ala
    370                 375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Ile Arg Asp
                405                 410                 415

Leu Asn Ile Lys Ile Asn Phe Ala Cys Ser Tyr Pro Leu Asp Met Lys
                420                 425                 430

Val Ser Leu Lys Thr Ala Leu Gln Pro Met Val Ser Gln Thr Gln Glu
                435                 440                 445

Arg Met Leu Gly Thr Asp Glu Gly Ala Gln Leu Thr Trp Arg Lys Lys
    450                 455                 460

Ser Ala His Cys Lys Leu Leu Ala Gly Thr Ser Pro Gly Leu Ala Val
465                 470                 475                 480

Ser Trp Ser Asn Val Ala Pro Ser Ser Ala Cys Ala Leu Asn Ile Arg
                485                 490                 495

Val Gly Gly Thr Gly Met Phe Thr Val Arg Met Ala Leu Phe Gln Thr
                500                 505                 510

Pro Ser Tyr Thr Gln Pro Tyr Gln Gly Ser Ser Val Thr Leu Ser Thr
                515                 520                 525

Glu Ala Phe Leu Tyr Val Gly Thr Met Leu Asp Gly Gly Asp Leu Ser
    530                 535                 540

Arg Phe Ala Leu Leu Met Thr Asn Cys Tyr Ala Thr Pro Ser Ser Asn
```

```
545             550             555             560

Ala Thr Asp Pro Leu Lys Tyr Phe Ile Ile Gln Asp Arg Cys Pro His
            565             570             575

Thr Arg Asp Ser Thr Ile Gln Val Val Glu Asn Gly Glu Ser Ser Gln
            580             585             590

Gly Arg Phe Ser Val Gln Met Phe Arg Phe Ala Gly Asn Tyr Asp Leu
            595             600             605

Val Tyr Leu His Cys Glu Val Tyr Leu Cys Asp Thr Met Asn Glu Lys
            610             615             620

Cys Lys Pro Thr Cys Ser Gly Thr Arg Phe Arg Ser Gly Ser Val Ile
625             630             635             640

Asp Gln Ser Arg Val Leu Asn Leu Gly Pro Ile Thr Arg Lys Gly Val
            645             650             655

Gln Ala Thr Val Ser Arg Ala Phe Ser Ser Leu Gly Leu Leu Lys Val
            660             665             670

Trp Leu Pro Leu Leu Leu Ser Ala Thr Leu Thr Leu Thr Phe Gln
            675             680             685

<210> SEQ ID NO 38
<211> LENGTH: 687
<212> TYPE: PRT
<213> ORGANISM: Homo Sapiens

<400> SEQUENCE: 38

Met Gly Gln Pro Ser Leu Thr Trp Met Leu Met Val Val Val Ala Ser
1               5               10              15

Trp Phe Ile Thr Thr Ala Ala Thr Asp Thr Ser Glu Ala Arg Trp Cys
            20              25              30

Ser Glu Cys His Ser Asn Ala Thr Cys Thr Glu Asp Glu Ala Val Thr
            35              40              45

Thr Cys Thr Cys Gln Glu Gly Phe Thr Gly Asp Gly Leu Thr Cys Val
            50              55              60

Asp Leu Asp Glu Cys Ala Ile Pro Gly Ala His Asn Cys Ser Ala Asn
65              70              75              80

Ser Ser Cys Val Asn Thr Pro Gly Ser Phe Ser Cys Val Cys Pro Glu
            85              90              95

Gly Phe Arg Leu Ser Pro Gly Leu Gly Cys Thr Asp Val Asp Glu Cys
            100             105             110

Ala Glu Pro Gly Leu Ser His Cys His Ala Leu Ala Thr Cys Val Asn
            115             120             125

Val Val Gly Ser Tyr Leu Cys Val Cys Pro Ala Gly Tyr Arg Gly Asp
            130             135             140

Gly Trp His Cys Glu Cys Ser Pro Gly Ser Cys Gly Pro Gly Leu Asp
145             150             155             160

Cys Val Pro Glu Gly Asp Ala Leu Val Cys Ala Asp Pro Cys Gln Ala
            165             170             175

His Arg Thr Leu Asp Glu Tyr Trp Arg Ser Thr Glu Tyr Gly Glu Gly
            180             185             190

Tyr Ala Cys Asp Thr Asp Leu Arg Gly Trp Tyr Arg Phe Val Gly Gln
            195             200             205

Gly Gly Ala Arg Met Ala Glu Thr Cys Val Pro Val Leu Arg Cys Asn
            210             215             220

Thr Ala Ala Pro Met Trp Leu Asn Gly Thr His Pro Ser Ser Asp Glu
225             230             235             240
```

-continued

```
Gly Ile Val Ser Arg Lys Ala Cys Ala His Trp Ser Gly His Cys Cys
            245             250             255

Leu Trp Asp Ala Ser Val Gln Val Lys Ala Cys Ala Gly Gly Tyr Tyr
            260             265             270

Val Tyr Asn Leu Thr Ala Pro Pro Glu Cys His Leu Ala Tyr Cys Thr
            275             280             285

Asp Pro Ser Ser Val Glu Gly Thr Cys Glu Glu Cys Ser Ile Asp Glu
            290             295             300

Asp Cys Lys Ser Asn Asn Gly Arg Trp His Cys Gln Cys Lys Gln Asp
    305             310             315             320

Phe Asn Ile Thr Asp Ile Ser Leu Leu Glu His Arg Leu Glu Cys Gly
            325             330             335

Ala Asn Asp Met Lys Val Ser Leu Gly Lys Cys Gln Leu Lys Ser Leu
            340             345             350

Gly Phe Asp Lys Val Phe Met Tyr Leu Ser Asp Ser Arg Cys Ser Gly
            355             360             365

Phe Asn Asp Arg Asp Asn Arg Asp Trp Val Ser Val Val Thr Pro Ala
            370             375             380

Arg Asp Gly Pro Cys Gly Thr Val Leu Thr Arg Asn Glu Thr His Ala
    385             390             395             400

Thr Tyr Ser Asn Thr Leu Tyr Leu Ala Asp Glu Ile Ile Ile Arg Asp
            405             410             415

Leu Asn Ile Lys Ile Asn Phe Ala Cys Ser Tyr Pro Leu Asp Met Lys
            420             425             430

Val Ser Leu Lys Thr Ala Leu Gln Pro Met Val Ser Gln Thr Gln Glu
            435             440             445

Arg Met Leu Gly Thr Asp Glu Gly Ala Gln Leu Thr Trp Arg Lys Lys
    450             455             460

Ser Ala His Cys Lys Leu Leu Ala Gly Thr Ser Pro Gly Leu Ala Val
465             470             475             480

Ser Trp Ser Asn Val Ala Pro Ser Ser Ala Cys Ala Leu Asn Ile Arg
            485             490             495

Val Gly Gly Thr Gly Met Phe Thr Val Arg Met Ala Leu Phe Gln Thr
            500             505             510

Pro Ser Tyr Thr Gln Pro Tyr Gln Gly Ser Ser Val Thr Leu Ser Thr
            515             520             525

Glu Ala Phe Leu Tyr Val Gly Thr Met Leu Asp Gly Gly Asp Leu Ser
            530             535             540

Arg Phe Ala Leu Leu Met Thr Asn Cys Tyr Ala Thr Pro Ser Ser Asn
545             550             555             560

Ala Thr Asp Pro Leu Lys Tyr Phe Ile Ile Gln Asp Arg Cys Pro His
            565             570             575

Thr Arg Asp Ser Thr Ile Gln Val Val Glu Asn Gly Glu Ser Ser Gln
            580             585             590

Gly Arg Phe Ser Val Gln Met Phe Arg Phe Ala Gly Asn Tyr Asp Leu
            595             600             605

Val Tyr Leu His Cys Glu Val Tyr Leu Cys Asp Thr Met Asn Glu Lys
            610             615             620

Cys Lys Pro Thr Cys Ser Gly Thr Arg Phe Arg Ser Gly Ser Val Ile
625             630             635             640

Asp Gln Ser Arg Val Leu Asn Leu Gly Pro Ile Thr Arg Lys Gly Val
            645             650             655

Gln Ala Thr Val Ser Arg Ala Phe Ser Ser Leu Gly Leu Leu Lys Val
```

```
          660             665             670
Trp Leu Pro Leu Leu Leu Ser Ala Thr Leu Thr Leu Thr Phe Gln
      675             680             685

<210> SEQ ID NO 39
<211> LENGTH: 359
<212> TYPE: PRT
<213> ORGANISM: Homo Sapiens

<400> SEQUENCE: 39

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
            35                  40                  45

Arg Gly Ser Cys Ser Leu Phe Thr Cys Gln Asn Gly Ile Val Trp Thr
      50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
      130                 135                 140

Arg Thr Ser Thr Thr Val Pro Thr Thr Thr Thr Val Pro Thr Thr Thr
145                 150                 155                 160

Val Pro Thr Thr Met Ser Ile Pro Thr Thr Thr Thr Val Leu Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Thr Val Ser Thr Phe Val Pro
            195                 200                 205

Pro Met Pro Leu Pro Arg Gln Asn His Glu Pro Val Ala Thr Ser Pro
      210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
            275                 280                 285

Lys Gly Ile Tyr Ala Gly Val Cys Ile Ser Val Leu Val Leu Leu Ala
      290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
            340                 345                 350
```

-continued

```
Asn Ser Leu Tyr Ala Thr Asp
        355

<210> SEQ ID NO 40
<211> LENGTH: 401
<212> TYPE: PRT
<213> ORGANISM: Homo Sapiens

<400> SEQUENCE: 40

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
                20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
                100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
            195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
                260                 265                 270

Leu Trp Asn Asn Asn Gln Thr Gln Leu Phe Leu Glu His Ser Leu Leu
            275                 280                 285

Thr Ala Asn Thr Thr Lys Gly Ile Tyr Ala Gly Val Cys Ile Ser Val
    290                 295                 300

Leu Val Leu Leu Ala Leu Leu Gly Val Ile Ile Ala Lys Met Phe His
305                 310                 315                 320

Leu Ala Ala Phe Lys Leu Lys Leu Cys Lys Met Gln Leu Lys Arg Lys
                325                 330                 335

Ser Lys Gln Lys Thr Ile Ser Thr Leu Arg Ile Val Phe Met Pro Arg
            340                 345                 350

Thr Lys Thr Gln Trp Cys Ser Leu Arg Val Tyr Ala His Glu Cys Arg
        355                 360                 365
```

-continued

```
Arg Leu Asn Arg His Gln His Ile Arg Arg Leu Leu Asp Pro Lys Thr
    370                 375                 380

Ile Phe Leu Phe Gln Phe His Leu Ala Phe Gln His Val Ser Asp Thr
385                 390                 395                 400

Gly

<210> SEQ ID NO 41
<211> LENGTH: 364
<212> TYPE: PRT
<213> ORGANISM: Homo Sapiens

<400> SEQUENCE: 41

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Met Thr Thr
145                 150                 155                 160

Val Pro Thr Thr Thr Val Pro Thr Thr Met Ser Ile Pro Thr Thr Thr
            165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
            195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
                260                 265                 270

Leu Trp Asn Asn Asn Gln Thr Gln Leu Phe Leu Glu His Ser Leu Leu
            275                 280                 285

Thr Ala Asn Thr Thr Lys Gly Ile Tyr Ala Gly Val Cys Ile Ser Val
            290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335
```

-continued

```
Ile Lys Ala Leu Gln Asn Ala Val Glu Lys Glu Val Gln Ala Glu Asp
        340                 345                 350

Asn Ile Tyr Ile Glu Asn Ser Leu Tyr Ala Thr Asp
        355                 360

<210> SEQ ID NO 42
<211> LENGTH: 364
<212> TYPE: PRT
<213> ORGANISM: Homo Sapiens

<400> SEQUENCE: 42

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
            35                  40                  45

Arg Gly Ser Cys Ser Leu Phe Thr Cys Gln Asn Gly Ile Val Trp Thr
        50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
        130                 135                 140

Arg Thr Ser Thr Thr Val Pro Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
            195                 200                 205

Ser Thr Phe Val Pro Pro Met Pro Leu Pro Arg Gln Asn His Glu Pro
        210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
            260                 265                 270

Leu Trp Asn Asn Asn Gln Thr Gln Leu Phe Leu Glu His Ser Leu Leu
        275                 280                 285

Thr Ala Asn Thr Thr Lys Gly Ile Tyr Ala Gly Val Cys Ile Ser Val
        290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
            325                 330                 335

Ile Lys Ala Leu Gln Asn Ala Val Glu Lys Glu Val Gln Ala Glu Asp
```

-continued

```
                 340              345              350

Asn Ile Tyr Ile Glu Asn Ser Leu Tyr Ala Thr Asp
        355              360

<210> SEQ ID NO 43
<211> LENGTH: 401
<212> TYPE: PRT
<213> ORGANISM: Homo Sapiens

<400> SEQUENCE: 43

Met His Pro Gln Val Val Ile Leu Ser Leu Ile Leu His Leu Ala Asp
1               5                  10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
            195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
            260                 265                 270

Leu Trp Asn Asn Asn Gln Thr Gln Leu Phe Leu Glu His Ser Leu Leu
        275                 280                 285

Thr Ala Asn Thr Thr Lys Gly Ile Tyr Ala Gly Val Cys Ile Ser Val
        290                 295                 300

Leu Val Leu Leu Ala Leu Leu Gly Val Ile Ile Ala Lys Met Phe His
305                 310                 315                 320

Leu Ala Ala Phe Lys Leu Lys Leu Cys Lys Met Gln Leu Lys Arg Lys
                325                 330                 335

Ser Lys Gln Lys Thr Ile Ser Thr Leu Arg Ile Val Phe Met Pro Arg
            340                 345                 350
```

```
Thr Lys Thr Gln Trp Cys Ser Leu Arg Val Tyr Ala His Glu Cys Arg
        355             360             365

Arg Leu Asn Arg His Gln His Ile Arg Arg Leu Leu Asp Pro Lys Thr
        370             375             380

Ile Phe Leu Phe Gln Phe His Leu Ala Phe Gln His Val Ser Asp Thr
385             390             395             400

Gly

<210> SEQ ID NO 44
<211> LENGTH: 401
<212> TYPE: PRT
<213> ORGANISM: Homo Sapiens

<400> SEQUENCE: 44

Met His Pro Gln Val Val Ile Leu Ser Leu Ile Leu His Leu Ala Asp
1               5               10              15

Ser Val Ala Gly Ser Val Lys Val Gly Gly Glu Ala Gly Pro Ser Val
                20              25              30

Thr Leu Pro Cys His Tyr Ser Gly Ala Val Thr Ser Met Cys Trp Asn
        35              40              45

Arg Gly Ser Cys Ser Leu Phe Thr Cys Gln Asn Gly Ile Val Trp Thr
        50              55              60

Asn Gly Thr His Val Thr Tyr Arg Lys Asp Thr Arg Tyr Lys Leu Leu
65              70              75              80

Gly Asp Leu Ser Arg Arg Asp Val Ser Leu Thr Ile Glu Asn Thr Ala
                85              90              95

Val Ser Asp Ser Gly Val Tyr Cys Cys Arg Val Glu His Arg Gly Trp
                100             105             110

Phe Asn Asp Met Lys Ile Thr Val Ser Leu Glu Ile Val Pro Pro Lys
        115             120             125

Val Thr Thr Thr Pro Ile Val Thr Thr Val Pro Thr Val Thr Thr Val
        130             135             140

Arg Thr Ser Thr Thr Val Pro Thr Thr Thr Thr Val Pro Met Thr Thr
145             150             155             160

Val Pro Thr Thr Thr Val Pro Thr Thr Met Ser Ile Pro Thr Thr Thr
                165             170             175

Thr Val Leu Thr Thr Met Thr Val Ser Thr Thr Thr Ser Val Pro Thr
                180             185             190

Thr Thr Ser Ile Pro Thr Thr Thr Ser Val Pro Val Thr Thr Thr Val
        195             200             205

Ser Thr Phe Val Pro Pro Met Pro Leu Pro Arg Gln Asn His Glu Pro
        210             215             220

Val Ala Thr Ser Pro Ser Ser Pro Gln Pro Ala Glu Thr His Pro Thr
225             230             235             240

Thr Leu Gln Gly Ala Ile Arg Arg Glu Pro Thr Ser Ser Pro Leu Tyr
                245             250             255

Ser Tyr Thr Thr Asp Gly Asn Asp Thr Val Thr Glu Ser Ser Asp Gly
                260             265             270

Leu Trp Asn Asn Asn Gln Thr Gln Leu Phe Leu Glu His Ser Leu Leu
        275             280             285

Thr Ala Asn Thr Thr Lys Gly Ile Tyr Ala Gly Val Cys Ile Ser Val
        290             295             300

Leu Val Leu Leu Ala Leu Leu Gly Val Ile Ile Ala Lys Met Phe His
305             310             315             320
```

```
Leu Ala Ala Phe Lys Leu Lys Leu Cys Lys Met Gln Leu Lys Arg Lys
                325             330             335

Ser Lys Gln Lys Thr Ile Ser Thr Leu Arg Ile Val Phe Met Pro Arg
            340             345             350

Thr Lys Thr Gln Trp Cys Ser Leu Arg Val Tyr Ala His Glu Cys Arg
            355             360             365

Arg Leu Asn Arg His Gln His Ile Arg Arg Leu Leu Asp Pro Lys Thr
    370             375             380

Ile Phe Leu Phe Gln Phe His Leu Ala Phe Gln His Val Ser Asp Thr
385             390             395             400

Gly

<210> SEQ ID NO 45
<211> LENGTH: 401
<212> TYPE: PRT
<213> ORGANISM: Homo Sapiens

<400> SEQUENCE: 45

Met His Pro Gln Val Val Ile Leu Ser Leu Ile Leu His Leu Ala Asp
1               5               10              15

Ser Val Ala Gly Ser Val Lys Val Gly Gly Glu Ala Gly Pro Ser Val
            20              25              30

Thr Leu Pro Cys His Tyr Ser Gly Ala Val Thr Ser Met Cys Trp Asn
            35              40              45

Arg Gly Ser Cys Ser Leu Phe Thr Cys Gln Asn Gly Ile Val Trp Thr
    50              55              60

Asn Gly Thr His Val Thr Tyr Arg Lys Asp Thr Arg Tyr Lys Leu Leu
65              70              75              80

Gly Asp Leu Ser Arg Arg Asp Val Ser Leu Thr Ile Glu Asn Thr Ala
            85              90              95

Val Ser Asp Ser Gly Val Tyr Cys Cys Arg Val Glu His Arg Gly Trp
            100             105             110

Phe Asn Asp Met Lys Ile Thr Val Ser Leu Glu Ile Val Pro Pro Lys
            115             120             125

Val Thr Thr Thr Pro Ile Val Thr Thr Val Pro Thr Val Thr Thr Val
            130             135             140

Arg Thr Ser Thr Thr Val Pro Thr Thr Thr Val Pro Met Thr Thr
145             150             155             160

Val Pro Thr Thr Thr Val Pro Thr Thr Met Ser Ile Pro Thr Thr Thr
            165             170             175

Thr Val Leu Thr Thr Met Thr Val Ser Thr Thr Thr Ser Val Pro Thr
            180             185             190

Thr Thr Ser Ile Pro Thr Thr Thr Ser Val Pro Val Thr Thr Thr Val
            195             200             205

Ser Thr Phe Val Pro Pro Met Pro Leu Pro Arg Gln Asn His Glu Pro
            210             215             220

Val Ala Thr Ser Pro Ser Ser Pro Gln Pro Ala Glu Thr His Pro Thr
225             230             235             240

Thr Leu Gln Gly Ala Ile Arg Arg Glu Pro Thr Ser Ser Pro Leu Tyr
            245             250             255

Ser Tyr Thr Thr Asp Gly Asn Asp Thr Val Thr Glu Ser Ser Asp Gly
            260             265             270

Leu Trp Asn Asn Asn Gln Thr Gln Leu Phe Leu Glu His Ser Leu Leu
            275             280             285
```

-continued

```
Thr Ala Asn Thr Thr Lys Gly Ile Tyr Ala Gly Val Cys Ile Ser Val
    290                 295                 300

Leu Val Leu Leu Ala Leu Leu Gly Val Ile Ile Ala Lys Met Phe His
305                 310                 315                 320

Leu Ala Ala Phe Lys Leu Lys Leu Cys Lys Met Gln Leu Lys Arg Lys
                325                 330                 335

Ser Lys Gln Lys Thr Ile Ser Thr Leu Arg Ile Val Phe Met Pro Arg
                340                 345                 350

Thr Lys Thr Gln Trp Cys Ser Leu Arg Val Tyr Ala His Glu Cys Arg
                355                 360                 365

Arg Leu Asn Arg His Gln His Ile Arg Arg Leu Leu Asp Pro Lys Thr
    370                 375                 380

Ile Phe Leu Phe Gln Phe His Leu Ala Phe Gln His Val Ser Asp Thr
385                 390                 395                 400

Gly
```

```
<210> SEQ ID NO 46
<211> LENGTH: 401
<212> TYPE: PRT
<213> ORGANISM: Homo Sapiens

<400> SEQUENCE: 46
```

```
Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
                20                  25                  30

Thr Leu Pro Cys His Tyr Ser Gly Ala Val Thr Ser Met Cys Trp Asn
                35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
                100                 105                 110

Phe Asn Asp Met Lys Ile Thr Val Ser Leu Glu Ile Val Pro Pro Lys
                115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Thr Ser Val Pro Thr
                180                 185                 190

Thr Thr Ser Ile Pro Thr Thr Thr Ser Val Pro Val Thr Thr Thr Val
                195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255
```

```
Ser Tyr Thr Thr Asp Gly Asn Asp Thr Val Thr Glu Ser Ser Asp Gly
            260                 265                 270

Leu Trp Asn Asn Asn Gln Thr Gln Leu Phe Leu Glu His Ser Leu Leu
            275                 280                 285

Thr Ala Asn Thr Thr Lys Gly Ile Tyr Ala Gly Val Cys Ile Ser Val
            290                 295                 300

Leu Val Leu Leu Ala Leu Leu Gly Val Ile Ile Ala Lys Met Phe His
305                 310                 315                 320

Leu Ala Ala Phe Lys Leu Lys Leu Cys Lys Met Gln Leu Lys Arg Lys
                325                 330                 335

Ser Lys Gln Lys Thr Ile Ser Thr Leu Arg Ile Val Phe Met Pro Arg
            340                 345                 350

Thr Lys Thr Gln Trp Cys Ser Leu Arg Val Tyr Ala His Glu Cys Arg
            355                 360                 365

Arg Leu Asn Arg His Gln His Ile Arg Arg Leu Leu Asp Pro Lys Thr
            370                 375                 380

Ile Phe Leu Phe Gln Phe His Leu Ala Phe Gln His Val Ser Asp Thr
385                 390                 395                 400

Gly

<210> SEQ ID NO 47
<211> LENGTH: 401
<212> TYPE: PRT
<213> ORGANISM: Homo Sapiens

<400> SEQUENCE: 47

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
            35                  40                  45

Arg Gly Ser Cys Ser Leu Phe Thr Cys Gln Asn Gly Ile Val Trp Thr
            50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
            130                 135                 140

Arg Thr Ser Thr Thr Val Pro Thr Thr Thr Val Pro Met Thr Thr
145                 150                 155                 160

Val Pro Thr Thr Thr Val Pro Thr Thr Met Ser Ile Pro Thr Thr Thr
            165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
            195                 200                 205

Ser Thr Phe Val Pro Pro Met Pro Leu Pro Arg Gln Asn His Glu Pro
            210                 215                 220
```

-continued

```
Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
                260                 265                 270

Leu Trp Asn Asn Asn Gln Thr Gln Leu Phe Leu Glu His Ser Leu Leu
                275                 280                 285

Thr Ala Asn Thr Thr Lys Gly Ile Tyr Ala Gly Val Cys Ile Ser Val
                290                 295                 300

Leu Val Leu Leu Ala Leu Leu Gly Val Ile Ile Ala Lys Met Phe His
305                 310                 315                 320

Leu Ala Ala Phe Lys Leu Lys Leu Cys Lys Met Gln Leu Lys Arg Lys
                325                 330                 335

Ser Lys Gln Lys Thr Ile Ser Thr Leu Arg Ile Val Phe Met Pro Arg
                340                 345                 350

Thr Lys Thr Gln Trp Cys Ser Leu Arg Val Tyr Ala His Glu Cys Arg
                355                 360                 365

Arg Leu Asn Arg His Gln His Ile Arg Arg Leu Leu Asp Pro Lys Thr
370                 375                 380

Ile Phe Leu Phe Gln Phe His Leu Ala Phe Gln His Val Ser Asp Thr
385                 390                 395                 400

Gly
```

<210> SEQ ID NO 48
<211> LENGTH: 400
<212> TYPE: PRT
<213> ORGANISM: Homo Sapiens

<400> SEQUENCE: 48

```
Met His Pro Gln Val Val Ile Leu Ser Leu Ile Leu His Leu Ala Asp
1                   5                   10                  15

Ser Val Ala Gly Ser Val Lys Val Gly Gly Glu Ala Gly Pro Ser Val
                20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
        50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
                100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
        130                 135                 140

Arg Thr Ser Thr Thr Val Pro Thr Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Thr Ser Val Pro Thr
                180                 185                 190
```

```
Thr Thr Ser Ile Pro Thr Thr Thr Ser Val Pro Val Thr Thr Thr Val
        195                 200                 205

Ser Thr Phe Val Pro Pro Met Pro Leu Pro Arg Gln Asn His Glu Pro
    210                 215                 220

Ala Thr Ser Pro Ser Ser Pro Gln Pro Ala Glu Thr His Pro Thr Thr
225                 230                 235                 240

Leu Gln Gly Ala Ile Arg Arg Glu Pro Thr Ser Ser Pro Leu Tyr Ser
                245                 250                 255

Tyr Thr Thr Asp Gly Asn Asp Thr Val Thr Glu Ser Ser Asp Gly Leu
                260                 265                 270

Trp Asn Asn Asn Gln Thr Gln Leu Phe Leu Glu His Ser Leu Leu Thr
                275                 280                 285

Ala Asn Thr Thr Lys Gly Ile Tyr Ala Gly Val Cys Ile Ser Val Leu
    290                 295                 300

Val Leu Leu Ala Leu Leu Gly Val Ile Ile Ala Lys Met Phe His Leu
305                 310                 315                 320

Ala Ala Phe Lys Leu Lys Leu Cys Lys Met Gln Leu Lys Arg Lys Ser
                325                 330                 335

Lys Gln Lys Thr Ile Ser Thr Leu Arg Ile Val Phe Met Pro Arg Thr
                340                 345                 350

Lys Thr Gln Trp Cys Ser Leu Arg Val Tyr Ala His Glu Cys Arg Arg
                355                 360                 365

Leu Asn Arg His Gln His Ile Arg Arg Leu Leu Asp Pro Lys Thr Ile
    370                 375                 380

Phe Leu Phe Gln Phe His Leu Ala Phe Gln His Val Ser Asp Thr Gly
385                 390                 395                 400

<210> SEQ ID NO 49
<211> LENGTH: 244
<212> TYPE: PRT
<213> ORGANISM: Homo Sapiens

<400> SEQUENCE: 49

Met Thr Thr Val Pro Thr Thr Thr Val Pro Thr Thr Met Ser Ile Pro
1                   5                   10                  15

Thr Thr Thr Thr Val Leu Thr Thr Met Thr Val Ser Thr Thr Thr Ser
                20                  25                  30

Val Pro Thr Thr Thr Ser Ile Pro Thr Thr Thr Ser Val Pro Val Thr
            35                  40                  45

Thr Thr Val Ser Thr Phe Val Pro Pro Met Pro Leu Pro Arg Gln Asn
    50                  55                  60

His Glu Pro Val Ala Thr Ser Pro Ser Ser Pro Gln Pro Ala Glu Thr
65                  70                  75                  80

His Pro Thr Thr Leu Gln Gly Ala Ile Arg Arg Glu Pro Thr Ser Ser
                85                  90                  95

Pro Leu Tyr Ser Tyr Thr Thr Asp Gly Asn Asp Thr Val Thr Glu Ser
            100                 105                 110

Ser Asp Gly Leu Trp Asn Asn Asn Gln Thr Gln Leu Phe Leu Glu His
        115                 120                 125

Ser Leu Leu Thr Ala Asn Thr Thr Lys Gly Ile Tyr Ala Gly Val Cys
    130                 135                 140

Ile Ser Val Leu Val Leu Leu Ala Leu Leu Gly Val Ile Ile Ala Lys
145                 150                 155                 160

Met Phe His Leu Ala Ala Phe Lys Leu Lys Leu Cys Lys Met Gln Leu
                165                 170                 175
```

```
Lys Arg Lys Ser Lys Gln Lys Thr Ile Ser Thr Leu Arg Ile Val Phe
            180                 185                 190

Met Pro Arg Thr Lys Thr Gln Trp Cys Ser Leu Arg Val Tyr Ala His
            195                 200                 205

Glu Cys Arg Arg Leu Asn Arg His Gln His Ile Arg Arg Leu Leu Asp
            210                 215                 220

Pro Lys Thr Ile Phe Leu Phe Gln Phe His Leu Ala Phe Gln His Val
225                 230                 235                 240

Ser Asp Thr Gly

<210> SEQ ID NO 50
<211> LENGTH: 364
<212> TYPE: PRT
<213> ORGANISM: Homo Sapiens

<400> SEQUENCE: 50

Met His Pro Gln Val Val Ile Leu Ser Leu Ile Leu His Leu Ala Asp
1                   5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
            35                  40                  45

Arg Gly Ser Cys Ser Leu Phe Thr Cys Gln Asn Gly Ile Val Trp Thr
            50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
            85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
            130                 135                 140

Arg Thr Ser Thr Thr Val Pro Thr Thr Thr Thr Val Pro Met Thr Thr
145                 150                 155                 160

Val Pro Thr Thr Thr Val Pro Thr Thr Met Ser Ile Pro Thr Thr Thr
            165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
            195                 200                 205

Ser Thr Phe Val Pro Pro Met Pro Leu Pro Arg Gln Asn His Glu Pro
            210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                    245                 250                 255

Ser Tyr Thr Thr Asp Gly Asn Asp Thr Val Thr Glu Ser Ser Asp Gly
            260                 265                 270

Leu Trp Asn Asn Asn Gln Thr Gln Leu Phe Leu Glu His Ser Leu Leu
            275                 280                 285

Thr Ala Asn Thr Thr Lys Gly Ile Tyr Ala Gly Val Cys Ile Ser Val
            290                 295                 300
```

```
Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
                340                 345                 350

Asn Ile Tyr Ile Glu Asn Ser Leu Tyr Ala Thr Asp
            355                 360
```

<210> SEQ ID NO 51
<211> LENGTH: 380
<212> TYPE: PRT
<213> ORGANISM: Homo Sapiens

<400> SEQUENCE: 51

```
Met Gly Ala Thr Thr Met Asp Gln Lys Ser Leu Trp Ala Gly Ser Ala
1               5                   10                  15

Tyr Lys Leu Val Cys Tyr Phe Thr Asn Trp Ser Gln Asp Arg Gln Glu
                20                  25                  30

Pro Gly Lys Phe Thr Pro Glu Asn Ile Asp Pro Phe Leu Cys Ser His
            35                  40                  45

Leu Ile Tyr Ser Phe Ala Ser Ile Glu Asn Asn Lys Val Ile Ile Lys
        50                  55                  60

Asp Lys Ser Glu Val Met Leu Tyr Gln Thr Ile Asn Ser Leu Lys Thr
65                  70                  75                  80

Lys Asn Pro Lys Leu Lys Ile Leu Leu Ser Ile Gly Gly Tyr Leu Phe
                85                  90                  95

Gly Ser Lys Gly Phe His Pro Met Val Asp Ser Ser Thr Ser Arg Leu
                100                 105                 110

Glu Phe Ile Asn Ser Ile Ile Leu Phe Leu Arg Asn His Asn Phe Asp
            115                 120                 125

Gly Leu Asp Val Ser Trp Ile Tyr Pro Asp Gln Lys Glu Asn Thr His
        130                 135                 140

Phe Thr Val Leu Ile His Glu Leu Ala Glu Ala Phe Gln Lys Asp Phe
145                 150                 155                 160

Thr Lys Ser Thr Lys Glu Arg Leu Leu Leu Thr Ala Gly Val Ser Ala
                165                 170                 175

Gly Arg Gln Met Ile Asp Asn Ser Tyr Gln Val Glu Lys Leu Ala Lys
                180                 185                 190

Asp Leu Asp Phe Ile Asn Leu Leu Ser Phe Asp Phe His Gly Ser Trp
            195                 200                 205

Glu Lys Pro Leu Ile Thr Gly His Asn Ser Pro Leu Ser Lys Gly Trp
        210                 215                 220

Gln Asp Arg Gly Pro Ser Ser Tyr Tyr Asn Val Glu Tyr Ala Val Gly
225                 230                 235                 240

Tyr Trp Ile His Lys Gly Met Pro Ser Glu Lys Val Val Met Gly Ile
                245                 250                 255

Pro Thr Tyr Gly His Ser Phe Thr Leu Ala Ser Ala Glu Thr Thr Val
                260                 265                 270

Gly Ala Pro Ala Ser Gly Pro Gly Ala Ala Gly Pro Ile Thr Glu Ser
                275                 280                 285

Ser Gly Phe Leu Ala Tyr Tyr Glu Ile Cys Gln Phe Leu Lys Gly Ala
        290                 295                 300

Lys Ile Thr Arg Leu Gln Asp Gln Gln Val Pro Tyr Ala Val Lys Gly
```

```
305              310              315              320

Asn Gln Trp Val Gly Tyr Asp Asp Val Lys Ser Met Glu Thr Lys Val
                325              330              335

Gln Phe Leu Lys Asn Leu Asn Leu Gly Gly Ala Met Ile Trp Ser Ile
        340              345              350

Asp Met Asp Asp Phe Thr Gly Lys Ser Cys Asn Gln Gly Pro Tyr Pro
        355              360              365

Leu Val Gln Ala Val Lys Arg Ser Leu Gly Ser Leu
    370              375              380

<210> SEQ ID NO 52
<211> LENGTH: 311
<212> TYPE: PRT
<213> ORGANISM: Homo Sapiens

<400> SEQUENCE: 52

Met Leu Tyr Gln Thr Ile Asn Ser Leu Lys Thr Lys Asn Pro Lys Leu
1               5               10              15

Lys Ile Leu Leu Ser Ile Gly Gly Tyr Leu Phe Gly Ser Lys Gly Phe
        20              25              30

His Pro Met Val Asp Ser Ser Thr Ser Arg Leu Glu Phe Ile Asn Ser
        35              40              45

Ile Ile Leu Phe Leu Arg Asn His Asn Phe Asp Gly Leu Asp Val Ser
    50              55              60

Trp Ile Tyr Pro Asp Gln Lys Glu Asn Thr His Phe Thr Val Leu Ile
65              70              75              80

His Glu Leu Ala Glu Ala Phe Gln Lys Asp Phe Thr Lys Ser Thr Lys
                85              90              95

Glu Arg Leu Leu Leu Thr Ala Gly Val Ser Ala Gly Arg Gln Met Ile
        100             105             110

Asp Asn Ser Tyr Gln Val Glu Lys Leu Ala Lys Asp Leu Asp Phe Ile
        115             120             125

Asn Leu Leu Ser Phe Asp Phe His Gly Ser Trp Glu Lys Pro Leu Ile
        130             135             140

Thr Gly His Asn Ser Pro Leu Ser Lys Gly Trp Gln Asp Arg Gly Pro
145             150             155             160

Ser Ser Tyr Tyr Asn Val Glu Tyr Ala Val Gly Tyr Trp Ile His Lys
                165             170             175

Gly Met Pro Ser Glu Lys Val Val Met Gly Ile Pro Thr Tyr Gly His
        180             185             190

Ser Phe Thr Leu Ala Ser Ala Glu Thr Thr Val Gly Ala Pro Ala Ser
        195             200             205

Gly Pro Gly Ala Ala Gly Pro Ile Thr Glu Ser Ser Gly Phe Leu Ala
    210             215             220

Tyr Tyr Glu Ile Cys Gln Phe Leu Lys Gly Ala Lys Ile Thr Arg Leu
225             230             235             240

Gln Asp Gln Gln Val Pro Tyr Ala Val Lys Gly Asn Gln Trp Val Gly
                245             250             255

Tyr Asp Asp Val Lys Ser Met Glu Thr Lys Val Gln Phe Leu Lys Asn
        260             265             270

Leu Asn Leu Gly Gly Ala Met Ile Trp Ser Ile Asp Met Asp Asp Phe
        275             280             285

Thr Gly Lys Ser Cys Asn Gln Gly Pro Tyr Pro Leu Val Gln Ala Val
    290             295             300
```

```
Lys Arg Ser Leu Gly Ser Leu
305                 310

<210> SEQ ID NO 53
<211> LENGTH: 380
<212> TYPE: PRT
<213> ORGANISM: Homo Sapiens

<400> SEQUENCE: 53

Met Gly Ala Thr Thr Met Asp Gln Lys Ser Leu Trp Ala Gly Ser Ala
1               5                   10                  15

Tyr Lys Leu Val Cys Tyr Phe Thr Asn Trp Ser Gln Asp Arg Gln Glu
            20                  25                  30

Pro Gly Lys Phe Thr Pro Glu Asn Ile Asp Pro Phe Leu Cys Ser His
        35                  40                  45

Leu Ile Tyr Ser Phe Ala Ser Ile Glu Asn Asn Lys Val Ile Ile Lys
    50                  55                  60

Asp Lys Ser Glu Val Met Leu Tyr Gln Thr Ile Asn Ser Leu Lys Thr
65                  70                  75                  80

Lys Asn Pro Lys Leu Lys Ile Leu Leu Ser Ile Gly Gly Tyr Leu Phe
                85                  90                  95

Gly Ser Lys Gly Phe His Pro Met Val Asp Ser Ser Thr Ser Arg Leu
            100                 105                 110

Glu Phe Ile Asn Ser Ile Ile Leu Phe Leu Arg Asn His Asn Phe Asp
            115                 120                 125

Gly Leu Asp Val Ser Trp Ile Tyr Pro Asp Gln Lys Glu Asn Thr His
        130                 135                 140

Phe Thr Val Leu Ile His Glu Leu Ala Glu Ala Phe Gln Lys Asp Phe
145                 150                 155                 160

Thr Lys Ser Thr Lys Glu Arg Leu Leu Leu Thr Ala Gly Val Ser Ala
            165                 170                 175

Gly Arg Gln Met Ile Asp Asn Ser Tyr Gln Val Glu Lys Leu Ala Lys
            180                 185                 190

Asp Leu Asp Phe Ile Asn Leu Leu Ser Phe Asp Phe His Gly Ser Trp
            195                 200                 205

Glu Lys Pro Leu Ile Thr Gly His Asn Ser Pro Leu Ser Lys Gly Trp
        210                 215                 220

Gln Asp Arg Gly Pro Ser Ser Tyr Tyr Asn Val Glu Tyr Ala Val Gly
225                 230                 235                 240

Tyr Trp Ile His Lys Gly Met Pro Ser Glu Lys Val Val Met Gly Ile
            245                 250                 255

Pro Thr Tyr Gly His Ser Phe Thr Leu Ala Ser Ala Glu Thr Thr Val
            260                 265                 270

Gly Ala Pro Ala Ser Gly Pro Gly Ala Ala Gly Pro Ile Thr Glu Ser
            275                 280                 285

Ser Gly Phe Leu Ala Tyr Tyr Glu Ile Cys Gln Phe Leu Lys Gly Ala
            290                 295                 300

Lys Ile Thr Arg Leu Gln Asp Gln Gln Val Pro Tyr Ala Val Lys Gly
305                 310                 315                 320

Asn Gln Trp Val Gly Tyr Asp Asp Val Lys Ser Met Glu Thr Lys Val
            325                 330                 335

Gln Phe Leu Lys Asn Leu Asn Leu Gly Gly Ala Met Ile Trp Ser Ile
            340                 345                 350

Asp Met Asp Asp Phe Thr Gly Lys Ser Cys Asn Gln Gly Pro Tyr Pro
            355                 360                 365
```

```
Leu Val Gln Ala Val Lys Arg Ser Leu Gly Ser Leu
    370                 375             380

<210> SEQ ID NO 54
<211> LENGTH: 380
<212> TYPE: PRT
<213> ORGANISM: Homo Sapiens

<400> SEQUENCE: 54

Met Gly Ala Thr Thr Met Asp Gln Lys Ser Leu Trp Ala Gly Ser Ala
1               5                   10                  15

Tyr Lys Leu Val Cys Tyr Phe Thr Asn Trp Ser Gln Asp Arg Gln Glu
            20                  25                  30

Pro Gly Lys Phe Thr Pro Glu Asn Ile Asp Pro Phe Leu Cys Ser His
            35                  40                  45

Leu Ile Tyr Ser Phe Ala Ser Ile Glu Asn Asn Lys Val Ile Ile Lys
            50                  55                  60

Asp Lys Ser Glu Val Met Leu Tyr Gln Thr Ile Asn Ser Leu Lys Thr
65                  70                  75                  80

Lys Asn Pro Lys Leu Lys Ile Leu Leu Ser Ile Gly Gly Tyr Leu Phe
                85                  90                  95

Gly Ser Lys Gly Phe His Pro Met Val Asp Ser Ser Thr Ser Arg Leu
            100                 105                 110

Glu Phe Ile Asn Ser Ile Ile Leu Phe Leu Arg Asn His Asn Phe Asp
            115                 120                 125

Gly Leu Asp Val Ser Trp Ile Tyr Pro Asp Gln Lys Glu Asn Thr His
            130                 135                 140

Phe Thr Val Leu Ile His Glu Leu Ala Glu Ala Phe Gln Lys Asp Phe
145                 150                 155                 160

Thr Lys Ser Thr Lys Glu Arg Leu Leu Leu Thr Ala Gly Val Ser Ala
                165                 170                 175

Gly Arg Gln Met Ile Asp Asn Ser Tyr Gln Val Glu Lys Leu Ala Lys
            180                 185                 190

Asp Leu Asp Phe Ile Asn Leu Leu Ser Phe Asp Phe His Gly Ser Trp
            195                 200                 205

Glu Lys Pro Leu Ile Thr Gly His Asn Ser Pro Leu Ser Lys Gly Trp
            210                 215                 220

Gln Asp Arg Gly Pro Ser Ser Tyr Tyr Asn Val Glu Tyr Ala Val Gly
225                 230                 235                 240

Tyr Trp Ile His Lys Gly Met Pro Ser Glu Lys Val Val Met Gly Ile
                245                 250                 255

Pro Thr Tyr Gly His Ser Phe Thr Leu Ala Ser Ala Glu Thr Thr Val
            260                 265                 270

Gly Ala Pro Ala Ser Gly Pro Gly Ala Ala Gly Pro Ile Thr Glu Ser
            275                 280                 285

Ser Gly Phe Leu Ala Tyr Tyr Glu Ile Cys Gln Phe Leu Lys Gly Ala
            290                 295                 300

Lys Ile Thr Arg Leu Gln Asp Gln Gln Val Pro Tyr Ala Val Lys Gly
305                 310                 315                 320

Asn Gln Trp Val Gly Tyr Asp Asp Val Lys Ser Met Glu Thr Lys Val
                325                 330                 335

Gln Phe Leu Lys Asn Leu Asn Leu Gly Gly Ala Met Ile Trp Ser Ile
            340                 345                 350

Asp Met Asp Asp Phe Thr Gly Lys Ser Cys Asn Gln Gly Pro Tyr Pro
```

```
          355                 360                 365
Leu Val Gln Ala Val Lys Arg Ser Leu Gly Ser Leu
    370                 375                 380

<210> SEQ ID NO 55
<211> LENGTH: 390
<212> TYPE: PRT
<213> ORGANISM: Homo Sapiens

<400> SEQUENCE: 55

Met Gly Ala Thr Thr Met Asp Gln Lys Ser Leu Trp Ala Gly Val Val
1               5                  10                  15

Val Leu Leu Leu Leu Gln Gly Gly Ser Ala Tyr Lys Leu Val Cys Tyr
            20                  25                  30

Phe Thr Asn Trp Ser Gln Asp Arg Gln Glu Pro Gly Lys Phe Thr Pro
        35                  40                  45

Glu Asn Ile Asp Pro Phe Leu Cys Ser His Leu Ile Tyr Ser Phe Ala
        50                  55                  60

Ser Ile Glu Asn Asn Lys Val Ile Ile Lys Asp Lys Ser Glu Val Met
65                  70                  75                  80

Leu Tyr Gln Thr Ile Asn Ser Leu Lys Thr Lys Asn Pro Lys Leu Lys
                85                  90                  95

Ile Leu Leu Ser Ile Gly Gly Tyr Leu Phe Gly Ser Lys Gly Phe His
            100                 105                 110

Pro Met Val Asp Ser Ser Thr Ser Arg Leu Glu Phe Ile Asn Ser Ile
        115                 120                 125

Ile Leu Phe Leu Arg Asn His Asn Phe Asp Gly Leu Asp Val Ser Trp
        130                 135                 140

Ile Tyr Pro Asp Gln Lys Glu Asn Thr His Phe Thr Val Leu Ile His
145                 150                 155                 160

Glu Leu Ala Glu Ala Phe Gln Lys Asp Phe Thr Lys Ser Thr Lys Glu
                165                 170                 175

Arg Leu Leu Leu Thr Ala Gly Val Ser Ala Gly Arg Gln Met Ile Asp
            180                 185                 190

Asn Ser Tyr Gln Val Glu Lys Leu Ala Lys Asp Leu Asp Phe Ile Asn
            195                 200                 205

Leu Leu Ser Phe Asp Phe His Gly Ser Trp Glu Lys Pro Leu Ile Thr
        210                 215                 220

Gly His Asn Ser Pro Leu Ser Lys Gly Trp Gln Asp Arg Gly Pro Ser
225                 230                 235                 240

Ser Tyr Tyr Asn Val Glu Tyr Ala Val Gly Tyr Trp Ile His Lys Gly
                245                 250                 255

Met Pro Ser Glu Lys Val Val Met Gly Ile Pro Thr Tyr Gly His Ser
            260                 265                 270

Phe Thr Leu Ala Ser Ala Glu Thr Thr Val Gly Ala Pro Ala Ser Gly
        275                 280                 285

Pro Gly Ala Ala Gly Pro Ile Thr Glu Ser Ser Gly Phe Leu Ala Tyr
        290                 295                 300

Tyr Glu Ile Cys Gln Phe Leu Lys Gly Ala Lys Ile Thr Arg Leu Gln
305                 310                 315                 320

Asp Gln Gln Val Pro Tyr Ala Val Lys Gly Asn Gln Trp Val Gly Tyr
                325                 330                 335

Asp Asp Val Lys Ser Met Glu Thr Lys Val Gln Phe Leu Lys Asn Leu
            340                 345                 350
```

```
Asn Leu Gly Gly Ala Met Ile Trp Ser Ile Asp Met Asp Asp Phe Thr
        355                 360                 365

Gly Lys Ser Cys Asn Gln Gly Pro Tyr Pro Leu Val Gln Ala Val Lys
        370                 375                 380

Arg Ser Leu Gly Ser Leu
385                 390

<210> SEQ ID NO 56
<211> LENGTH: 383
<212> TYPE: PRT
<213> ORGANISM: Homo Sapiens

<400> SEQUENCE: 56

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
        130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
        210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
        290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335
```

-continued

```
Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380
```